United States Patent
Gulla et al.

(10) Patent No.: US 11,858,986 B2
(45) Date of Patent: Jan. 2, 2024

(54) INTERFERON BETA ANTIBODIES AND USES THEREOF

(71) Applicants: PFIZER INC., New York, NY (US); THE BRIGHAM AND WOMEN'S HOSPITAL, INC., Boston, MA (US)

(72) Inventors: Stefano V. Gulla, Boston, MA (US); Christine Huard, Somerville, MA (US); Janet Elizabeth Buhlmann, Brookline, MA (US); Juan Carlos Almagro, Cambridge, MA (US); Sreekumar R. Kodangattil, Lexington, MA (US); Steven A. Greenberg, Newton, MA (US); Edward Roland Lavallie, Harvard, MA (US); Eric M. Bennett, Arlington, MA (US); Lidia Mosyak, Newton, MA (US); James Perry Hall, Stow, MA (US); Anthony John Coyle, Boston, MA (US)

(73) Assignees: Pfizer Inc., New York, NY (US); The Brigham And Women's Hospital, Inc., Boston, MA (US)

( * ) Notice: Subject to any disclaimer, the term of this patent is extended or adjusted under 35 U.S.C. 154(b) by 524 days.

(21) Appl. No.: 17/092,998

(22) Filed: Nov. 9, 2020

(65) Prior Publication Data
US 2021/0163588 A1 Jun. 3, 2021

Related U.S. Application Data

(62) Division of application No. 15/581,079, filed on Apr. 28, 2017, now Pat. No. 10,829,553.

(60) Provisional application No. 62/483,669, filed on Apr. 10, 2017, provisional application No. 62/339,709, filed on May 20, 2016, provisional application No. 62/329,327, filed on Apr. 29, 2016.

(51) Int. Cl.
*C07K 16/24* (2006.01)
*A61K 39/00* (2006.01)

(52) U.S. Cl.
CPC ...... *C07K 16/249* (2013.01); *A61K 2039/505* (2013.01); *C07K 2317/24* (2013.01); *C07K 2317/33* (2013.01); *C07K 2317/34* (2013.01); *C07K 2317/51* (2013.01); *C07K 2317/515* (2013.01); *C07K 2317/55* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,869,603 A | 2/1999 | Hoeprich | |
| 6,010,864 A | 1/2000 | Hoeprich, Jr. | |
| 6,180,370 B1 * | 1/2001 | Queen | A61P 31/12 |
| | | | 435/69.6 |
| 6,300,475 B1 | 10/2001 | Chen | |
| 9,266,955 B2 | 2/2016 | Dennis et al. | |
| 10,829,553 B2 | 11/2020 | Gulla et al. | |
| 2017/0313769 A1 | 11/2017 | Gulla | |
| 2018/0169240 A1 | 6/2018 | Parry et al. | |

FOREIGN PATENT DOCUMENTS

| | | |
|---|---|---|
| CN | 102898521 A | 1/2013 |
| EP | 0676413 B9 | 1/2005 |
| WO | 03/80672 A1 | 10/2003 |

OTHER PUBLICATIONS

Muskardin, Theresa L Wampler, and Timothy B Niewold. Nature reviews. Rheumatology vol. 14,4 (2018): 214-228. doi:10.1038/nrrheum.2018.31 (Year: 2018).*
D'Angelo, Debora M., et al. Frontiers in Pediatrics 9 (2021): 631329 (Year: 2021).*
Schwarting, Andreas, et al. Journal of the American Society of Nephrology 16.11 (2005): 3264-3272 (Year: 2005).*
Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
Hochkeppel, Heinz-Kurt, Ullrich Menge, and John Collins. "Monoclonal antibodies against human fibroblast interferon." European Journal of Biochemistry 118.3 (1981): 437-442. (Year: 1981).*
Govindappa et al., "Development of interferon beta-neutralising antibodies in multiple sclerosis—a systematic review and meta-analysis," European Journal of Clinical Pharmacology, 71(11):1287-98 (2015).
Dengyang et al., "Preparation of monoclonal antibody against recombinant human interferon-β1a," Journal of Cellular and Molecular Immunology, vol. 11, No. 31 (2015) (English Abstract Only).

(Continued)

*Primary Examiner* — Michael Szperka
*Assistant Examiner* — Lia E Taylor
(74) *Attorney, Agent, or Firm* — HALEY GUILIANO LLP; James F. Haley, Jr.; Brian M. Gummow

(57) ABSTRACT

The invention relates to antibodies, or antigen-binding fragments thereof, that specifically binds to interferon beta (IFNβ). Such antibodies, or antigen-binding fragments thereof, are are useful for various therapeutic or diagnostic purposes.

18 Claims, 12 Drawing Sheets

Specification includes a Sequence Listing.

(56) References Cited

OTHER PUBLICATIONS

Lunxiu, "Molecular Diagnosis and Prevention of Tumors," Shanghai Science and Technology Education Press (2004) (English Abstract Only).
Karpusas, et al., "The crystal structure of human interferon beta at 2.2-A resolution," PNAS, 94(22):11813-11818 (1997).
Runkel, et al., "Mapping of IFN-beta epitopes important for receptor binding and biologic activation: comparison of results achieved using antibody-based methods and alanine substitution mutagenesis," Journal of Interferon and Cytokine Research, 21(11):931-941 (2001).
Sheehan, et al., "Selective Blockade of Interferon-α and -β Reveals Their Non-Redundant Functions in a Mouse Model of West Nile Virus Infection," PLOS One, 10(5):e0128636 (2015).
Sominanda, et al., "Inhibition of endogenous interferon beta by neutralizing antibodies against recombinant interferon beta," Archives of Neurology, 67(9):1095-1101 (2010).
Rudikoff, S., et al., "Single amino acid substitution altering antigen-binding specificity," Proc. Natl. Acad, Sci, vol. 79, pp. 1979-1983, Mar. 1982.
Tamura et al., "Structural Correlates of an Anticarcinoma Antibody: Identification of Specificity-Determining Residues (SDRs) and Development of a Minimally Immunogenic Antibody Variant by Retention of SDRs Only", J. Immunol., 164:1432-1441 (2000).

\* cited by examiner

FIG. 11
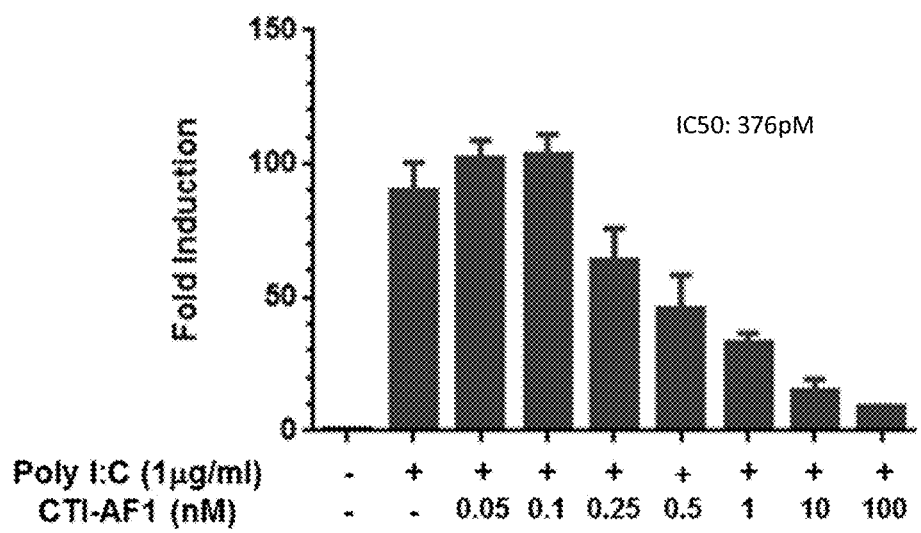
FIG. 12A  $IFN\beta_{skin}/IFN\beta_{plasma} = 10$    FIG. 12B  $IFN\beta_{skin}/IFN\beta_{plasma} = 100$
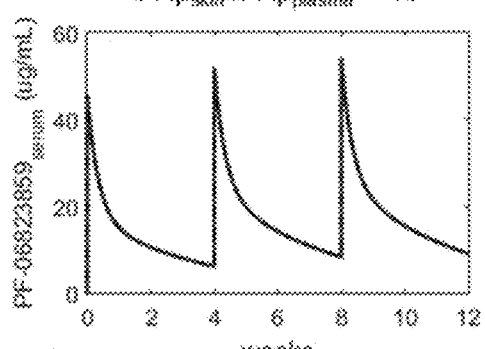 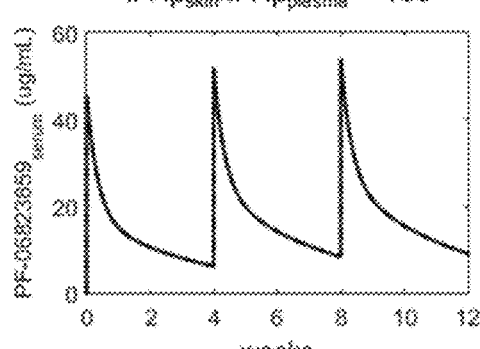
FIG. 12C    FIG. 12D
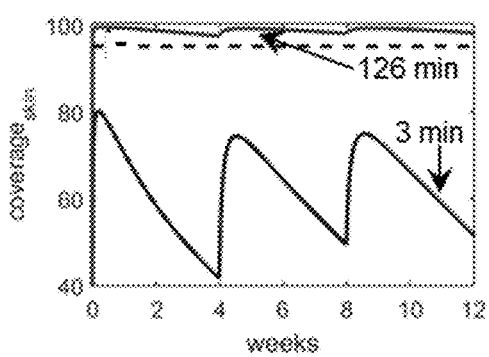 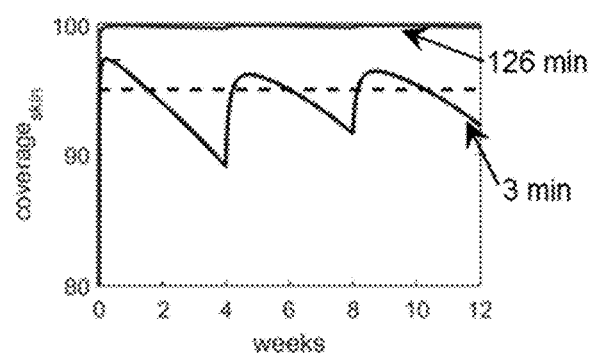
$IFN\beta\ t_{1/2}$ — 3 mins — 126 mins

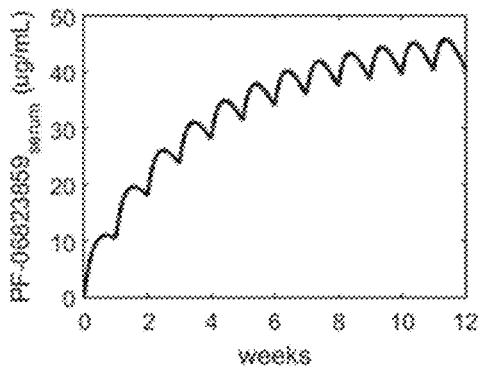
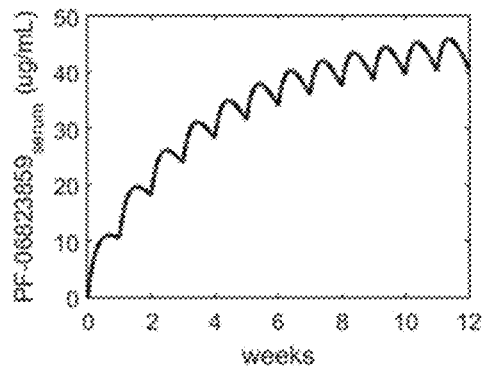
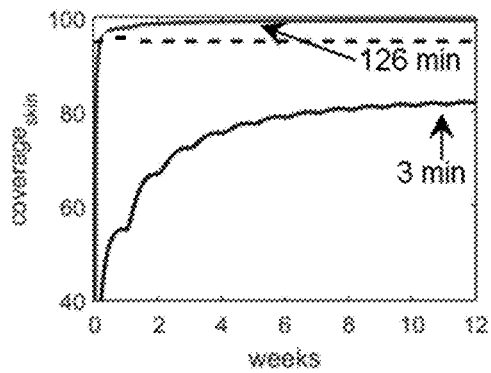
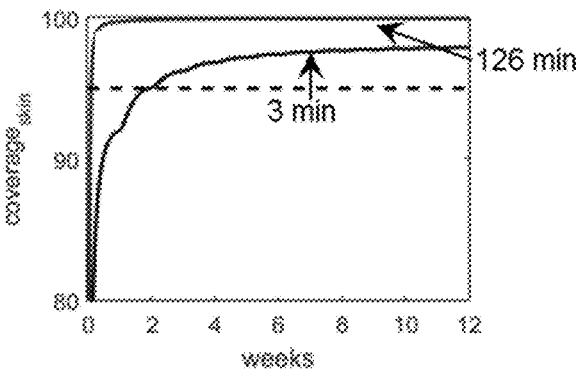
FIG. 13A, FIG. 13B, FIG. 13C, FIG. 13D
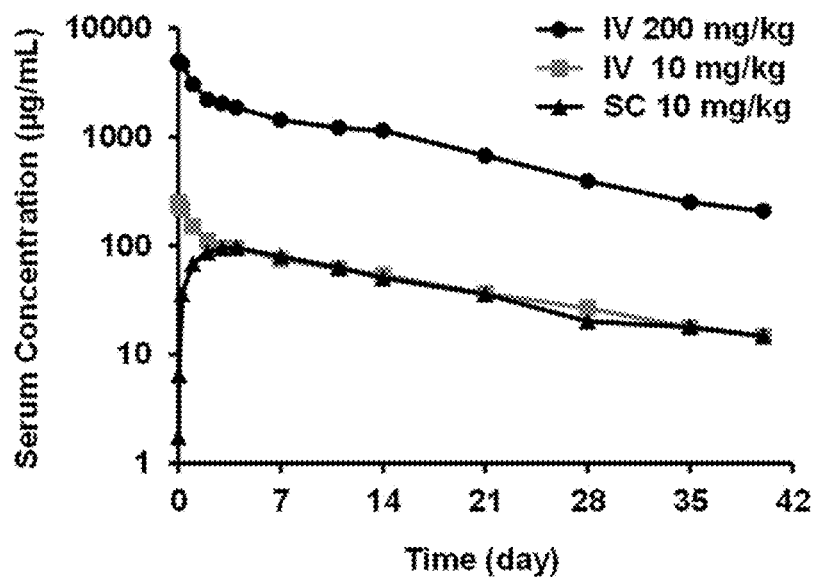
FIG. 14

FIG. 15A

```
         10         20         30         40         50
MSYNLLGFLQ RSSNFQCQKL LWQLNGRLEY CLKDRMNFDI PEEIKQLQQF
   |-----Helix A-------|--------------AB loop-----------

60         70         80         90        100
QKEDAALTIY EMLQNIFAIF RQDSSSTGWN ETIVENLLAN VYHQINHLKT
-|----Helix B-------|---BC loop--|-------Helix C------

110        120        130        140        150
VLEEKLEKED FTRGKLMSSL HLKRYYGRIL HYLKAKEYSH CAWTIVRVEI
------|----CD loop--|-------Helix D----|-DE-|---Helix E-

160        170
LRNFYFINRL TGYLRN
-----------|
```

FIG. 15B

```
sp|P01575|mouse    INYKQLQLQERTNIRKCQELLEQLNGKIN--LTYRADFKIPMEMT---EKMQKSYTAFAIQ
sp|P70499|rat      IDYKQLQFRQSTSIRTCQKLLRQLNGRLN--LSYRTDFKIPMEVMHPSQMEKSYTAFAIQ
tr|G1TTX4|rabbit   MSYNSLQIQLWHGSLTCAKLLQLNGTTEDCLNERINFKVPKEIKEPQQLQKEDTTLVIF
sp|P01574|human    MSYNLLGFLQRSSNFQCQKLLWQLNGRLEYCLKDRMNFDIPEEIKQLQQFQKEDAALTIY
sp|O77812|cyno     MSYNLLGFLQRSSSFQCQKLLWQLNGRLEYCLKDRMNFDIPEEIKQPQQFQKEDAALTIY
                   :.*: *  *         * : **  :   *.  * :* . *:   ..::*, :::.* sp|P01575|mouse    EMLQNVFLVFRNNFSSTGWNETIVVRLLDELHQQTVFLKTVLEEKQE-ERLTWEMSSTAL
sp|P70499|rat      VMLQNVFLVFRSNFSSTGWNETIVESLLDELHQQTELLEIILKEKQE-ERLTWVTSTTTL
tr|G1TTX4|rabbit   EMLNNIFDIFRKNFSSTGWNETLVENLLGETHLQIHHLKSKINKKVTLE-----SIRMNL
sp|P01574|human    EMLQNIFAIFRQDSSTGWNETIVENLLANVYHQINHLKTVLEEKLEKEDFTRGKLMSSL
sp|O77812|cyno     EMLQNIYAIFRQDLSSTGWNETIVENLLANVYHQIDHLKTILEEKLEKEDFTRGKFVSSL
                   **:*:: :.: ******:*  **  ; * *: ::: *     *           * sp|P01575|mouse    HLKSYYWRVQRYLKLMKYNSYAWMVVRAEIFRNFLIIRRLTRNFQN
sp|P70499|rat      GLKSYYWRVQRYLKDKKYNSYAWMVVRAEVFRNFSIILRLNRNPQN
tr|G1TTX4|rabbit   RLKSYYWRIMDYLETKQYSNCAWKIVQLEIPRNFSPIIMLIDYL--
sp|P01574|human    HLKRYYGRILHYLKAKEYSHCAWTIVRVEILRNFYFINRLTGYLRN
sp|O77812|cyno     HLKRYYGRILHYLKAKEYSHCAWTIVRVEILRNFFPINKLTGYLRN
                   ** ** *: **:  :*.  ** :*: *:;*** :*  *    :
```

INTERFERON BETA ANTIBODIES AND USES THEREOF

RELATED APPLICATIONS

This application is a divisional of U.S. patent application Ser. No. 15/581,079, filed Apr. 28, 2017, now U.S. Pat. No. 10,829,553 which claims the benefit of and priority from U.S. Provisional Patent Applications 62/483,669, filed Apr. 10, 2017, 62/339,709, filed May 20, 2016, and 62/329,327, filed Apr. 29, 2016. Each of the foregoing applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Feb. 18, 2021 is named PCFC-1000-102-SL.txt and is 94,268 bytes in size.

PARTIES TO A JOINT RESEARCH STATEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are PARTNERS HEALTHCARE and PFIZER INC.

BACKGROUND OF THE INVENTION

The interferon (IFN) family of cytokines was initially discovered by their ability to protect cells from viral infections, but it is now appreciated that this family of evolutionarily conserved cytokines can elicit a broad range of responses. The family is made up of the type I, type II, and type III IFN subfamilies, and the type I IFNs are the most diverse of all cytokine families. The human type I IFNs are encoded by 13 genes for IFNα subtypes, plus single genes for each of IFNβ, IFNω, IFNκ, and IFNε. IFNβ and the several IFNα isoforms are the best studied of the type I IFNs. Most IFNα proteins share 78-98% identity, and IFNβ shares ~35% identity with a consensus IFNα sequence. IFNβ is naturally glycosylated, whereas IFNα isoforms are typically only weakly glycosylated. All type I IFNs bind to the cell surface class II cytokine receptor IFNAR (composed of the two chains IFNAR1 and IFNAR2). IFNα has a half-life in serum of 2-3 hours, but IFNβ is hydrophobic and rarely detected in serum, and these characteristics are consistent with the notion that IFNα is effective systemically, whereas IFNβ acts at local sites in an autocrine/paracrine manner.

IFN production can be stimulated by exposure to microbe-derived pathogen-associated molecular patterns, including microbial nucleic acids, lipids, proteins, and lipoproteins. However, there is increasing evidence that IFN production can also be stimulated by endogenous self-components that are released during disease processes, and this is particularly relevant in the context of systemic lupus erythematosus (SLE) and other rheumatic diseases such as dermatomyositis (DM). A pathological overproduction of type I IFN expression often characterizes SLE, and IFNα is detectable in sera from a limited number of SLE patients. Increasing evidence also points to the importance of interferon-regulated gene (IRG) expression in the manifestation of SLE disease activity/severity, as evidenced by clinical results with the anti-IFNAR antibody anifrolimab. In a placebo-controlled phase 2 study, anifrolimab reduced disease severity across multiple clinical endpoints, while simultaneously inhibiting an IRG signature by approximately 90% at both doses tested in that study.

In addition to anti-IFN receptor antibody anifrolimab (anti-IFNAR), several anti-IFNα antibodies are under clinical development, such as sifalimumab, rontalizumab, and AGS-009. IFNα has been the focus of these efforts because a large body of evidence (including genetic, immunological, serological, and clinical studies) has associated IFNα with autoimmune disorders. However, based upon the scientific evidence to date it is expected that IFNβ will play a role similar to IFNα in autoimmune disorders. To date therapeutic antibodies that specifically target IFNβ (and not IFNα), have not been reported. Accordingly, there is an unmet need for an antibody that specially binds IFNβ for use in various therapeutic or diagnostic purposes.

SUMMARY OF THE INVENTION

The invention provides antibodies, and antigen-binding fragments thereof, that bind Interferon beta (IFNβ), as well as uses therefor, and associated methods.

Based on the disclosure provided herein, those skilled in the art will recognize, or be able to ascertain using no more than routine experimentation, many equivalents to the specific embodiments of the invention described herein. Such equivalents are intended to be encompassed by the following embodiments (E).

E1. An isolated antibody, or antigen-binding fragment thereof, that specifically binds human interferon β (IFNβ).

E2. The antibody, or antigen-binding fragment thereof, of embodiment 1, wherein said antibody, or antigen-binding fragment thereof, does not substantially bind a human IFNα.

E3. The antibody, or antigen-binding fragment thereof, of embodiment 1, wherein said antibody, or antigen-binding fragment thereof, binds human IFNβ with a binding affinity ($K_D$) value that is at least 100 fold less, at least 200 fold less, at least 300 fold less, at least 400 fold less, at least 500 fold less, at least 600 fold less, at least 700 fold less, at least 800 fold less, at least 900 fold less, or at least 1000 fold less, than its $K_D$ value for a human IFNα.

E4. An isolated antibody or antigen-binding fragment thereof, that specifically binds an epitope in human IFNβ, wherein said epitope comprises one or more residues from amino acid residues 85-100, according to the numbering of SEQ ID NO:41.

E5. An isolated antibody or antigen-binding fragment thereof, of embodiment 4, wherein said epitope comprises one or more residues selected from the group consisting of Ala89, Tyr 92, His93, and His97, according to the numbering of SEQ ID NO:41.

E6. The antibody, or antigen-binding fragment thereof, of embodiment 4 or 5, wherein said epitope comprises residues Ala89, Tyr 92, His93, and His97, according to the numbering of SEQ ID NO:41.

E7. The antibody, or antigen-binding fragment thereof, of any one of embodiments 4-6, wherein said epitope further comprises one or more residues selected from the group consisting of Phe8, Leu9, Ser12, Gln16, Asn86, Asn90, Asp96, and Thr100, according to the numbering of SEQ ID NO:41.

E8. The antibody, or antigen-binding fragment thereof, of any one of embodiments 4-7, wherein said epitope further comprises residues Phe8, Leu9, Ser12, Gln16, Asn86, Asn90, Asp96, and Thr100, according to the numbering of SEQ ID NO:41.

E9. The antibody, or antigen-binding fragment thereof, of any one of embodiments 4-8, wherein said epitope further comprises one or more residues selected from the group consisting of Leu5, Leu6, Ser13, Phe15, and Thr82, according to the numbering of SEQ ID NO:41.

E10. The antibody, or antigen-binding fragment thereof, of any one of embodiments 1-9, wherein said antibody, or antigen-binding fragment thereof, does not substantially bind mouse IFNβ.

E11. The antibody, or antigen-binding fragment thereof, of any one of embodiments 1-9, wherein said antibody, or antigen-binding fragment thereof, binds human IFNβ with a binding affinity ($K_D$) value that is at least 100 fold less, at least 200 fold less, at least 300 fold less, at least 400 fold less, at least 500 fold less, at least 600 fold less, at least 700 fold less, at least 800 fold less, at least 900 fold less, or at least 1000 fold less, than its $K_D$ value for mouse IFNβ.

E12. The antibody, or antigen-binding fragment thereof, of any one of embodiments 1-11, wherein said antibody, or antigen-binding fragment thereof, does not substantially bind rat IFNβ.

E13. The antibody, or antigen-binding fragment thereof, of any one of embodiments 1-11, wherein said antibody, or antigen-binding fragment thereof, binds human IFNβ with a binding affinity ($K_D$) value that is at least 100 fold less, at least 200 fold less, at least 300 fold less, at least 400 fold less, at least 500 fold less, at least 600 fold less, at least 700 fold less, at least 800 fold less, at least 900 fold less, or at least 1000 fold less, than its $K_D$ value for rat IFNβ.

E14. The antibody, or antigen-binding fragment thereof, of any one of embodiments 1-13, wherein said antibody, or antigen-binding fragment thereof, binds human IFNβ with a binding affinity ($K_D$) value that is at least at least 50 fold less, at least 100 fold less, at least 150 fold less, or at least 200 fold less, than its $K_D$ value for rabbit IFNβ.

E15. The antibody, or antigen-binding fragment thereof, of any one of embodiments 1-14, wherein said antibody, or antigen-binding fragment thereof, also specifically binds to Cynomolgus monkey IFNβ.

E16. The antibody, or antigen-binding fragment thereof, of any one of embodiments 3, 11, 13, and 14, wherein said $K_D$ value is measured by surface plasmon resonance (SPR), optionally using a Biacore T200 instrument.

E17. The antibody, or antigen-binding fragment thereof, of any one of embodiments 1-16, comprising a heavy chain variable region (VH) that comprises:
(a) a VH complementarity determining region one (CDR-H1) comprising the amino acid sequence of SEQ ID NO: 37,
(b) a VH complementarity determining region two (CDR-H2) comprising the amino acid sequence of SEQ ID NO: 38; and
(c) a VH complementarity determining region three (CDR-H3) comprising the amino acid sequence of SEQ ID NO: 39.

E18. The antibody, or antigen-binding fragment thereof, of any one of embodiments 1-17, comprising the CDR-H1, CDR-H2, and CDR-H3 sequences of SEQ ID NO: 28.

E19. An isolated antibody, or antigen-binding fragment thereof, that specifically binds human IFNβ, comprising a VH that comprises:
(a) a CDR-H1 comprising the amino acid sequence of SEQ ID NO: 37,
(b) a CDR-H2 comprising the amino acid sequence of SEQ ID NO: 38; and
(c) a CDR-H3 comprising the amino acid sequence of SEQ ID NO: 39.

E20. An isolated antibody, or antigen-binding fragment thereof, that specifically binds human IFNβ, comprising a VH that comprises one or more paratope residues selected from the group consisting of: Trp33 in CDR-H1, Tyr56 in CDR-H2, Tyr58 in CDR-H2, and Tyr97 in CDR-H3, according to Kabat numbering.

E21. The antibody, or antigen-binding fragment thereof, of embodiment 20, wherein said VH further comprises one or more paratope residues selected from the group consisting of: Asp54 in CDR-H2, Gln61 in CDR-H2, Gly98 in CDR-H3, and Leu100 in CDR-H3, according to Kabat numbering.

E22. The antibody, or antigen-binding fragment thereof, of any one of embodiments 1-21, comprising a VH framework derived from a human germline VH3, VH1, or VH5 framework sequence.

E23. The antibody, or antigen-binding fragment thereof, of any one of embodiments 1-21, comprising a VH framework sequence derived from human germline IGHV3-7, IGHV3-23, or IGHV1-69 framework sequence.

E24. The antibody, or antigen-binding fragment thereof, of any one of embodiments 1-21, comprising a VH framework sequence derived from human germline DP10, DP-88, DP-25, DP-73, IGHV5-10-1*01, IGHV5-10-1*04, DP-14, DP-75, DP15, DP-8, DP-7, or IGHV7-4-1*02 framework sequence, preferably DP-88, DP-25, DP-73, IGHV5-10-1*01, or IGFV-10-1*04 framework sequence.

E25. The antibody, or antigen-binding fragment thereof, of any one of embodiments 1-24, comprising a VH that comprises:
(a) a CDR-H1 comprising the amino acid sequence of SEQ ID NO: 37; a CDR-H2 comprising the amino acid sequence of SEQ ID NO: 38; and a CDR-H3 comprising the amino acid sequence of SEQ ID NO: 39; and
(b) a VH framework comprising a sequence that is at least 73%, at least 75%, at least 79%, at least 89%, at least 90%, at least 92%, at least 93%, or at least 99% identical to the framework sequence of human germline DP10.

E26. The antibody, or antigen-binding fragment thereof, of embodiment 25, wherein said VH framework further comprise four or fewer, three or fewer, or two or fewer amino acid differences, as compared to the framework sequence of human germline DP10, at the following positions (according to Kabat numbering): (A) H2, H47, H48, H49, H67, H69, H71, H73, H93, and H94; (B) H37, H39, H45, H47, H91, and H93; and (C) H24, H71, and H94.

E27. The antibody, or antigen-binding fragment thereof, of any one of embodiments 1-26, comprising a VH framework sequence derived from human germline DP10.

E28. The antibody, or antigen-binding fragment thereof, of any one of embodiments 1-21, comprising a human VH germline consensus framework sequence.

E29. The antibody, or antigen-binding fragment thereof, of any one of embodiments 1-28, comprising a VH sequence that is at least 91%, at least 92%, at least 93%, at least 94%, at least 95%, at least 96%, at least 97%, at least 98%, at least 99%, or 100% identical to SEQ ID NO: 28.

E30. The antibody, or antigen-binding fragment thereof, of any one of embodiments 1-29, comprising a light chain variable region (VL) that comprises:
  (a) a VL complementarity determining region one (CDR-L1) comprising the amino acid sequence of SEQ ID NO: 34,
  (b) a VL complementarity determining region two (CDR-L2) comprising the amino acid sequence of SEQ ID NO: 35; and
  (c) a VL complementarity determining region three (CDR-L3) comprising the amino acid sequence of SEQ ID NO: 36.

E31. The antibody, or antigen-binding fragment thereof, of any one of embodiments 1-30, comprising the CDR-L1, CDR-L2, and CDR-L3 sequences of SEQ ID NO: 1.

E32. The antibody, or antigen-binding fragment thereof, of any one of embodiments 1-29, comprising a VL that comprises one or more paratope residues selected from the group consisting of: Tyr32 in CDR-L1, Ile92 in CDR-L3, and Leu94 in CDR-L3, according to Kabat numbering.

E33. The antibody, or antigen-binding fragment thereof, of embodiment 32, wherein said VL further comprises one or more paratope residues selected from the group consisting of: Gln27 in CDR-L1, Asp28 in CDR-L1, Ile29 in CDR-L1, Gly30 in CDR-L1, and Ile93 in CDR-L3, according to Kabat numbering.

E34. An isolated antibody, or antigen-binding fragment thereof, that specifically binds human IFNβ, comprising the CDR-H1, CDR-H2, and CDR-H3 sequences of SEQ ID NO: 28, and the CDR-L1, CDR-L2, and CDR-L3 sequences of SEQ ID NO: 1.

E35. An isolated antibody, or antigen-binding fragment thereof, that specially binds human IFNβ, comprising:
  (i) a VH that comprises:
    (a) a CDR-H1 comprising the amino acid sequence of SEQ ID NO: 37,
    (b) a CDR-H2 comprising the amino acid sequence of SEQ ID NO: 38; and
    (c) a CDR-H3 comprising the amino acid sequence of SEQ ID NO: 39;
  and (ii) a VL that comprises:
    (a) a CDR-L1 comprising the amino acid sequence of SEQ ID NO: 34,
    (b) a CDR-L2 comprising the amino acid sequence of SEQ ID NO: 35; and
    (c) a CDR-L3 comprising the amino acid sequence of SEQ ID NO: 36.

E36. An isolated antibody, or antigen-binding fragment thereof, that specifically binds human IFNβ, comprising a VL that comprises one or more paratope residues selected from the group consisting of: Tyr32 in CDR-L1, Ile92 in CDR-L3, and Leu94 in CDR-L3, according to Kabat numbering.

E37. The antibody, or antigen-binding fragment thereof, of embodiment 36, wherein said VL further comprises one or more paratope residues selected from the group consisting of: Gln27 in CDR-L1, Asp28 in CDR-L1, Ile29 in CDR-L1, Gly30 in CDR-L1, and Ile93 in CDR-L3, according to Kabat numbering.

E38. An isolated antibody, or antigen-binding fragment thereof, that specially binds human IFNβ, comprising (numbering according to Kabat):
  (i) a VH that comprises:
    (a) a CDR-H1 comprising Trp33, and three or fewer amino acid differences as compared to SEQ ID NO: 37,
    (b) a CDR-H2 comprising Asp54, Tyr56, Tyr58, and Gln61, and three or fewer amino acid differences as compared to ID NO: 38; and
    (c) a CDR-H3 comprising Tyr97, Gly98, and Leu100; and three or fewer amino acid differences as compared to SEQ ID NO: 39; and
  (ii) a VL that comprises:
    (a) a CDR-L1 comprising Gln27, Asp28, Ile29, Gly30, Tyr32; and three or fewer amino acid differences as compared to SEQ ID NO: 34,
    (b) a CDR-L2 comprising a sequence that comprises three or fewer amino acid differences as compared to SEQ ID NO: 35; and
    (c) a CDR-L3 comprising Ile92, Ile93, and Leu94; and three or fewer amino acid differences as compared to of SEQ ID NO: 36.

E39. The antibody, or antigen-binding fragment thereof, embodiment 38, wherein said amino acid differences in CDR-H1, CDR-H2, CDR-L1, CDR-L2, and CDR-L3 are human germline substitutions in which a non-human CDR residue is replaced with a corresponding human germline residue.

E40. The antibody, or antigen-binding fragment thereof, of any one of embodiments 1-39, comprising a VL framework derived from a human germline $V_K$ or $V_\lambda$ framework sequence.

E41. The antibody, or antigen-binding fragment thereof, of any one of embodiments 1-39, comprising a VL framework derived from human germline IGKV1-39 or IGKV3-20 framework sequence.

E42. The antibody, or antigen-binding fragment thereof, of any one of embodiments 1-39, comprising a VL framework derived from human germline DPK9, DPK5, DPK4, DPK1, IGKV1-5*01, DPK24, DPK21, DPK15, IGKV1-13*02, IGKV1-17*01, DPK5, IGKV3-11*01, or DPK22 framework sequence, preferably DPK5, DPK4, DPK1, IGKV1-5*01, DPK24, DPK21, or DPK15 framework sequence.

E43. The antibody, or antigen-binding fragment thereof, of any one of embodiments 1-42, comprising a VL that comprises:
  (a) a CDR-L1 comprising the amino acid sequence of SEQ ID NO: 34; a CDR-L2 comprising the amino acid sequence of SEQ ID NO: 35; and a CDR-L3 comprising the amino acid sequence of SEQ ID NO: 36; and
  (b) a VL framework comprising a sequence that is at least 66%, at least 74%, at least 76%, at least 80%, at least 96%, at least 97%, or at least 99% identical to the framework sequence of human germline DPK9.

E44. The antibody, or antigen-binding fragment thereof, of embodiment 43, wherein said VL framework further comprise one amino acid difference, or no amino acid difference, as compared to the framework sequence of human germline DPK9, at the following positions (according to Kabat numbering): (A) L2, L4, L35, L36, L46, L47, L48, L49, L64, L66, L68, L69, and L71; (B) L36, L38, L44, L46, and L87; and (C) L2, L48, L64, and L71.

E45. The antibody, or antigen-binding fragment thereof, of any one of embodiments 1-44, comprising a VH framework sequence derived from human germline DPK9.

E46. The antibody, or antigen-binding fragment thereof, of any one of embodiments 1-39, comprising a human VL germline consensus framework sequence.

E47. The antibody, or antigen-binding fragment thereof, of any one of embodiments 1-46, comprising a VL sequence that is at least 94%, at least 95%, at least 96%, at least 97%, at least 98%, at least 99%, or 100% identical to SEQ ID NO:1.

E48. The antibody, or antigen-binding fragment thereof, of any one of embodiments 1-47, comprising a heavy chain constant region (CH) sequence that is at least 90%, at least 91%, at least 92%, at least 93%, at least 94%, at least 95%, at least 96%, at least 97%, at least 98%, at least 99%, or 100% identical to SEQ ID NO: 29.

E49. The antibody, or antigen-binding fragment thereof, of any one of embodiments 1-48, comprising a light chain constant region (CL) sequence that is at least 90%, at least 91%, at least 92%, at least 93%, at least 94%, at least 95%, at least 96%, at least 97%, at least 98%, at least 99%, or 100% identical to SEQ ID NO: 30.

E50. The antibody, or antigen-binding fragment thereof, of any one of embodiments 1-49, comprising an Fc domain.

E51. The antibody, or antigen-binding fragment thereof, of embodiment 50, wherein said Fc domain from an IgA, such as $IgA_1$ or $IgA_2$.

E52. The antibody, or antigen-binding fragment thereof, of embodiment 50, wherein said Fc domain is from an IgD.

E53. The antibody, or antigen-binding fragment thereof, of embodiment 50, wherein said Fc domain is from an IgE.

E54. The antibody, or antigen-binding fragment thereof, of embodiment 50, wherein said Fc domain is from an IgM.

E55. The antibody, or antigen-binding fragment thereof, of embodiment 50, wherein said Fc domain is from an IgG.

E56. The antibody, or antigen-binding fragment thereof, of embodiment 55, wherein said IgG is $IgG_1$, $IgG_2$, $IgG_3$, or $IgG_4$.

E57. The antibody, or antigen-binding fragment thereof, of any one of embodiments 1-56, comprising a heavy chain that comprises an amino acid sequence that is at least 91%, at least 92%, at least 93%, at least 94%, at least 95%, at least 96%, at least 97%, at least 98%, at least 99%, or 100% identical to SEQ ID NO: 33.

E58. The antibody, or antigen-binding fragment thereof, of any one of embodiments 1-57, comprising a light chain that comprises an amino acid sequence that is at least 91%, at least 92%, at least 93%, at least 94%, at least 95%, at least 96%, at least 97%, at least 98%, at least 99%, or 100% identical to SEQ ID NO: 32.

E59. The antibody, or antigen-binding fragment thereof, of any one of embodiments 1-58, comprising the VH sequence encoded by the insert in the plasmid deposited with the ATCC and having ATCC Accession No. PTA-122727.

E60. The antibody, or antigen-binding fragment thereof, of any one of embodiments 1-59, comprising the VL sequence encoded by the insert in the plasmid deposited with the ATCC and having ATCC Accession No. PTA-122726.

E61. An isolated antibody, or antigen-binding fragment thereof, that specifically binds human IFNβ, comprising (a) the CDR-H1, CDR-H2, and CDR-H3 sequences of SEQ ID NO: 28, and (b)
   i) the CDR-L1, CDR-L2, and CDR-L3 sequences of SEQ ID NO: 2;
   ii) the CDR-L1, CDR-L2, and CDR-L3 sequences of SEQ ID NO: 3;
   iii) the CDR-L1, CDR-L2, and CDR-L3 sequences of SEQ ID NO: 4;
   iv) the CDR-L1, CDR-L2, and CDR-L3 sequences of SEQ ID NO: 5;
   v) the CDR-L1, CDR-L2, and CDR-L3 sequences of SEQ ID NO: 6;
   vi) the CDR-L1, CDR-L2, and CDR-L3 sequences of SEQ ID NO: 7;
   vii) the CDR-L1, CDR-L2, and CDR-L3 sequences of SEQ ID NO: 8;
   viii) the CDR-L1, CDR-L2, and CDR-L3 sequences of SEQ ID NO: 9;
   ix) the CDR-L1, CDR-L2, and CDR-L3 sequences of SEQ ID NO: 10;
   x) the CDR-L1, CDR-L2, and CDR-L3 sequences of SEQ ID NO: 11;
   xi) the CDR-L1, CDR-L2, and CDR-L3 sequences of SEQ ID NO: 12;
   xii) the CDR-L1, CDR-L2, and CDR-L3 sequences of SEQ ID NO: 13;
   xiii) the CDR-L1, CDR-L2, and CDR-L3 sequences of SEQ ID NO: 14;
   xiv) the CDR-L1, CDR-L2, and CDR-L3 sequences of SEQ ID NO: 15;
   xv) the CDR-L1, CDR-L2, and CDR-L3 sequences of SEQ ID NO: 16;
   xvi) the CDR-L1, CDR-L2, and CDR-L3 sequences of SEQ ID NO: 17;
   xvii) the CDR-L1, CDR-L2, and CDR-L3 sequences of SEQ ID NO: 18;
   viii) the CDR-L1, CDR-L2, and CDR-L3 sequences of SEQ ID NO: 19;
   xix) the CDR-L1, CDR-L2, and CDR-L3 sequences of SEQ ID NO: 20;
   xx) the CDR-L1, CDR-L2, and CDR-L3 sequences of SEQ ID NO: 21;
   xxi) the CDR-L1, CDR-L2, and CDR-L3 sequences of SEQ ID NO: 22;
   xxii) the CDR-L1, CDR-L2, and CDR-L3 sequences of SEQ ID NO: 23;
   xxiii) the CDR-L1, CDR-L2, and CDR-L3 sequences of SEQ ID NO: 24;
   xxiv) the CDR-L1, CDR-L2, and CDR-L3 sequences of SEQ ID NO: 25;
   xxv) the CDR-L1, CDR-L2, and CDR-L3 sequences of SEQ ID NO: 26; or xxvi) the CDR-L1, CDR-L2, and CDR-L3 sequences of SEQ ID NO: 27.

E62. An isolated antibody, or antigen-binding fragment thereof, that specifically binds human IFNβ, comprising a VH that comprises the amino acid sequence of SEQ ID NO:28, and a VL that comprises the amino acid sequence of any one of SEQ ID NOs. 2-27.

E63. The antibody, or antigen-binding fragment thereof, of embodiment 61 or 62, comprising an Fc domain.

E64. The antibody, or antigen-binding fragment thereof, of embodiment 63, wherein said Fc domain is from an IgA (e.g., $IgA_1$ or $IgA_2$), IgD, IgE, IgM, or IgG (e.g., $IgG_1$, $IgG_2$, $IgG_3$, or $IgG_4$).

E65. The antibody, or antigen-binding fragment thereof, of any one of embodiments 61-64, comprising a CH that comprises the amino acid sequence of SEQ ID NO: 29.

E66. The antibody, or antigen-binding fragment thereof, of any one of embodiments 61-65, comprising a CL that comprises the amino acid sequence of SEQ ID NO: 30.

E67. An antibody, or antigen-binding fragment thereof, that competes for specific binding to human IFNβ with an antibody, or antigen-binding fragment thereof, of any one of embodiments 1-66.

E68. An antibody, or antigen-binding fragment thereof, that competes for specific binding to human IFNβ with CTI-AF1, or an antigen-binding fragment of CTI-AF1.

E69. An antibody, or antigen-binding fragment thereof, that competes for specific binding to human IFNβ with one or more antibodies selected from the group consisting of: CTI-AF2, CTI-AF3, CTI-AF4, CTI-AFS, CTI-AF6, CTI-AF7, CTI-AF8, CTI-AF9, CTI-AF10, CTI-AF11, CTI-AF12, CTI-AF13, CTI-AF14, CTI-AF15, CTI-AF16, CTI-AF17, CTI-AF18, CTI-AF19, CTI-AF20, CTI-AF21, CTI-AF22, CTI-AF23, CTI-AF24, CTI-AF25, CTI-AF26, CTI-AF27, and an antigen-binding fragment thereof.

E70. An antibody, or antigen-binding fragment thereof, that specifically binds human IFNβ, wherein said antibody, or antigen-binding fragment thereof, binds substantially the same epitope as CTI-AF1, or an antigen-binding fragment of CTI-AF1.

E71. An antibody, or antigen-binding fragment thereof, that specifically binds human IFNβ, wherein said antibody, or antigen-binding fragment thereof, binds substantial the same epitope as one or more antibodies, or antigen-binding fragments thereof, selected from the group consisting of: CTI-AF2, CTI-AF3, CTI-AF4, CTI-AF5, CTI-AF6, CTI-AF7, CTI-AF8, CTI-AF9, CTI-AF10, CTI-AF11, CTI-AF12, CTI-AF13, CTI-AF14, CTI-AF15, CTI-AF16, CTI-AF17, CTI-AF18, CTI-AF19, CTI-AF20, CTI-AF21, CTI-AF22, CTI-AF23, CTI-AF24, CTI-AF25, CTI-AF26, and CTI-AF27.

E72. The antibody, or antigen-binding fragment thereof, of any one of embodiments 1-71, wherein the antibody, or antigen-binding fragment, is an Fc fusion protein, a monobody, a maxibody, a bifunctional antibody, an scFab, an scFv, a peptibody, or an antigen-binding fragment of any of the foregoing.

E73. The antibody, or antigen-binding fragment thereof, of any one of embodiments 1-72, wherein said antibody, or antigen-binding fragment thereof, binds human IFNβ with a binding affinity ($K_D$) value no greater than about $5 \times 10^{-9}$ M.

E74. The antibody, or antigen-binding fragment thereof, of any one of embodiments 1-73, wherein said antibody, or antigen-binding fragment thereof, binds human IFNβ with a binding affinity ($K_D$) value no greater than about $1 \times 10^{-9}$ M.

E75. The antibody, or antigen-binding fragment thereof, of any one of embodiments 1-74, wherein said antibody, or antigen-binding fragment thereof, binds human IFNβ with a binding affinity ($K_D$) value from about $1 \times 10^{-9}$ M to about $1 \times 10^{-14}$ M.

E76. The antibody, or antigen-binding fragment thereof, of any one of embodiments 1-75, wherein said antibody or antigen-binding fragment (a) inhibits binding of IFNβ and IFNAR; (b) reduces the expression level of an IFNβ-dependent gene; and/or (c) inhibits IFNβ induced STAT1 or STAT2 phosphorylation.

E77. The antibody, or antigen-binding fragment thereof, of embodiment 76, wherein said antibody, or antigen-binding fragment thereof, inhibits binding of IFNβ and IFNAR with an $IC_{50}$ value of about $5 \times 10^{-9}$ M or less.

E78. The antibody, or antigen-binding fragment thereof, of embodiment 76, wherein said antibody, or antigen-binding fragment thereof, inhibits binding of IFNβ and IFNAR with an $IC_{50}$ value from about $1 \times 10^{-9}$ M to about $1 \times 10^{-14}$ M.

E79. An isolated nucleic acid molecule encoding the antibody, or antigen-binding fragment thereof, of any one of embodiments 1-78.

E80. An isolated nucleic acid comprising the nucleotide sequence of SEQ ID NO:166

E81. An isolated nucleic acid comprising the nucleotide sequence of SEQ ID NO:167.

E82. An isolated nucleic acid comprising the nucleotide sequence of the insert of the plasmid deposited at the ATCC and having Accession Number PTA-122727.

E83. An isolated nucleic acid comprising the nucleotide sequence of the insert of the plasmid deposited at the ATCC and having Accession Number PTA-122726.

E84. A vector comprising the nucleic acid molecule of any one of embodiments 79-83.

E85. A host cell comprising the nucleic acid molecule of any one of embodiments 79-83, or the vector of embodiment 84.

E86. The host cell of embodiment 85, wherein the cell is a mammalian cell.

E87. The host cell of embodiment 85 or 83, wherein the host cell is a CHO cell, a HEK-293 cell, or an Sp2.0 cell.

E88. A method of producing an antibody, or antigen-binding fragment thereof, comprising culturing the host cell of any one of embodiments 85-87, under conditions wherein the antibody, or antigen-binding fragment thereof, is produced by the host cell.

E89. The method of embodiment 88, further comprising isolating the antibody, or antigen-binding fragment thereof.

E90. An antibody, or antigen-binding fragment thereof, obtained by the method of embodiment 88 or 89.

E91. A pharmaceutical composition comprising an antibody, or antigen-binding fragment thereof, of any one of embodiments 1-78 and 90, and a pharmaceutically acceptable carrier.

E92. A method of reducing the activity of IFNβ, comprising administering to a subject in need thereof a therapeutically effective amount of the antibody, or antigen-binding fragment thereof, of any one of embodiments 1-78 and 90, or the pharmaceutical composition of embodiment 91.

E93. A method of treating a rheumatic disease, comprising administering to a subject in need thereof a therapeutically effective amount of the antibody, or antigen-binding fragment thereof, of any one of embodiments 1-78 and 90, or the pharmaceutical composition of embodiment 91.

E94. A method of treating systemic lupus erythematosus (SLE), comprising administering to a subject in need thereof a therapeutically effective amount of The antibody, or antigen-binding fragment thereof, of any one of embodiments 1-78 and 90, or the pharmaceutical composition of embodiment 91.

E95. A method of treating dermatomyositis (DM), comprising administering to a subject in need thereof a therapeutically effective amount of the antibody, or antigen-binding fragment thereof, of any one of embodiments 1-78 and 90, or the pharmaceutical composition of embodiment 91.

E96. A method of treating an interferonopathy, comprising administering to a subject in need thereof a therapeutically effective amount of the antibody, or antigen-binding fragment thereof, of any one of embodiments 1-78 and 90, or the pharmaceutical composition of embodiment 91.

E97. The method of any one of embodiments 92-96, wherein said subject is a human.

E98. The method of any one of embodiments 92-97, comprising administering said antibody or antigen-binding fragment thereof, or pharmaceutical composition, intravenously.

E99. The method of any one of embodiments 92-98, comprising administering said antibody or antigen-binding fragment thereof, or pharmaceutical composition, subcutaneously.

E100. The method of any one of embodiments 92-99, wherein said antibody or antigen-binding fragment thereof, or pharmaceutical composition, is administered twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, or once every three months.

E101. The antibody, or antigen-binding fragment thereof, of any one of embodiments 1-78 and 90, or the pharmaceutical composition of embodiment 91, for use as a medicament.

E102. The antibody, or antigen-binding fragment thereof, of any one of embodiments 1-78 and 90, or the pharmaceutical composition of embodiment 91, for use in reducing the activity of IFNβ in a subject.

E103. The antibody, or antigen-binding fragment thereof, of any one of embodiments 1-78 and 90, or the pharmaceutical composition of embodiment 91, for use in treating a rheumatic disease in a subject.

E104. The antibody, or antigen-binding fragment thereof, of any one of embodiments 1-78 and 90, or the pharmaceutical composition of embodiment 91, for use in treating SLE in a subject.

E105. The antibody, or antigen-binding fragment thereof, of any one of embodiments 1-78 and 90, or the pharmaceutical composition of embodiment 91, for use in treating DM in a subject.

E106. The antibody, or antigen-binding fragment thereof, of any one of embodiments 1-78 and 90, or the pharmaceutical composition of embodiment 91, for use in treating an interferonopathy in a subject.

E107. The antibody or antigen-binding fragment, or pharmaceutical composition of any one of embodiments 101-106, wherein said subject is a human.

E108. Use of the antibody, or antigen-binding fragment thereof, of any one of embodiments 1-78 and 90, or the pharmaceutical composition of embodiment 91, for reducing the activity of IFNβ in a subject.

E109. Use of the antibody, or antigen-binding fragment thereof, of any one of embodiments 1-78 and 90, or the pharmaceutical composition of embodiment 91, in the manufacture of a medicament for reducing the activity of IFNβ in a subject.

E110. Use of the antibody, or antigen-binding fragment thereof, of any one of embodiments 1-78 and 90, or the pharmaceutical composition of embodiment 91, for treating a rheumatic disease in a subject.

E111. Use of the antibody, or antigen-binding fragment thereof, of any one of embodiments 1-78 and 90, or the pharmaceutical composition of embodiment 91, in the manufacture of a medicament for treating a rheumatic disease in a subject.

E112. Use of the antibody, or antigen-binding fragment thereof, of any one embodiments 1-78 and 90, or the pharmaceutical composition of embodiment 91, for treating SLE in a subject.

E113. Use of the antibody, or antigen-binding fragment thereof, of any one of embodiments 1-78 and 90, or the pharmaceutical composition of embodiment 91, in the manufacture of a medicament for treating SLE in a subject.

E114. Use of the antibody, or antigen-binding fragment thereof, of any one of embodiments 1-78 and 90, or the pharmaceutical composition of embodiment 91, for treating DM in a subject.

E115. Use of the antibody, or antigen-binding fragment thereof, of any one of embodiments 1-78 and 90, or the pharmaceutical composition of embodiment 91, in the manufacture of a medicament for treating DM in a subject.

E116. Use of the antibody, or antigen-binding fragment thereof, of any one of embodiments 1-78 and 90, or the pharmaceutical composition of embodiment 91, for treating an interferonopathy in a subject.

E117. Use of the antibody, or antigen-binding fragment thereof, of any one of embodiments 1-78 and 90, or the pharmaceutical composition of embodiment 91, in the manufacture of a medicament for treating an interferonopathy in a subject.

E118. The use of any one of embodiments 108-117, wherein said subject is a human.

BRIEF DESCRIPTION OF THE DRAWINGS

(FIG. 5A, T0 equals no time at 40° C.) had no loss of neutralizing activity; Storage at 40° C. for two or three weeks had no impact on activity (FIG. 5C). Material that was produced after transfection of CHO cells instead of HEK293 cells or containing a mutation of amino acid 44 from a phenylalanine to a proline had no impact on neutralization (FIG. 5B). Finally, material stored for four weeks at 40° C. or five weeks at room temperature (FIG. 5D) had no impact on the ability of CTI-AF1 to neutralize IFNβ induced activity.

FIG. 8A shows that HEK293 cells stably transduced with an IFN stimulated response element (ISRE) luciferase reporter construct were stimulated in the presence of IFNβ and titrated amounts of CTI-AF1. A dose-dependent inhibition of luminescence is seen indicating that IFNβ has been neutralized. Binding of IFNβ to the interferon receptor (IFNAR) is known to induce the phosphorylation of the STAT1 protein in U937 cells. FIG. 8B shows STAT1 phosphorylation analysis. U937 cells were exposed to IFNβ, pre-incubated with titrated amounts of CTI-AF1 for 15 minutes, then the level of STAT1 phosphorylation was evaluated. The data show that there is a dose-dependent inhibition of STAT1 phosphorylation, indicating that IFNβ dependent signals have been neutralized by CTI-AF1.

FIG. 11 demonstrates that CTI-AF1 was a potent inhibitor of endogenous IFNβ secreted by primary human dermal fibroblasts (HDF). HDF were stimulated with polyinosinic:polycytidylic acid (poly I:C) for 24 hours to induce the expression of IFNβ in the presence of titrated amounts of CTI-AF1 and then Mx1 (MxA) gene expression was evaluated as described in FIG. 9. A dose-dependent inhibition of Mx1 (MxA) gene expression was seen with increasing amounts of CTI-AF1 demonstrating the antibody neutralized endogenously produced IFNβ.

FIGS. 12A-12D depict CTI-AF1 serum PK and IFNβ skin coverage profiles in human at 2 mg/kg IV Q4W. Profiles are shown for IFNβ skin:plasma ratio of 10 (FIGS. 12A and 12C) and 100 (FIGS. 12B and 12D). Note that CTI-AF1 serum PK is not impacted by IFNβ skin:plasma ratio and IFNβ turnover half-life. The dashed lines in panels C and D represent 95% IFNβ coverage in skin.

FIGS. 13A-13D show the profiles for IFNβ skin:plasma ratio of 10 (FIGS. 13A and 13C) and 100 (FIGS. 13B and 13D). Note that serum PK is not impacted by IFNβ skin:plasma ratio and IFNβ turnover half-life. The dashed lines in panels C and D represent 95% IFNβ coverage in skin.

FIG. 14 shows the mean serum concentrations of CTI-AF1 in cynomolgus monkeys from toxicity study.

FIG. 15A shows the sequence and secondary structure of human IFNβ (SEQ ID NO:41). FIG. 15B shows the sequence alignment of human (SEQ ID NO:41), cynomolgus (SEQ ID NO:44), mouse (SEQ ID NO:42), rat (SEQ ID NO:43), and rabbit (SEQ ID NO: 45) IFNβ sequences.

DETAILED DESCRIPTION OF THE INVENTION

1. Anti-IFNβ Antibodies

A. Interferon Beta (IFNβ)

Figure 1:
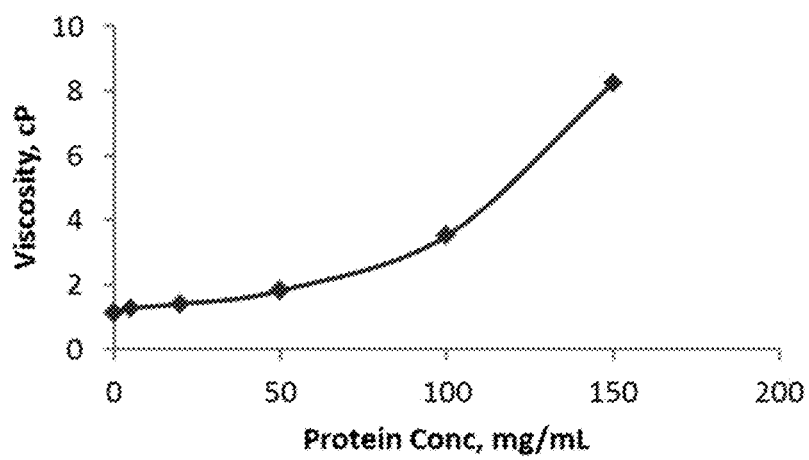
FIG. 1 shows the viscosity of IFNβ antibody in MOD1 buffer.

Interferon beta (IFNβ), also known as fibroblast IFN, is a glycosylated, secreted, and approximately 22 kDa member of the type I interferon family of molecules. The sequence of human IFNβ precursor is shown as SEQ ID NO: 40. A signal peptide (residues 1-21 of SEQ ID NO: 40) of the precursor is cleaved to produce mature IFNβ (SEQ ID NO: 41), which shares 47% and 46% amino acid sequence identity with the mouse and rat proteins, respectively. Alignments of IFNβ from various species are shown in FIG. 15B. The signal peptide is underlined in the sequence below.

```
MTNKCLLQIA LLLCFSTTAL SMSYNLLGFL QRSSNFQCQK

LLWQLNGRLE YCLKDRMNFD IPEEIKQLQQ FQKEDAALTI

YEMLQNIFAI FRQDSSSTGW NETIVENLLA NVYHQINHLK

TVLEEKLEKE DFTRGKLMSS LHLKRYYGRI LHYLKAKEYS

HCAWTIVRVE ILRNEYFINR LTGYLRN (Human IFNβ precursor, SEQ ID NO: 40)
```

The structure of IFNβ contains 5 α-helices, designated A (YNLLGFLQRSSNFQCQKLL; SEQ ID NO:153 or residues 3-21 of SEQ ID NO:41), B (KEDAALTIYEMLQNI-FAIF; SEQ ID NO:154 or residues 52-70 of SEQ ID NO:41), C (ETIVENLLANVYHQINHLKTVLEEKL; SEQ ID NO:155 or residues 81-106 of SEQ ID NO:41), D (SLHLKRYYGRILHYLKA; SEQ ID NO:156 or residues 119-135 of SEQ ID NO:41), and E (HCAW-TIVRVEILRNFYFINRLT; SEQ ID NO:157 or residues 140-161 of SEQ ID NO:41). The five α-helices are interconnected by loops of 2 to 28 residues designated AB, BC, CD, and DE loops (FIG. 15A). It has been reported that the A helix, the AB loop, and the E helix are involved in binding of IFNβ to its receptor, IFNAR.

B. Anti-IFNβ Antibodies

One potential drawback of an anti-IFNAR antibody (e.g., anifrolimab) is that both IFNα and IFNβ cytokines bind to IFNAR. Although these two types of IFN cytokines elicit similar biological activities to a similar degree, there are significant differences in potency and cell type specific activities between these two types of IFNs. For example, IFNβ elicits a markedly higher anti-proliferative response in some cell types, such as embryonal carcinoma, melanoma and melanocytes, than does IFNα. Higher potency of IFNβ in treatment of multiple sclerosis and certain cancers has also been observed. Blocking the activity of IFNAR, however, does not selectively modulate the activities of IFNβ. Significantly, IFNα is an important cytokine in response to viral infections, such that blocking its activity may have unwanted effects. Accordingly, an antibody that specially binds IFNβ, but not IFNα, would fulfill a significant unmet need for treatment of diseases that are primarily driven by IFNβ.

In one aspect, the invention provides an isolated antibody, or antigen-binding fragment thereof, that specifically binds human IFNβ. Sequences of exemplary antibodies of the invention are shown in Table 11.

As shown in the Examples, in certain embodiments, the antibody of the invention inhibits the binding of IFNβ to its receptor, and is hence referred to as a "neutralizing" antibody. Without wishing to be bound by any particular theory, the data indicate that the antibody, or antigen-binding fragment thereof, blocks, or partially blocks, the receptor binding sites of IFNβ, either by competing for the same or overlapping residues from IFNAR, or by creating steric hindrance.

For example, residues from helix A, AB loop, and helix E of IFNβ are believed to be involved in binding of IFNβ to its receptor. Accordingly, in certain embodiments, the antibody, or antigen-binding fragment thereof, of the invention binds an epitope comprising one more residues selected from the group consisting of: residues 3-21 (helix A), 22-51 (AB loop); and 140-161 (helix E), according to the numbering of SEQ ID NO: 41.

In certain embodiments, the antibody, or antigen-binding fragment thereof, bind to human IFNβ with a binding affinity ($K_D$) value that is at least 100 fold less, than its $K_D$ value for a human IFNα under substantially the same assay conditions. For example, the ratio of $K_D$ for IFNβ versus $K_D$ for IFNα can be 1:100 or less, 1:250 or less, 1:500 or less, 1:1000 or less, 1:2500 or less, 1:5000 or less, or 1:10,000 or less.

Mutagenesis studies and crystal structure studies also identified epitope residues in human IFNβ that are recognized by anti-IFNβ antibodies disclosed herein. In particular, among all IFNβ residues that are within 3.8 Å from a heavy atom of the antibody ("potential" epitope residues), three different types have been identified: (i) "primary" epitope residues that are characterized as highly buried residues at the of antibody-antigen interface and zero-to-low sequence tolerance to any other amino acid substitutions at this position; (ii) "secondary" epitope residues that are characterized as residues with medium buried surface area at the interface and medium sequence tolerance to amino acid substitutions at these positions; and (iii) "Optional" epitope residues are characterized as residues with low buried surface area at the interface and high sequence tolerance to amino acid substitutions at these positions.

Accordingly, in certain embodiments, the antibody, or antigen-binding fragment thereof, of the invention specifically binds an epitope in human IFNβ, wherein said epitope comprises one or more residues selected from the group consisting of Ala89, Tyr 92, His93, and His97, according to the numbering of SEQ ID NO:41 ("primary" epitope residues). In certain embodiments, the epitope further comprises one or more residues selected from the group consisting of Phe8, Leu9, Ser12, Gln16, Asn86, Asn90, Asp96, and Thr100, according to the numbering of SEQ ID NO:41 ("secondary" epitope residues). In certain embodiments, the epitope further comprises one or more residues selected from the group consisting of Leu5, Leu6, Ser13, Phe15, and Thr82, according to the numbering of SEQ ID NO:41 ("optional" epitope residues).

In certain embodiments, the antibody, or antigen-binding fragment thereof, of the invention also specifically binds cynomolgus monkey IFNβ, in addition to human IFNβ. In certain embodiments, the antibody, or antigen-binding fragment thereof, of the invention specifically binds an epitope in cynomolgus monkey IFNβ, wherein said epitope comprises one or more residues selected from the group consisting of Ala89, Tyr 92, His93, and His97, according to the numbering of SEQ ID NO:44 ("primary" epitope residues). In certain embodiments, the epitope further comprises one or more residues selected from the group consisting of Phe8, Leu9, Ser12, Gln16, Asn86, Asn90, Asp96, Thr100 and Tyr67, according to the numbering of SEQ ID NO:44 ("secondary" epitope residues). In certain embodiments, the epitope further comprises one or more residues selected from the group consisting of Leu5, Leu6, Ser13, Phe15, and Thr82, according to the numbering of SEQ ID NO:44 ("optional" epitope residues).

Provided herein are antibody CTI-AF1 and variants thereof. Accordingly, in certain embodiments, the antibody or antigen-binding fragment thereof comprises the following heavy chain CDR sequences: (i) CDR-H1 comprising SEQ ID NO: 37, CDR-H2 comprising SEQ ID NO: 38, and CDR-H3 comprising SEQ ID NO: 39; and/or (ii) the following light chain CDR sequences: CDR-L1 comprising SEQ ID NO: 34, CDR-L2 comprising SEQ ID NO: 35, and CDR-L3 comprising SEQ ID NO: 36.

As demonstrated from the crystal structure studies, not all residues in CDRs contribute to antibody-antigen binding. As shown in Example 7 and Table 14, only limited number of CDR residues are within 3.8 Å from a heavy atom of the antigen, and are considered as potential paratope residues. Among these potential paratope residues, (i) "primary" paratope residues are those characterized as highly buried residues at the antibody-antigen interface and low sequence tolerance to any other amino acid substitutions at this position; and (ii) "secondary" paratope residues are characterized as residues with lower buried surface area at the interface and higher sequence tolerance to amino acid substitutions at these positions.

Accordingly, in certain embodiments, the antibody, or antigen-binding fragment thereof, of the invention comprises a VH chain that comprises one or more paratope residues selected from the group consisting of: Trp33 in CDR-H1, Tyr56 in CDR-H2, Tyr58 in CDR-H2, and Tyr97 in CDR-H3, according to Kabat numbering ("primary" paratope residues). In certain embodiments, the VH further comprises one or more paratope residues selected from the group consisting of: Asp54 in CDR-H2, Gln61 in CDR-H2, Gly98 in CDR-H3, and Leu100 in CDR-H3, according to Kabat numbering ("secondary" paratope residues). In certain embodiments, the antibody, or antigen-binding fragment thereof, of the invention comprises a VL that comprises one or more paratope residues selected from the group consisting of: Tyr32 in CDR-L1, Ile92 in CDR-L3, and Leu94 in CDR-L3, according to Kabat numbering ("primary" paratope residues). In certain embodiments, the VH further comprises one or more paratope residues selected from the group consisting of: Gln27 in CDR-L1, Asp28 in CDR-L1, Ile29 in CDR-L1, Gly30 in CDR-L1, and Ile93 in CDR-L3, according to Kabat numbering ("secondary" paratope residues). The antibody, or antigen binding fragment thereof, of the invention may also comprise any combination of the paratope residues disclosed herein.

In certain embodiments, the antibody, or antigen-binding fragment thereof, described herein comprises the following heavy chain CDR sequences: (i) a CDR-H1 sharing at least 90%, at least 91%, at least 92%, at least 93%, at least 94%, or at least 95% identical to SEQ ID NO: 37, a CDR-H2 sharing at least 90%, at least 91%, at least 92%, at least 93%, at least 94%, or at least 95% identity with SEQ ID NO: 38, and a CDR-H3 sharing at least 90%, at least 91%, at least 92%, at least 93%, at least 94%, or at least 95% identity with SEQ ID NO: 39; and/or (ii) the following light chain CDR sequences: a CDR-L1 sharing at least 90%, at least 91%, at least 92%, at least 93%, at least 94%, or at least 95% identity with SEQ ID NO: 34, a CDR-L2 sharing at least 90%, at least 91%, at least 92%, at least 93%, at least 94%, or at least 95% identity with SEQ ID NO: 35, and a CDR-L3 sharing at least 90%, at least 91%, at least 92%, at least 93%, at least 94%, or at least 95% identity with SEQ ID NO: 36. In certain embodiments, the amino acid differences, as compared to SEQ ID NOs. 37, 38, 39, 34, 35, and 36, respectively, are not one of the primary or secondary paratope residues as shown in Table 14.

In certain embodiments, no more than 10, no more than 9, no more than 8, no more than 7, no more than 6, no more than 5, no more than 4, no more than 3, no more than 3, no more than 2, or no more than one substitution is made in the sequence of CDR-L1, relative to SEQ ID NO. 34. In certain embodiments, no more than 6, no more than 5, no more than 4, no more than 3, no more than 3, no more than 2, or no more than one substitution is made in the sequence of CDR-L2, relative to SEQ ID NO. 35. In certain embodiments, no more than 8, no more than 7, no more than 6, no more than 5, no more than 4, no more than 3, no more than 3, no more than 2, or no more than one substitution is made in the sequence of CDR-L3, relative to SEQ ID NO. 36. In certain embodiments, no more than 9, no more than 8, no more than 7, no more than 6, no more than 5, no more than 4, no more than 3, no more than 3, no more than 2, or no more than one substitution is made in the sequence of CDR-H1, relative to SEQ ID NO. 37. In certain embodiments, no more than 16, no more than 15, no more than 14, no more than 13, no more than 12, no more than 11, no more than 10, no more than 9, no more than 8, no more than 7, no more than 6, no more than 5, no more than 4, no more than 3, no more than 3, no more than 2, or no more than one substitution is made in the sequence of CDR-H2, relative to SEQ ID NO. 38. In certain embodiments, no more than 9, no more than 8, no more than 7, no more than 6, no more than 5, no more than 4, no more than 3, no more than 3, no more than 2, or no more than one substitution is made in the sequence of CDR-H3, relative to SEQ ID NO. 39. In certain embodiments, the substitution does not change binding affinity ($K_D$) value by more than 3 orders of magnitude, more than 2 orders of magnitude, or 1 order of magnitude, as compared with the $K_D$ of the antibody, or antigen-binding fragment thereof, without the substitution. In certain embodiments, the substitution is not one of the primary or secondary paratope residues as shown in Table 14.

In certain embodiments, the substitution is a conservative substitution as provided by Table 1.

TABLE 1

Exemplary Conservative Substitutions

| Residue | Conservative substitution | Residue | Conservative substitution |
|---|---|---|---|
| Ala | Ser | Leu | Ile, Val |
| Arg | Lys | Lys | Arg, Gln |
| Asn | Gln; His | Met | Leu, Ile |

TABLE 1-continued

Exemplary Conservative Substitutions

| Residue | Conservative substitution | Residue | Conservative substitution |
|---------|---------------------------|---------|---------------------------|
| Asp | Glu | Phe | Met, Leu, Tyr |
| Cys | Ser | Ser | Thr; Gly |
| Gln | Asn | Thr | Ser, Val |
| Glu | Asp | Trp | Tyr |
| Gly | Pro | Tyr | Trp, Phe |
| His | Asn, Gln | Val | Ile, Leu |
| Ile | Leu, Val | Pro | — |

In certain embodiments, when an antibody is derived from a non-human species, such as a humanized antibody in which murine CDRs are grafted to a human framework, the substitution is human germline substitution in which a non-human CDR residue is replaced with the corresponding human germline residue. One benefit of such substitution is to increase the human amino acid content, and to reduce potential immunogenicity of an antibody derived from a non-human species. For example, if human germline DPK9 framework is used and the exemplary antibody CTI-AF1, then the alignment of the CDR-L1 of CTI-AF1 antibody and human germline DPK9 is as follows:

TABLE 2

| Position | 24 | 25 | 26 | 27 | 28 | 29 | 30 | 31 | 32 | 33 | 34 |
|----------|----|----|----|----|----|----|----|----|----|----|----|
| Human Germline DPK9 (SEQ ID NO: 46) | R | A | S | Q | S | I | S | S | Y | L | N |
| CTI-AF1 antibody (SEQ ID NO: 34) | R | T | S | Q | D | I | G | N | Y | L | N |

For positions 24, 26, 27, 29, 32, 33, and 34, the human germline residue and the corresponding CTI-AF1 residue are the same, and no substitution is needed at these positions. For positions 25, 28, 30, and 31 (in bold), the human germline residue and the corresponding CTI-AF1 murine residue are different. Murine residues of CTI-AF1 at these positions may be replaced with the corresponding human germline DPK9 residue to further increase the human amino acid residue content.

Methods and libraries for introducing human germline residues in antibody CDRs are described in detail in Townsend et al., *Augmented Binary Substitution: Single-pass CDR germlining and stabilization of therapeutic antibodies*, PNAS, vol. 112, 15354-15359 (2015), and United States Patent Application Number 2017-0073395 A1 (published Mar. 16, 2017) and are herein incorporated by reference in their entirety.

In certain embodiments, the antibody, or antigen-binding fragment thereof, described herein comprises a human framework sequence. For example, a heavy chain framework sequence can be derived from a human VH3 germline, a VH1 germline, a VH5 germline, or a VH4 germline sequence. Preferred human germline heavy chain frameworks are frameworks derived from VH1, VH3, or VH5 germline sequences. For example, VH frameworks from the following well-known germline sequences may be used: IGHV3-23, IGHV3-7, or IGHV1-69, where germline names are based on IMGT germline definition. Preferred human germline light chain frameworks are frameworks derived from VK or Vλ germline sequences. For example, VL frameworks from the following germlines may be used: IGKV1-39 or IGKV3-20, where germline names are based on IMGT germline definition. Alternatively or in addition, the framework sequence may be a human germline consensus framework sequence, such as the framework of human Vλ1 consensus sequence, VK1 consensus sequence, VK2 consensus sequence, VK3 consensus sequence, VH3 germline consensus sequence, VH1 germline consensus sequence, VH5 germline consensus sequence, or VH4 germline consensus sequence.

Sequences of human germline frameworks are available from various public databases, such as V-base, IMGT, NCBI, or Abysis.

In certain embodiments, the human germline VL framework is the framework of DPK9 (IMGT name: IGKV1-39), and one or more residues in CDR-L1, CDR-L2, and CDR-L3 of the antibody, or antigen-binding fragment thereof, of the invention may be substituted with the corresponding DPK9 germline residues as shown in Table 3 (SEQ ID NOs.:46, 47, 48).

TABLE 3

| SEQ ID | | Light Chain |
|--------|--|-------------|
| 46 | DPK9 CDR-L1 | RASQSISSYLN |
| 47 | DPK9 CDR-L2 | AASSLQS |
| 48 | DPK9 CDR-L3 | QQSYSTP |
| 49 | DPK12 CDR-L1 | KSSQSLLHSDGKTYLY |
| 50 | DPK12 CDR-L2 | EVSNRFS |
| 51 | DPK12 CDR-L3 | MQSIQLP |
| 52 | DPK18 CDR-L1 | RSSQSLVYSDGNTYLN |
| 53 | DPK18 CDR-L2 | KVSNRDS |
| 54 | DPK18 CDR-L3 | MQGTHWP |
| 55 | DPK24 CDR-L1 | KSSQSVLYSSNNKNYLA |
| 56 | DPK24 CDR-L2 | WASTRES |
| 57 | DPK24 CDR-L3 | QQYYSTP |
| 58 | HK102_V1 CDR-L1 | RASQSISSWLA |
| 59 | HK102_V1 CDR-L2 | DASSLES |
| 60 | HK102_V1 CDR-L3 | QQYNSYS |
| 61 | DPK1 CDR-L1 | QASQDISNYLN |
| 62 | DPK1 CDR-L2 | DASNLET |
| 63 | DPK1 CDR-L3 | QQYDNLP |
| 64 | DPK8 CDR-L1 | RASQGISSYLA |
| 65 | DPK8 CDR-L2 | AASTLQS |
| 66 | DPK8 CDR-L3 | QQLNSYP |
| 67 | DPK21 CDR-L1 | RASQSVSSNLA |
| 68 | DPK21 CDR-L2 | GASTRAT |
| 69 | DPK21 CDR-L3 | QQYNNWP |
| 70 | Vg_38K CDR-L1 | RASQSVSSYLA |
| 71 | Vg_38K CDR-L2 | DASNRAT |
| 72 | Vg_38K CDR-L3 | QQRSNWP |

TABLE 3-continued

| SEQ ID | | Light Chain |
|---|---|---|
| 73 | DPK22 CDR-L1 | RASQSVSSSYLA |
| 74 | DPK22 CDR-L2 | GASSRAT |
| 75 | DPK22 CDR-L3 | QQYGSSP |
| 76 | DPK15 CDR-L1 | RSSQSLLHSNGYNYLD |
| 77 | DPK15 CDR-L2 | LGSNRAS |
| 78 | DPK15 CDR-L3 | MQALQTP |
| 79 | DPL16 CDR-L1 | QGDSLRSYYAS |
| 80 | DPL16 CDR-L2 | GKNNRPS |
| 81 | DPL16 CDR-L3 | NSRDSSGNH |
| 82 | DPL8 CDR-L1 | TGSSSNIGAGYDVH |
| 83 | DPL8 CDR-L2 | GNSNRPS |
| 84 | DPL8 CDR-L3 | QSYDSSLSG |
| 85 | V1-22 CDR-L1 | TRSSGSIASNYVQ |
| 86 | V1-22 CDR-L2 | EDNQRPS |
| 87 | V1-22 CDR-L3 | QSYDSSN |
| 88 89 | Vλ consensus CDR-L1 | TGSSSGGSYYVS or TGSSSDVGGSYYVS |
| 90 91 | Vλ consensus CDR-L2 | ENDSNRPS or EDSNR(S/D)K(Q/G)QKPS |
| 92 93 | Vλ consensus CDR-L3 | QSWDSSA(N/T) or QSWDSSA(N/T)F(F/V)(G/V) |
| 94 95 | Vλ1 consensus CDR-L1 | SGSSSNIGNN(A/Y)V(N/H/S) or SGSSSNIIGNN(A/Y)V(N/H/S) |
| 96 | Vλ1 consensusCDR-L2 | GNN(K/N/Q)RPS |
| 97 | Vλ1 consensusCDR-L3 | AAWDDSL(N/S)G |
| 98 | Vλ3 consensusCDR-L1 | CSGD(A/V)LG(K/S)KYAH |
| 99 | Vλ3 consensusCDR-L2 | KDSERPS |
| 100 101 | Vλ3 consensusCDR-L3 | QSWDSSG(N/D/T/A) or QSWDSSG(N/D/T/A)H |
| 102 103 | Vκ consensus CDR-L1 | RASQSLLHSDGISSYLA or RASQGISSYLA |
| 104 | Vκ consensus CDR-L2 | AASSRAS |
| 105 | Vκ consensus CDR-L3 | QQYNSYP |
| 106 | Vκ1 consensus CDR-L1 | RASQGIS(N/S)YLA |
| 107 | Vκ1 consensus CDR-L2 | AASSLQS |
| 108 | Vκ1 consensus CDR-L3 | QQYNSYP |
| 109 110 | Vκ2 consensus CDR-L1 | RSSQSLLHSDGNTYLD or RSSQSLLHSDDGNTYLD |
| 111 | Vκ2 consensus CDR-L2 | (K/T)(V/I)SNR(A/F)S |
| 112 | Vκ2 consensus CDR-L3 | MQATQFP |
| 113 | Vκ3 consensus CDR-L1 | RASQS(S/V)(S/V)SSYLA |
| 114 | Vκ3 consensus CDR-L2 | GASTRAT |
| 115 | Vκ3 consensus CDR-L3 | QW(S/N/G/H)NWP |

In certain embodiments, the human germline VL framework is the framework of DPK12 (IMGT name: IGKV2D-29), and one or more residues in CDR-L1, CDR-L2, and CDR-L3 of the antibody, or antigen-binding fragment thereof, of the invention may be substituted with the corresponding DPK12 germline residues as shown in Table 3 (SEQ ID NOs.:49, 50, 51).

In certain embodiments, the human germline VL framework is the framework of DPK18 (IMGT name: IGKV2-30), and one or more residues in CDR-L1, CDR-L2, and CDR-L3 of the antibody, or antigen-binding fragment thereof, of the invention may be substituted with the corresponding DPK18 germline residues as shown in Table 3 (SEQ ID NOs.:52, 53, 54).

In certain embodiments, the human germline VL framework is the framework of DPK24 (IMGT name: IGKV4-1), and one or more residues in CDR-L1, CDR-L2, and CDR-L3 of the antibody, or antigen-binding fragment thereof, of the invention may be substituted with the corresponding DPK24 germline residues as shown in Table 3 (SEQ ID NOs.:55, 56, 57).

In certain embodiments, the human germline VL framework is the framework of HK102_V1 (IMGT name: IGKV1-5), and one or more residues in CDR-L1, CDR-L2, and CDR-L3 of the antibody, or antigen-binding fragment thereof, of the invention may be substituted with the corresponding HK102_V1 germline residues as shown in Table 3 (SEQ ID NOs.:58, 59, 60).

In certain embodiments, the human germline VL framework is the framework of DPK1 (IMGT name: IGKV1-33), and one or more residues in CDR-L1, CDR-L2, and CDR-L3 of the antibody, or antigen-binding fragment thereof, of the invention may be substituted with the corresponding DPK1 germline residues as shown in Table 3 (SEQ ID NOs.:61, 62, 63).

In certain embodiments, the human germline VL framework is the framework of DPK8 (IMGT name: IGKV1-9), and one or more residues in CDR-L1, CDR-L2, and CDR-L3 of the antibody, or antigen-binding fragment thereof, of the invention may be substituted with the corresponding DPK8 germline residues as shown in Table 3 (SEQ ID NOs.:64, 65, 66).

In certain embodiments, the human germline VL framework is the framework of DPK21 (IMGT name: IGKV3-15), and one or more residues in CDR-L1, CDR-L2, and CDR-L3 of the antibody, or antigen-binding fragment thereof, of the invention may be substituted with the corresponding DPK21 germline residues as shown in Table 3 (SEQ ID NOs.:67, 68, 69).

In certain embodiments, the human germline VL framework is the framework of Vg_38K (IMGT name: IGKV3-11), and one or more residues in CDR-L1, CDR-L2, and CDR-L3 of the antibody, or antigen-binding fragment thereof, of the invention may be substituted with the corresponding Vg_38K germline residues as shown in Table 3 (SEQ ID NOs.:70, 71, 72).

In certain embodiments, the human germline VL framework is the framework of DPK22 (IMGT name: IGKV3-20), and one or more residues in CDR-L1, CDR-L2, and CDR-L3 of the antibody, or antigen-binding fragment thereof, of the invention may be substituted with the corresponding DPK22 germline residues as shown in Table 3 (SEQ ID NOs.:73, 74, 75).

In certain embodiments, the human germline VL framework is the framework of DPK15 (IMGT name: IGKV2-28), and one or more residues in CDR-L1, CDR-L2, and CDR-L3 of the antibody, or antigen-binding fragment thereof, of the invention may be substituted with the corresponding DPK15 germline residues as shown in Table 3 (SEQ ID NOs.:76, 77, 78).

In certain embodiments, the human germline VL framework is the framework of DPL16 (IMGT name: IGLV3-19), and one or more residues in CDR-L1, CDR-L2, and CDR-L3 of the antibody, or antigen-binding fragment thereof, of the invention may be substituted with the corresponding DPL16 germline residues as shown in Table 3 (SEQ ID NOs.:79, 80, 81).

In certain embodiments, the human germline VL framework is the framework of DPL8 (IMGT name: IGLV1-40), and one or more residues in CDR-L1, CDR-L2, and CDR-L3 of the antibody, or antigen-binding fragment thereof, of the invention may be substituted with the corresponding DPL8 germline residues as shown in Table 3 (SEQ ID NOs.:82, 83, 84).

In certain embodiments, the human germline VL framework is the framework of V1-22 (IMGT name: IGLV6-57), and one or more residues in CDR-L1, CDR-L2, and CDR-L3 of the antibody, or antigen-binding fragment thereof, of the invention may be substituted with the corresponding V1-22 germline residues as shown in Table 3 (SEQ ID NOs.:85, 86, 87).

In certain embodiments, the human germline VL framework is the framework of human Vλ, consensus sequence, and one or more residues in CDR-L1, CDR-L2, and CDR-L3 of the antibody, or antigen-binding fragment thereof, of the invention may be substituted with the corresponding Vλ, germline consensus residues as shown in Table 3 (SEQ ID NOs.:88, 89, 90, 91, 92, 93). Alternative sequences are provided for the consensus sequence with and without gaps. At positions where there is no consensus, residues within parenthesis ( ) are those that are tied for the most frequent residues present in human antibodies.

In certain embodiments, the human germline VL framework is the framework of human Vλ1 consensus sequence, and one or more residues in CDR-L1, CDR-L2, and CDR-L3 of the antibody, or antigen-binding fragment thereof, of the invention may be substituted with the corresponding Vλ1 germline consensus residues as shown in Table 3 (SEQ ID NOs.:94, 95, 96, 97) Alternative sequences are provided for the consensus sequence with and without gaps. At positions where there is no consensus, residues within parenthesis ( ) are those that are tied for the most frequent residues present in human antibodies.

In certain embodiments, the human germline VL framework is the framework of human Vλ3 consensus sequence, and one or more residues in CDR-L1, CDR-L2, and CDR-L3 of the antibody, or antigen-binding fragment thereof, of the invention may be substituted with the corresponding Vλ3 germline consensus residues as shown in Table 3 (SEQ ID NOs.: 98, 99, 100, 101). Alternative sequences are provided for the consensus sequence with and without gaps. At positions where there is no consensus, residues within parenthesis ( ) are those that are tied for the most frequent residues present in human antibodies.

In certain embodiments, the human germline VL framework is the framework of human Vκ consensus sequence and one or more residues in CDR-L1, CDR-L2, and CDR-L3 of the antibody, or antigen-binding fragment thereof, of the invention may be substituted with the corresponding Vκ germline consensus residues as shown in Table 3 (SEQ ID NOs.:102, 103, 104, 105). Alternative sequences are provided for the consensus sequence with and without gaps.

In certain embodiments, the human germline VL framework is the framework of human Vκ1 consensus sequence, and one or more residues in CDR-L1, CDR-L2, and CDR-L3 of the antibody, or antigen-binding fragment thereof, of the invention may be substituted with the corresponding Vκ1 germline consensus residues as shown in Table 3 (SEQ ID NOs.:106, 107, 108). At positions where there is no consensus, residues within parenthesis ( ) are those that are tied for the most frequent residues present in human antibodies.

In certain embodiments, the human germline VL framework is the framework of human Vκ2 consensus sequence, and one or more residues in CDR-L1, CDR-L2, and CDR-L3 of the antibody, or antigen-binding fragment thereof, of the invention may be substituted with the corresponding Vκ2 germline consensus residues as shown in Table 3 (SEQ ID NOs.:109, 110, 111, 112). Alternative sequences are provided for the consensus sequence with and without gaps. At positions where there is no consensus, residues within parenthesis ( ) are those that are tied for the most frequent residues present in human antibodies.

In certain embodiments, the human germline VL framework is the framework of human VK3 consensus sequence, and one or more residues in CDR-L1, CDR-L2, and CDR-L3 of the antibodies (and fragments) of the invention may be substituted with the corresponding germline residues as shown in Table 3 (SEQ ID NOs.:113, 114, 115). At positions where there is no consensus, residues within parenthesis ( ) are those that are tied for the most frequent residues present in human antibodies.

In certain embodiments, the human germline VH framework is the framework of DP54 (IMGT name: IGHV3-7), and one or more residues in CDR-H1 and CDR-H2 of the antibody, or antigen-binding fragment thereof, of the invention may be substituted with the corresponding germline residues as shown in Table 4 SEQ ID NOs.:116, 117).

TABLE 4

| SEQ ID | | | Heavy Chain |
|---|---|---|---|
| 116 | DP54 | CDR-H1 | GFTFSSYWMS |
| 117 | DP54 | CDR-H2 | ANIKQDGSEKYYVDSVKG |
| 118 | DP47 | CDR-H1 | GFTFSSYAMS |
| 119 | DP47 | CDR-H2 | AISGSGGSTYYADSVKG |
| 120 | DP71 | CDR-H1 | GGSISSYYWS |
| 121 | DP71 | CDR-H2 | GYIYYSGSTNYNPSLKS |
| 122 | DP75 | CDR-H1 | GYTFTGYYMH |
| 123 | DP75 | CDR-H2 | GWINPNSGGTNYAQKFQG |
| 124 | DP10 | CDR-H1 | GGTFSSYAIS |
| 125 | DP10 | CDR-H2 | GGIIPIFGTANYAQKFQG |
| 126 | DP7 | CDR-H1 | GYTGTSYYMH |

TABLE 4-continued

| SEQ ID | Heavy Chain | |
|---|---|---|
| 127 | DP7 CDR-H2 | GIINPSGGSTSYAQKFQG |
| 128 | DP49 CDR-H1 | GFTFSSYGMH |
| 129 | DP49 CDR-H2 | AVISYDGSNKYYADSVKG |
| 130 | DP51 CDR-H1 | GFTFSSYSMN |
| 131 | DP51 CDR-H2 | SYISSSSSTIYYADSVKG |
| 132 | DP38 CDR-H1 | GFTFSNAWMS |
| 133 | DP38 CDR-H2 | GRIKSKTDGGTTDYAAPVKG |
| 134 | DP79 CDR-H1 | GGSISSSSYYWG |
| 135 | DP79 CDR-H2 | GSIYYSGSTYYNPSLKS |
| 136 | DP78 CDR-H1 | GGSISSGDYYWS |
| 137 | DP78 CDR-H2 | GYIYYSGSTYYNPSLKS |
| 138 | DP73 CDR-H1 | GYSFTSYWIG |
| 139 | DP73 CDR-H2 | GIIYPGDSDTRYSPSFQG |
| 140 141 | VH consensus CDR-H1 | GFTFSSYAM(H/S) or GFTFSSYAM(H/S)WS |
| 142 143 | VH consensus CDR-H2 | GWISPNGGSTYYADSVKG or GWISPKANGGSTYYADSVKG |
| 144 | VH3 consensus CDR-H1 | GFTFSSYAMS |
| 145 146 | VH3 consensus CDR-H2 | SVISSDG(G/S)STYYADSVKG or SVISSKADG(G/S)STYYADSVKG |
| 147 | VH5 consensus CDR-H1 | GYSFTSYWI(S/G/H) |
| 148 | VH5 consensus CDR-H2 | G(R/I/S)IYPGDSDTRYSPSFQG |
| 149 | VH1 consensus CDR-H1 | GYTFTSY(A/Y)(I/M)H |
| 150 | VH1 consensus CDR-H2 | GWINP(G/Y)NGNTNYAQKFQ |
| 151 | VH4 consensus CDR-H1 | GGSISSG(N/Y)YYWS |
| 152 | VH4 consensus CDR-H2 | GYIYYSGSTYYNPSLKS |

In certain embodiments, the human germline VH framework is the framework of DP47 (IMGT name: IGHV3-23), and one or more residues in CDR-H1 and CDR-H2 of the antibody, or antigen-binding fragment thereof, of the invention may be substituted with the corresponding DP47 germline residues as shown in Table 4 (SEQ ID NOs.:118, 119).

In certain embodiments, the human germline VH framework is the framework of DP71 (IMGT name: IGHV4-59), and one or more residues in CDR-H1 and CDR-H2 of the antibody, or antigen-binding fragment thereof, of the invention may be substituted with the corresponding DP71 germline residues as shown in Table 4 (SEQ ID NOs.:120, 121).

In certain embodiments, the human germline VH framework is the framework of DP75 (IMGT name: IGHV1-2_02), and one or more residues in CDR-H1 and CDR-H2 of the antibody, or antigen-binding fragment thereof, of the invention may be substituted with the corresponding DP75 germline residues as shown in Table 4 (SEQ ID NOs.:122, 123).

In certain embodiments, the human germline VH framework is the framework of DP10 (IMGT name: IGHV1-69), and one or more residues in CDR-H1 and CDR-H2 of the antibody, or antigen-binding fragment thereof, of the invention may be substituted with the corresponding DP10 germline residues as shown in Table 4 (SEQ ID NOs.:124, 125).

In certain embodiments, the human germline VH framework is the framework of DP7 (IMGT name: IGHV1-46), and one or more residues in CDR-H1 and CDR-H2 of the antibody, or antigen-binding fragment thereof, of the invention may be substituted with the corresponding DP7 germline residues as shown in Table 4 (SEQ ID NOs.:126, 127).

In certain embodiments, the human germline VH framework is the framework of DP49 (IMGT name: IGHV3-30), and one or more residues in CDR-H1 and CDR-H2 of the antibody, or antigen-binding fragment thereof, of the invention may be substituted with the corresponding DP49 germline residues as shown in Table 4 (SEQ ID NOs.:128, 129).

In certain embodiments, the human germline VH framework is the framework of DP51 (IMGT name: IGHV3-48), and one or more residues in CDR-H1 and CDR-H2 of the antibody, or antigen-binding fragment thereof, of the invention may be substituted with the corresponding DP51 germline residues as shown in Table 4 (SEQ ID NOs.:130, 131).

In certain embodiments, the human germline VH framework is the framework of DP38 (IMGT name: IGHV3-15), and one or more residues in CDR-H1 and CDR-H2 of the antibody, or antigen-binding fragment thereof, of the invention may be substituted with the corresponding DP38 germline residues as shown in Table 4 (SEQ ID NOs.:132, 133).

In certain embodiments, the human germline VH framework is the framework of DP79 (IMGT name: IGHV4-39), and one or more residues in CDR-H1 and CDR-H2 of the antibody, or antigen-binding fragment thereof, of the invention may be substituted with the corresponding DP79 germline residues as shown in Table 4 (SEQ ID NOs.:134, 135).

In certain embodiments, the human germline VH framework is the framework of DP78 (IMGT name: IGHV4-30-4), and one or more residues in CDR-H1 and CDR-H2 of the antibody, or antigen-binding fragment thereof, of the invention may be substituted with the corresponding DP78 germline residues as shown in Table 4 (SEQ ID NOs.:136, 137).

In certain embodiments, the human germline VH framework is the framework of DP73 (IMGT name: IGHV5-51), and one or more residues in CDR-H1 and CDR-H2 of the antibody, or antigen-binding fragment thereof, of the invention may be substituted with the corresponding DP73 germline residues as shown in Table 4 (SEQ ID NOs.:138, 139).

In certain embodiments, the human germline VH framework is the framework of human VH germline consensus sequence, and one or more residues in CDR-H1 and CDR-H2 of the antibody, or antigen-binding fragment thereof, of the invention may be substituted with the corresponding VH germline consensus residues as shown in Table 4 (SEQ ID NOs.:140, 141, 142, 143). Alternative sequences are provided for the consensus sequence with and without gaps. At positions where there is no consensus, residues within parenthesis ( ) are those that are tied for the most frequent residues present in human antibodies.

In certain embodiments, the human germline VH framework is the framework of human VH3 germline consensus sequence, and r one or more residues in CDR-H1 and CDR-H2 of the antibody, or antigen-binding fragment thereof, of the invention may be substituted with the corresponding VH3 germline consensus residues as shown in Table 4 (SEQ ID NOs.:144, 145, 146). Alternative sequences are provided for the consensus sequence with and without consensus, residues within parenthesis ( ) are those that are tied for the most frequent residues present in human antibodies.

In certain embodiments, the human germline VH framework is the framework of human VH5 germline consensus sequence, and one or more residues in CDR-H1 and CDR-H2 of the antibody, or antigen-binding fragment thereof, of the invention may be substituted with the corresponding VH5 germline consensus residues as shown in Table 4 (SEQ ID NOs.:147, 148). At positions where there is no consensus, residues within parenthesis ( ) are those that are tied for the most frequent residues present in human antibodies.

In certain embodiments, the human germline VH framework is the framework of human VH1 germline consensus sequence, and one or more residues in CDR-H1 and CDR-H2 of the antibody, or antigen-binding fragment thereof, of the invention may be substituted with the corresponding VH1 germline consensus residues as shown in Table 4 (SEQ ID NOs.:149, 150). At positions where there is no consensus, residues within parenthesis ( ) are those that are tied for the most frequent residues present in human antibodies.

In certain embodiments, the human germline VH framework is the framework of human VH4 germline consensus sequence, and one or more residues in CDR-H1 and CDR-H2 of the antibody, or antigen-binding fragment thereof, of the invention may be substituted with the corresponding VH4 germline consensus residues as shown in Table 4 (SEQ ID NOs.:151, 152). At positions where there is no consensus, residues within parenthesis ( ) are those that are tied for the most frequent residues present in human antibodies.

In certain embodiments, the antibody, or antigen-binding fragment thereof, of the invention comprises (numbering according to Kabat):
  (i) a VH that comprises: (a) a CDR-H1 comprising Trp33, and three or fewer amino acid differences as compared to SEQ ID NO: 37, (b) a CDR-H2 comprising Asp54, Tyr56, Tyr58, and Gln61, and three or fewer amino acid differences as compared to ID NO: 38; and (c) a CDR-H3 comprising Tyr97, Gly98, and Leu100; and three or fewer amino acid differences as compared to SEQ ID NO: 39; and
  (ii) a VL that comprises: (a) a CDR-L1 comprising Gln27, Asp28, Ile29, Gly30, Tyr32; and three or fewer amino acid differences as compared to SEQ ID NO: 34, (b) a CDR-L2 comprising a sequence that comprises three or fewer amino acid differences as compared to SEQ ID NO: 35; and (c) a CDR-L3 comprising Ile92, Ile93, and Leu94; and three or fewer amino acid differences as compared to of SEQ ID NO: 36.

In certain embodiments, the amino acid differences in CDR-H1, CDR-H2, CDR-L1, CDR-L2, and CDR-L3 are human germline substitutions in which a non-human CDR residue is replaced with a corresponding human germline residue (such as those human germline residues as shown in Tables 3 and 4).

In certain embodiments, the antibody or antigen-binding fragment thereof described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 28, and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 1. Any combination of these VL and VH sequences is also encompassed by the invention.

In certain embodiments, the VH framework is DP10. Other similar framework regions are also predicted to deliver advantageous antibodies or antibody fragments of the invention comprising CDRs of SEQ ID NOs. 37, 38, and 39 include: DP-88, DP-25, DP-73, IGHV5-10-1*01, IGHV5-10-1*04, DP-14, DP-75, DP15, DP-8, DP-7 and IGHV7-4-1*02, which share 99%, 93%, 75%, 73%, 73%, 92%, 90%, 90%, 89%, 93%, and 79% sequence identity, respectively, with the FW region of DP10, and comprise four or fewer amino acid differences in the common structural features: (A) residues directly underneath CDR (Vernier Zone), H2, H47, H48, and H49, H67, H69, H71, H73, H93, H94; (B) VH/VL chain packing residues: H37, H39, H45, H47, H91, H93; and (C) canonical CDR Structural support residues H24, H71, H94 (all Kabat numbering). Particularly preferred are framework regions of DP-88, DP-25, DP-73, IGHV5-10-1*01, and IGFV-10-1*04, sharing 99%, 93%, 75%, 73%, and 73% sequence identity with DP10, respectively, and have two or fewer amino acid differences in these common structural features.

In certain embodiments, the VL framework is DPK9. Other similar framework regions are also predicted to deliver advantageous antibodies of the invention comprising CDRs of SEQ ID NOs. 34, 35, and 36 include: DPK5, DPK4, DPK1, IGKV1-5*01, DPK24, DPK21, DPK15, IGKV1-13*02, IGKV1-17*01, DPK8, IGKV3-11*01, and DPK22, which share 99%, 97%, 97%, 96%, 80%, 76%, 66%, 97%, 97%, 96%, 76%, and 74% sequence identity, respectively, with the FW region of DPK-9, and comprise one or fewer amino acid difference in common structural features: (A) residues directly underneath CDR (Vernier Zone), L2, L4, L35, L36, L46, L47, L48, L49, L64, L66, L68, L69, L71; (B) VH/VL Chain packing Residues: L36, L38, L44, L46, L87; and (C) canonical CDR Structural support residues L2, L48, L64, L71 (all Kabat numbering). Particularly preferred are framework regions of DPK5, DPK4, DPK1, IGKV1-5*01, DPK24, DPK21, and DPK15, which share 99%, 97%, 97%, 96%, 80%, 76%, and 66% sequence identity with DPK9, respectively, and have no amino acid difference in these common structural features.

In certain embodiments, the antibody or antigen-binding fragment thereof described herein comprises (i) a CDR-H1 comprising SEQ ID NO:37, a CDR-H2 comprising SEQ ID NO:38, a CDR-H3 comprising SEQ ID NO:39, a CDR-L1 comprising SEQ ID NO:34; a CDR-L2 comprising SEQ ID NO:35, and a CDR-L3 comprising SEQ ID NO:36; and (ii) a VL framework comprising a sequence that is at least 66%, at least 74%, at least 76%, at least 80%, at least 96%, at least 97%, or at least 99% identical to the framework sequence of human germline DPK9, and a VH framework comprising a sequence that is at least 73%, at least 75%, at least 79%, at least 89%, at least 90%, at least 92%, at least 93%, or at least 99% identical to the framework sequence of human germline DP10.

In certain embodiments, the antibody or antigen-binding fragment thereof described herein comprises (i) a CH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 29; and/or (ii) a CL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 30. Any combination of these CH and CL sequences is also encompassed by the invention.

In certain embodiments, the antibody or antigen-binding fragment thereof described herein comprises an Fc domain. The Fc domain can be derived from IgA (e.g., $IgA_1$ or $IgA_2$), IgG, IgE, or IgG (e.g., $IgG_1$, $IgG_2$, $IgG_3$, or $IgG_4$).

In certain embodiments, the antibody or antigen-binding fragment thereof described herein comprises (i) a heavy chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 33, and/or (ii) a light chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 32. Any combination of these heavy chain and light chain sequences is also encompassed by the invention.

Additional antibodies (e.g., CTI-AF2 through CTI-AF27), antigen-binding fragments thereof, and antigen-binding variants thereof, are also provided by the invention. CTI-AF2 to CTI-AF27 share the same VH sequence but have different VL sequences. Accordingly, in certain embodiments, the antibody, or antigen-binding fragment thereof, of the invention comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 28, and/or (ii) a VL comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to any of SEQ ID NOs: 2-27. Any combination of these VL and VH sequences is also encompassed by the invention.

Also provided by the invention is an antibody, or antigen-binding fragment thereof, that competes for binding to human IFNβ with any of the antibody or antigen-binding fragment thereof described herein, such as any one of the antibodies listed in Table 11, or antigen-binding fragments thereof. For example, if the binding of an antibody, or an antigen-binding portion thereof, to human IFNβ reduces the subsequent binding to human IFNβ by CTI-AF1, the antibody, or an antigen-binding portion thereof, is deemed as competing with CTI-AF1 for human IFNβ binding.

Also provided by the invention is an antibody, or antigen-binding fragment thereof, that binds the same epitope of human IFNβ as any antibody, or antigen-binding fragment thereof, described herein, such as any antibody listed in Table 11, or antigen-binding fragments thereof. For example, an antibody competition assay (and overlapping epitope analysis) can be assessed using SPR, as described in detail herein, or any art-recognized competitive binding assay. The SPR binding assay described herein is the preferred, not exclusive method for assessing binding of the antibody of the invention, and any other test antibodies.

The antibodies, and antigen-binding fragments thereof, of the invention include monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody portion, domain antibodies (dAbs), humanized antibodies, and any other configuration of the immunoglobulin molecule that comprises an antigen recognition site of the required specificity, including glycosylation variants of antibodies, amino acid sequence variants of antibodies, and covalently modified antibodies. The antibodies and antigen-binding fragments may be murine, rat, human, or any other origin (including chimeric or humanized antibodies). In some embodiments, the antibody is a monoclonal antibody. In some embodiments, the antibody is a chimeric, humanized or human antibody. In certain embodiments, the antibody is a fully human antibody. In certain embodiments, the antibody is a humanized antibody.

The binding affinity of an antibody can be expressed as a $K_D$ value, which refers to the dissociation rate of a particular antigen-antibody interaction. $K_D$ is the ratio of the rate of dissociation, also called the "off-rate ($k_{off}$)", to the association rate, or "on-rate ($k_{on}$)". Thus, $K_D$ equals $k_{off}/k_{on}$ (dissociation/association) and is expressed as a molar concentration (M), and the smaller the $K_D$, the stronger the affinity of binding. $K_D$ values for antibodies can be determined using methods well established in the art. Unless otherwise specified, "binding affinity" refers to monovalent interactions (intrinsic activity; e.g., binding of an antibody to an antigen through a monovalent interaction).

In certain embodiments, the antibody, or antigen-binding fragment thereof, of the invention has an affinity ($K_D$) value of not more than about $1\times10^{-7}$ M, such as not more than about $1\times10^{-7}$ M, not more than about $9\times10^{-8}$ M, not more than about $8\times10^{-8}$ M, not more than about $7\times10^{-8}$ M, not more than about $6\times10^{-8}$ M, not more than about $5\times10^{-8}$ M, not more than about $4\times10^{-8}$ M, not more than about $3\times10^{-8}$ M, not more than about $2\times10^{-8}$ M, not more than about $1\times10^{-8}$ M, not more than about $9\times10^{-9}$ M, not more than about $8\times10^{-9}$ M, not more than about $7\times10^{-9}$ M, not more than about $6\times10^{-9}$ M, not more than about $5\times10^{-9}$ M, not more than about $4\times10^{-9}$ M, not more than about $3\times10^{-9}$ M, not more than about $2\times10^{-9}$ M, not more than about $1\times10^{-9}$ M, not more than about $9\times10^{-10}$ M, not more than about $8\times10^{-10}$ M, not more than about $7\times10^{-10}$ M, not more than about $6\times10^{-10}$ M, not more than about $5\times10^{-10}$ M, not more than about $4\times10^{-10}$ M, not more than about $3\times10^{-10}$ M, not more than about $2\times10^{-10}$ M, not more than about $1\times10^{-10}$ M, not more than about $9\times10^{-11}$ M, not more than about $8\times10^{-11}$ M, not more than about $7\times10^{-11}$ M, not more than about $6\times10^{-11}$ M, not more than about $5\times10^{-11}$ M, not more than about $4\times10^{-11}$ M, not more than about $3\times10^{-11}$ M, not more than about $2\times10^{-11}$ M, not more than about $1\times10^{-11}$ M, not more than about $9\times10^{-12}$ M, not more than about $8\times10^{-12}$ M, not more than about $7\times10^{-12}$ M, not more than about $6\times10^{-12}$ M, not more than about $5\times10^{-12}$ M, not more than about $4\times10^{-12}$ M, not more than about $3\times10^{-12}$ M, not more than about $2\times10^{-12}$ M, not more than about $1\times10^{-12}$ M, not more than about $9\times10^{-13}$ M, not more than about $8\times10^{-13}$ M, not more than about $7\times10^{-13}$ M, not more than about $6\times10^{-13}$ M, not more than about $5\times10^{-13}$ M, not more than about $4\times10^{-13}$ M, not more than about $3\times10^{-13}$ M, not more than about $2\times10^{-13}$ M, not more than about $1\times10^{-13}$ M, from about $1\times10^{-7}$ M to about $1\times10^{-14}$ M, from about $9\times10^{-8}$ M to about $1\times10^{-14}$ M, from about $8\times10^{-8}$ M to about $1\times10^{-14}$ M, from about $7\times10^{-8}$ M to about $1\times10^{-14}$ M, from about $6\times10^{-8}$ M to about $1\times10^{-14}$ M, from about $5\times10^{-8}$ M to about $1\times10^{-14}$ M, from about $4\times10^{-8}$ M to about $1\times10^{-14}$ M, from about $3\times10^{-8}$ M to about $1\times10^{-14}$ M, from about $2\times10^{-8}$ M to about $1\times10^{-14}$ M, from about $1\times10^{-8}$ M to about $1\times10^{-14}$ M, from about $9\times10^{-9}$ M to about $1\times10^{-14}$ M, from about $8\times10^{-9}$ M to about $1\times10^{-14}$ M, from about $7\times10^{-9}$ M to about $1\times10^{-14}$ M, from about $6\times10^{-9}$ M to about $1\times10^{-14}$ M, from about $5\times10^{-9}$ M to about $1\times10^{-14}$ M, from about $4\times10^{-9}$ M to about $1\times10^{-14}$ M, from about $3\times10^{-9}$ M to about $1\times10^{-14}$ M, from about $2\times10^{-9}$ M to about $1\times10^{-14}$ M, from about $1\times10^{-9}$ M to about $1\times10^{-14}$ M, from about $1\times10^{-7}$ M to about $1\times10^{-13}$ M, from about $9\times10^{-8}$ M to about $1\times10^{-13}$ M, from about $8\times10^{-8}$ M to about $1\times10^{-13}$ M, from about $7\times10^{-8}$ M to about $1\times10^{-13}$ M, from about $6\times10^{-8}$ M to about $1\times10^{-13}$ M, from about $5\times10^{-8}$ M to about $1\times10^{-13}$ M, from about $4\times10^{-8}$ M to about $1\times10^{-13}$ M, from about $3\times10^{-8}$ M to about $1\times10^{-13}$ M, from about $2\times10^{-8}$ M to about $1\times10^{-13}$ M, from about $1\times10^{-8}$ M to about $1\times10^{-13}$ M, from about $9\times10^{-9}$ M to about $1\times10^{-13}$ M, from about $8\times10^{-9}$ M to about $1\times10^{-13}$ M, from about $7\times10^{-9}$ M to about $1\times10^{-13}$ M, from about $6\times10^{-9}$ M to about $1\times10^{-13}$ M, from about $5\times10^{-9}$ M to about $1\times10^{-13}$ M, from about $4\times10^{-9}$ M to about $1\times10^{-13}$ M, from about $3\times10^{-9}$ M to about $1\times10^{-13}$ M, from about $2\times10^{-9}$ M to about $1\times10^{-13}$ M, or from about $1\times10^{-9}$ M to about $1\times10^{-13}$ M.

The value of $K_D$ can be determined directly by well-known methods, and can be computed even for complex mixtures by methods such as those, for example, set forth in Caceci et al. (1984, Byte 9: 340-362). For example, the $K_D$ may be established using a double-filter nitrocellulose filter binding assay such as that disclosed by Wong & Lohman (1993, Proc. Natl. Acad. Sci. USA 90: 5428-5432). Other standard assays to evaluate the binding ability of ligands such as antibodies towards target antigens are known in the art, including for example, ELISAs, Western blots, RIAs, and flow cytometry analysis, and other assays exemplified elsewhere herein.

One exemplary method for measuring binding affinity ($K_D$) value is surface plasmon resonance (SPR), typically using a biosensor system such as a BIACORE® system. SPR refers to an optical phenomenon that allows for the analysis of real-time biospecific interactions by detection of alterations in protein concentrations within a biosensor matrix, for example using the BIACORE® system. BIAcore kinetic analysis comprises analyzing the binding and dissociation of an antigen from a chip with an immobilized molecule (e.g., a molecule comprising an antigen-binding domain), on their surface; or the dissociation of an antibody, or antigen-binding fragment thereof, from a chip with an immobilized antigen.

In certain embodiments, the SPR measurement is conducted using a BIACORE® T100 or T200 instrument. For example, a standard assay condition for surface plasmon resonance can be based on antibody immobilization of approximately 100-500 Response Units (RU) of IgG on the SPR chip. Purified target proteins are diluted in buffer to a range of final concentrations and injected at a requisite flow rate (e.g. 10-100 µl/min) to allow the calculation of Ka. Dissociation is allowed to proceed to establish off-rate, followed by 3 M $MgCl_2$ (or 20 mM NaOH) for regeneration of the chip surface. Sensorgrams are then analyzed using a kinetics evaluation software package. In an exemplary embodiment, the SPR assay is according to the conditions as set forth in Example 1.

In certain embodiments, the binding affinity ($K_D$) value is measured using solution-based kinetic exclusion assay (KinExA™). In a particular embodiment, the KinExA measurement is conducted using a KinExA™ 3200 instrument (Sapidyne). The Kinetic Exclusion Assay (KinExA™) is a general purpose immunoassay platform (basically a flow spectrofluorimeter) that is capable of measuring equilibrium dissociation constants, and association and dissociation rate constants for antigen/antibody interactions. Since KinExA™ is performed after equilibrium has been obtained it is an advantageous technique to use for measuring the $K_D$ of high affinity interactions where the off-rate of the interaction may be very slow. The KinExA™ methodology can be conducted generally as described in Drake et al (2004) Analytical Biochemistry 328, 35-43.

Another method for determining the $K_D$ of an antibody is by using Bio-Layer Interferometry, typically using OCTET® technology (Octet QKe system, ForteBio).

In general, an anti-IFNβ antibody should bind to IFNβ with high affinity, in order to effectively block the activities of IFNβ. IFNβ binds IFNAR1 at a $K_D$ of about 50 nM, and to IFNAR2 at a $K_D$ of about 100 µM. Accordingly, it is desirable that the IFNβ antibody have binding affinities ($K_D$) in nanomolar and picomolar range, such as about $1\times10^{-9}$ M or lower.

Activity Assays

In certain embodiments, the antibody, or antigen-binding fragment thereof, of the invention is a neutralizing antibody that reduces at least one activity of IFNβ. Such activity of IFNβ includes, but it not limited to, binding to IFNAR, increasing expression of an IFNβ-dependent gene, and/or inducing phosphorylation of, e.g., STAT1, and/or STAT2, among other IFNβ activities known in the art. Whether an antibody, or antigen-binding fragment thereof, reduces an activity of IFNβ can be assessed by a number of assays. For example, assays can be used to determine whether the antibody, or antigen-binding fragment thereof: (a) inhibits the binding of IFNβ to IFNAR; (b) reduces the expression level of an IFNβ-dependent gene; and/or (c) inhibit IFNβ-induced phosphorylation, such as phosphorylation of STAT1, and/or STAT2.

In certain embodiments, the antibody, or antigen-binding fragment thereof, inhibits the binding of IFNβ to IFNAR (e.g., can be assessed by competitive binding to IFNβ). For example, an assay may compare (i) the binding of IFNβ to IFNAR in the presence of the antibody, or antigen-binding fragment thereof, with (ii) the binding of IFNβ to IFNAR in the absence of the antibody, or antigen-binding fragment thereof. The reduction in binding of IFNβ to IFNAR can be at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%, in the presence of the anti-IFNβ antibody, or antigen-binding fragment thereof. The expected binding of IFNβ to IFNAR in the absence of the antibody, or antigen-binding fragment thereof, can be set as 100%.

In certain embodiments, the antibody, or antigen-binding fragment thereof, inhibits the binding of IFNβ to IFNAR, with a half maximal inhibitory concentration ($IC_{50}$) of not more than about $1\times10^{-7}$ M, not more than about $1\times10^{-8}$ M, not more than about $1\times10^{-9}$ M, not more than about $1\times10^{-10}$ M, not more than about $1\times10^{-11}$ M, not more than about $1\times10^{-12}$ M, not more than about $1\times10^{-13}$ M, not more than about $1\times10^{-14}$ M, not more than about $1\times10^{-15}$ M, from about $1\times10^{-7}$ M to about $5\times10^{-14}$ M, from about $1\times10^{-7}$ M to about $1\times10^{-14}$ M, from about $1\times10^{-7}$ M to about $5\times10^{-13}$ M, from about $1\times10^{-7}$ M to about $1\times10^{-13}$ M, from about $1\times10^{-7}$ M to about $5\times10^{-12}$ M, or from about $1\times10^{-7}$ M to about $1\times10^{-12}$ M.

The activities of an antibody, or antigen-binding fragment thereof, of the invention can also be assessed by measuring the expression level of an IFNβ-dependent gene. For example, the gene can be a downstream component in the IFNβ-mediated signal pathway (such as CMPK2, IFIT1, IF127, IFIH1, IF144, IF144L, IF16, ISG15, LY6E, HERC5, MX1, OAS1, OAS2, OAS3, RSAD2, XAF1, CXCL10, or any combination thereof). Alternatively, the gene can be a reporter gene (e.g., the luciferase reporter gene as used in the examples) where the expression level of the reporter gene correlates with IFNβ activity (e.g., the reporter gene is operably linked to an IFNβ-dependent response element). The expression level of the downstream gene or reporter gene can be assessed by a variety of methods, such as measuring the RNA level, protein level, or activity level of a protein. The assay can compare (i) the expression level of the IFNβ dependent gene in the presence of the antibody, or antigen-binding fragment thereof, with (ii) the expression level of the IFNβ dependent gene in the absence of the antibody, or antigen-binding fragment thereof. The reduction in expression level of a downstream gene or reporter gene can be at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%, in the presence of the anti-IFNβ antibody, or antigen-binding fragment thereof. The baseline expression level in the absence of the antibody, or antigen-binding fragment thereof, can be set as 100%.

In certain embodiments, the antibody, or antigen-binding fragment thereof, inhibits the expression of an IFNβ-dependent gene, with a half maximal inhibitory concentration ($IC_{50}$) of not more than about $1 \times 10^{-7}$ M, not more than about $1 \times 10^{-8}$ M, not more than about $1 \times 10^{-9}$ M, not more than about $1 \times 10^{-10}$ M, not more than about $1 \times 10^{-11}$ M, not more than about $1 \times 10^{-12}$ M, not more than about $1 \times 10^{-13}$ M, not more than about $1 \times 10^{-14}$ M, not more than about $1 \times 10^{-15}$ M, from about $1 \times 10^{-7}$ M to about $5 \times 10^{-14}$ M, from about $1 \times 10^{-7}$ M to about $1 \times 10^{-14}$ M, from about $1 \times 10^{-7}$ M to about $5 \times 10^{-13}$ M, from about $1 \times 10^{-7}$ M to about $1 \times 10^{-13}$ M, from about $1 \times 10^{-7}$ M to about $5 \times 10^{-12}$ M, or from about $1 \times 10^{-7}$ M to about $1 \times 10^{-12}$ M. In certain embodiments, $IC_{50}$ of from about $1 \times 10^{-10}$ M to about $1 \times 10^{-13}$ M is preferred. In certain embodiments, $IC_{50}$ of from about $5 \times 10^{-11}$ M to about $5 \times 10^{-12}$ M is preferred.

The inhibitory activity of an antibody, or antigen-binding fragment thereof, can also be assessed by measuring the level of IFNβ-induced phosphorylation, such as STAT1 phosphorylation, and/or STAT2 phosphorylation level. The assay can compare (i) the phosphorylation level of STAT1 and/or STAT2 in the presence of the antibody, or antigen-binding fragment thereof, with (ii) the phosphorylation level of STAT1 and/or STAT2 in the absence of the antibody, or antigen-binding fragment thereof. The reduction in phosphorylation level can be at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%, in the presence of the anti-IFNβ antibody, or antigen-binding fragment thereof. The baseline STAT1 phosphorylation and/or STAT2 phosphorylation level in the absence of the antibody, or antigen-binding fragment thereof, can be set as 100%.

In certain embodiments, the antibody, or antigen-binding fragment thereof, inhibits IFNβ-induced phosphorylation (such as STAT1 phosphorylation, and/or STAT2 phosphorylation), with a half maximal inhibitory concentration ($IC_{50}$) of not more than about $1 \times 10^{-7}$ M, not more than about $1 \times 10^{-8}$ M, not CTI-AF15, CTI-AF16, CTI-AF17, CTI-AF18, CTI-AF19, CTI-AF20, CTI-AF21, CTI-AF22, CTI-AF23, CTI-AF24, CTI-AF25, CTI-AF26, and CTI-AF27.

The invention also provides polynucleotides comprising a sequence encoding a protein comprising the amino acid sequence selected from the group consisting of: (i) SEQ ID NOs:1-27, (ii) SEQ ID NO:28, and (iii) any combination thereof.

The invention also provides polynucleotides comprising the nucleic acid sequence set forth as SEQ ID NOs: 166 or 167.

The invention also provides polynucleotides comprising the nucleic acid sequence of the DNA insert of the plasmid deposited with the ATCC and having Accession No. PTA-122727 or the DNA insert of the plasmid deposited with the ATCC and having Accession No. PTA-122726.

In another aspect, the invention provides polynucleotides and variants thereof encoding an anti-IFNβ antibody, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific nucleic acid sequences disclosed herein. These amounts are not meant to be limiting, and increments between the recited percentages are specifically envisioned as part of the disclosure.

In one embodiment, the VH and VL domains, or antigen-binding portion thereof, or full length HC or LC, are encoded by separate polynucleotides. Alternatively, both VH and VL, or antigen-binding portion thereof, or HC and LC, are encoded by a single polynucleotide.

Polynucleotides complementary to any such sequences are also encompassed by the present disclosure. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. In some embodiments, variants exhibit at least about 70% identity, in some embodiments, at least about 80% identity, in some embodiments, at least about 90% identity, and in some embodiments, at least about 95% identity to a polynucleotide sequence that encodes a native antibody or a portion thereof. These amounts are not meant to be limiting, and increments between the recited percentages are specifically envisioned as part of the disclosure.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, WI), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730.

In some embodiments, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present disclosure. Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, for example.

Suitable cloning and expression vectors can include a variety of components, such as promoter, enhancer, and other transcriptional regulatory sequences. The vector may also be constructed to allow for subsequent cloning of an antibody variable domain into different vectors.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, μMB9, ColE1, pCR1, RP4, phage DNAs, and shuttle vectors such as pSA3 and pAT28. These and many other cloning vectors are available from commercial vendors such as BioRad, Stratgene, and Invitrogen.

Expression vectors are further provided. Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest and/or the polynucleotides themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The antibody, or antigen-binding fragment thereof, may be made recombinantly using a suitable host cell. A nucleic acid encoding the antibody or antigen-binding fragment thereof can be cloned into an expression vector, which can then be introduced into a host cell, such as E. coli cell, a yeast cell, an insect cell, a simian COS cell, a Chinese hamster ovary (CHO) cell, or a myeloma cell where the cell does not otherwise produce an immunoglobulin protein, to obtain the synthesis of an antibody in the recombinant host cell. Preferred host cells include a CHO cell, a Human embryonic kidney (HEK) 293 cell, or an Sp2.0 cell, among many cells well-known in the art.

An antibody fragment can be produced by proteolytic or other degradation of a full-length antibody, by recombinant methods, or by chemical synthesis. A polypeptide fragment of an antibody, especially shorter polypeptides up to about 50 amino acids, can be conveniently made by chemical synthesis. Methods of chemical synthesis for proteins and peptides are known in the art and are commercially available.

The antibody, or antigen-binding fragment thereof, of the invention may be affinity matured. For example, an affinity matured antibody can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and WO2004/058184).

2. Formulations and Uses

The antibody, or antigen-binding fragment thereof, of the invention can be formulated as a pharmaceutical composition. The pharmaceutical composition may further comprise a pharmaceutically acceptable carrier, excipient, and/or stabilizer (Remington: The Science and practice of Pharmacy 20th Ed., 2000, Lippincott Williams and Wilkins, Ed. K. E. Hoover), in the form of lyophilized formulation or aqueous solution. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutically acceptable excipients are further described herein.

The antibody, or antigen-binding fragment thereof, of the invention can be used for various therapeutic or diagnostic purposes. For example, the antibody, or antigen-binding fragment thereof, of the invention may be used as an affinity purification agents (e.g., for in vitro purification of IFNβ), as a diagnostic agent (e.g., for detecting expression of IFNβ in specific cells, tissues, or serum).

Exemplary therapeutic uses of the antibody, or antigen-binding fragment thereof, of the invention include treating a rheumatic disease (such as SLE or DM) or an interferonopathy. The antibody, or antigen-binding fragment thereof, of the invention may also be used in prophylactic treatment (e.g., administering to a subject who has not exhibited a disease symptom but is susceptible to a rheumatic disease or an interferonopathy).

For therapeutic applications, the antibody, or antigen-binding fragment thereof, of the invention can be administered to a mammal, especially a human by conventional techniques, such as intravenously (as a bolus or by continuous infusion over a period of time), intramuscularly, intraperitoneally, intra-cerebrospinally, subcutaneously, intra-articularly, intrasynovially, intrathecally, orally, topically, or by inhalation. The antibody, or antigen-binding fragment thereof, of the invention also is suitably administered by intra-tumoral, peri-tumoral, intra-lesional, or peri-lesional routes.

Accordingly, in one aspect, the invention provides a method of reducing the activity of IFNβ, comprising administering to a subject (e.g., a human) in need thereof a therapeutically effective amount of the antibody, or antigen-binding fragment thereof, of the invention.

In certain embodiments, the subject suffers from or is susceptible to a rheumatic disease. In certain embodiments, the rheumatic disease is SLE. In certain embodiments, the rheumatic disease is DM.

In certain embodiments, the subject suffers from or is susceptible to an interferonopathy.

In certain embodiments, the antibody, or antigen-binding fragment thereof, of the invention is administered subcutaneously. In certain embodiments, the antibody, or antigen-binding fragment thereof, of the invention is administered intravenously.

The pharmaceutical compositions may be administered to a subject in need thereof at a frequency that may vary with the severity of the rheumatic disease or interferonopathy. In the case of prophylactic therapy, the frequency may vary depending on the subject's susceptibility or predisposition to a rheumatic disease or an interferonopathy.

The compositions may be administered to patients in need as a bolus or by continuous infusion. For example, a bolus administration of an antibody present as a Fab fragment may be in an amount of from 0.0025 to 100 mg/kg body weight, 0.025 to 0.25 mg/kg, 0.010 to 0.10 mg/kg or 0.10-0.50 mg/kg. For continuous infusion, an antibody present as an Fab fragment may be administered at 0.001 to 100 mg/kg body weight/minute, 0.0125 to 1.25 mg/kg/min, 0.010 to 0.75 mg/kg/min, 0.010 to 1.0 mg/kg/min. or 0.10-0.50 mg/kg/min fora period of 1-24 hours, 1-12 hours, 2-12 hours, 6-12 hours, 2-8 hours, or 1-2 hours.

For administration of an antibody present as a full-length antibody (with full constant regions), dosage amounts may be from about 1 mg/kg to about 10 mg/kg, from about 2 mg/kg to about 10 mg/kg, from about 3 mg/kg to about 10 mg/kg, from about 4 mg/kg to about 10 mg/kg, from about 5 mg/kg to about 10 mg/kg, from about 1 mg/kg to about 20 mg/kg, from about 2 mg/kg to about 20 mg/kg, from about 3 mg/kg to about 20 mg/kg, from about 4 mg/kg to about 20 mg/kg, from about 5 mg/kg to about 20 mg/kg, about 1 mg/kg or more, about 2 mg/kg or more, about 3 mg/kg or more, about 4 mg/kg or more, about 5 mg/kg or more, about 6 mg/kg or more, about 7 mg/kg or more, about 8 mg/kg or more, about 9 mg/kg or more, about 10 mg/kg or more, about 11 mg/kg or more, about 12 mg/kg or more, about 13 mg/kg or more, about 14 mg/kg or more, about 15 mg/kg or more, about 16 mg/kg or more, about 17 mg/kg or more, about 19 mg/kg or more, or about 20 mg/kg or more. The frequency of the administration would depend upon the severity of the condition. Frequency could range from three times per week to once every two or three weeks.

Additionally, the compositions may be administered to patients via subcutaneous injection. For example, a dose of 1 to 100 mg anti-IFNβ antibody can be administered to patients via subcutaneous or intravenous injection administered twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, or once every three months. For example, antibody CTI-AF1 has an estimated half-life of about 19 days. This half-life supports subcutaneous or intravenous injection at every 2-6 weeks, such as once every 2 weeks or once every 4 weeks.

In certain embodiments, the half-life of the anti-IFNβ antibody in human is about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, from about 5 days to about 40 days, from about 5 days to about 35 days, from about 5 days to about 30 days, from about 5 days to about 25 days, from about 10 days to about 40 days, from about 10 days to about 35 days, from about 10 days to about 30 days, from about 10 days to about 25 days, from about 15 days to about 40 days, from about 15 days to about 35 days, from about 15 days to about 30 days, or from about 15 days to about 25 days, In certain embodiments, the pharmaceutical composition is administered subcutaneously or intravenously at every 2-6 weeks, with a dose from about 0.1 mg/kg to about 10 mg/kg, from about 0.5 mg/kg to about 10 mg/kg, from about 1 mg/kg to about 10 mg/kg, from about 1.5 mg/kg to about 10 mg/kg, from about 2 mg/kg to about 10 mg/kg, from about 0.1 mg/kg to about 8 mg/kg, from about 0.5 mg/kg to about 8 mg/kg, from about 1 mg/kg to about 8 mg/kg, from about 1.5 mg/kg to about 8 mg/kg, from about 2 mg/kg to about 8 mg/kg, from about 0.1 mg/kg to about 5 mg/kg, from about 0.5 mg/kg to about 5 mg/kg, from about 1 mg/kg to about 5 mg/kg, from about 1.5 mg/kg to about 5 mg/kg, from about 2 mg/kg to about 5 mg/kg, about 0.5 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 5.5 mg/kg, about 6.0 mg/kg, about 6.5 mg/kg, about 7.0 mg/kg, about 7.5 mg/kg, about 8.0 mg/kg, about 8.5 mg/kg, about 9.0 mg/kg, about 9.5 mg/kg, or about 10.0 mg/kg.

In certain embodiments, the pharmaceutical composition is administered subcutaneously or intravenously at every 2-6 weeks, with a dose of about 2.0 mg/kg. In certain embodiments, the pharmaceutical composition is administered subcutaneous or intravenously every 2-6 weeks, with a dose of from about 2.0 mg/kg to about 10.0 mg/kg.

In one exemplary embodiment, pharmaceutical composition is administered subcutaneously every 2 weeks.

The antibody, or antigen-binding fragment thereof, of the invention can be used as monotherapy or in combination with other therapies to treat a rheumatic disease.

3. Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

An "antigen-binding fragment" of an antibody refers to a fragment of a full-length antibody that retains the ability to specifically bind to an antigen (preferably with substantially the same binding affinity). Examples of an antigen-binding fragment includes (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR), disulfide-linked Fvs (dsFv), and anti-idiotypic (anti-Id) antibody and intrabody. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et al. Science 242:423-426 (1988) and Huston et al., Proc. Natl. Acad. Sci. USA 85:5879-5883 (1988)). Other forms of single chain antibodies, such as diabodies, are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see e.g., Holliger et al. Proc. Natl. Acad. Sci. USA 90:6444-6448 (1993); Poljak et al., 1994, Structure 2:1121-1123).

An antibody "variable domain" refers to the variable region of the antibody light chain (VL) or the variable region of the antibody heavy chain (VH), either alone or in combination. As known in the art, the variable regions of the heavy and light chains each consist of three complementarity determining regions (CDRs), and connected by four framework regions (FR),and contribute to the formation of the antigen-binding site of antibodies.

Residues in a variable domain are numbered according Kabat, which is a numbering system used for heavy chain variable domains or light chain variable domains of the compilation of antibodies. See, Kabat et al., Sequences of Proteins of Immunological Interest, 5th Ed. Public Health Service, National Institutes of Health, Bethesda, MD (1991)). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR-H2 and inserted residues (e.g. residues 82a, 82b, and 82c, according to Kabat) after heavy chain FR residue 82. The Kabat numbering of residues may be determined for a given antibody by alignment at regions of homology of the sequence of the antibody with a "standard" Kabat numbered sequence. Various algorithms for assigning Kabat numbering are available. The algorithm implemented in the 2012 release of Abysis (www.abysis.org) is used herein to assign Kabat numbering to variable regions unless otherwise noted.

Specific amino acid residue positions in an antibody (such as paratope residues) are also numbered according to Kabat.

"Complementarity Determining Regions" (CDRs) can be identified according to the definitions of the Kabat, Chothia, the accumulation of both Kabat and Chothia, AbM, contact, and/or conformational definitions or any method of CDR determination well known in the art. See, e.g., Kabat et al., 1991, Sequences of Proteins of Immunological Interest, 5th ed. (hypervariable regions); Chothia et al., 1989, Nature 342:877-883 (structural loop structures). AbM definition of CDRs is a compromise between Kabat and Chothia and uses Oxford Molecular's AbM antibody modeling software (ACCELRYS®).The "contact" definition of CDRs is based on observed antigen contacts, set forth in MacCallum et al., 1996, J. Mol. Biol., 262:732-745. The "conformational" definition of CDRs is based on residues that make enthalpic contributions to antigen binding (see, e.g., Makabe et al., 2008, Journal of Biological Chemistry, 283:1156-1166). Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches.

In the Examples (see Table 11), the CDRs are defined as follows (numbering according to Kabat; H: heavy chain; L: light chain):

CDR-H1: H26-H35B; CDR-H2: H50-H65; CDR-H3: H95-H102

CDR-L1: L24-L34; CDR-L2: L50-L56; CDR-L3: L89-L97

"Framework" (FR) residues are antibody variable domain residues other than the CDR residues. A VH or VL domain framework comprises four framework sub-regions, FR1, FR2, FR3 and FR4, interspersed with CDRs in the following structure: FR1-CDR1-FR2-CDR2-FR3-CDR3-FR4. In the Examples (see Table 11), FR residues include the following (numbering according to Kabat; H: heavy chain; L: light chain):

TABLE 5

|  | FR1 | FR2 | FR3 | FR4 |
|---|---|---|---|---|
| Heavy Chain | H1-H25 | H36-H49 | H66-H94 | H103-H113 |
| Light Chain | L1-L23 | L35-L49 | L57-L88 | L98-L107 |

An "epitope" refers to the area or region of an antigen (Ag) to which an antibody specifically binds, e.g., an area or region comprising amino acid residues that interact with the antibody (Ab). Epitopes can be linear or non-linear (e.g., conformational).

An antibody, or antigen-binding fragment thereof, binds substantially the same epitope as another antibody, or antigen-binding fragment thereof, when binding of the corresponding antibodies, or antigen-binding fragments thereof, are mutually exclusive. That is, binding of one antibody, or antigen-binding fragment thereof, excludes simultaneous or consecutive binding of the other antibody, or antigen-binding fragment thereof. Epitopes are said to be unique, or not substantially the same, if the antigen is able to accommodate binding of both corresponding antibodies, or antigen-binding fragments thereof, simultaneously.

The term "paratope" is derived from the above definition of "epitope" by reversing the perspective, and refers to the area or region of an antibody molecule which is involved in binding of an antigen, e.g., an area or region comprising residues that interacts with the antigen. A paratope may be linear or conformational (such as discontinuous residues in CDRs).

The epitope/paratope for a given antibody/antigen binding pair can be defined and characterized at different levels of detail using a variety of experimental and computational epitope mapping methods. The experimental methods include mutagenesis, X-ray crystallography, Nuclear Magnetic Resonance (NMR) spectroscopy, Hydrogen/deuterium exchange Mass Spectrometry (HX-MS) and various competition binding methods. As each method relies on a unique principle, the description of an epitope is intimately linked to the method by which it has been determined. Thus, the epitope/paratope for a given antibody/antigen pair will be defined differently depending on the mapping method employed.

At its most detailed level, the epitope/paratope for the interaction between an antibody (Ab) and antigen (Ag) can be defined by the spatial coordinates defining the atomic contacts present in the Ag-Ab interaction, as well as information about their relative contributions to the binding thermodynamics. At one level, an epitope/paratope residue can be characterized by the spatial coordinates defining the atomic contacts between the Ag and Ab. In one aspect, the epitope/paratope residue can be defined by a specific criterion, e.g., distance between atoms in the Ab and the Ag (e.g., a distance of equal to or less than about 4 Å (such as 3.8 Å used in the Examples here) from a heavy atom of the cognate antibody and a heavy atom of the antigen. In another aspect, an epitope/paratope residue can be characterized as participating in a hydrogen bond interaction with the cognate antibody/antigen, or with a water molecule that is also hydrogen bonded to the cognate antibody/antigen (water-mediated hydrogen bonding). In another aspect, an epitope/paratope residue can be characterized as forming a salt bridge with a residue of the cognate antibody/antigen. In yet another aspect, an epitope/paratope residue can be characterized as a residue having a non-zero change in buried surface area (BSA) due to interaction with the cognate antibody/antigen. At a less detailed level, epitope/paratope can be characterized through function, e.g., by competition binding with other Abs. The epitope/paratope can also be defined more generically as comprising amino acid residues for which substitution by another amino acid will alter the characteristics of the interaction between the Ab and Ag (e.g. alanine scanning).

In the context of an X-ray derived crystal structure defined by spatial coordinates of a complex between an antibody, e.g., a Fab fragment or two Fab fragments, and its antigen, unless otherwise specified, an epitope residue refers to an IFNβ residue (i) having a heavy atom (i.e., a non-hydrogen atom) that is within a distance of about 4 Å (e.g., 3.8 Å) from a heavy atom of the cognate antibody; (ii) participating in a hydrogen bond with a residue of the cognate antibody, or with a water molecule that is also hydrogen bonded to the cognate antibody (water-mediated hydrogen bonding), (iii) participating in a salt bridge to a residue of the cognate antibody, and/or (iv) having a non-zero change in buried surface area (BSA) due to interaction with the cognate antibody. In general, a cutoff is imposed for BSA to avoid inclusion of residues that have minimal interactions. Therefore, unless otherwise specified, epitope residues under category (iv) are selected if it has a BSA of 20 Å$^2$ or greater, or is involved in electrostatic interactions when the antibody binds to IFNβ. Similarly, in the context of an X-ray derived crystal structure, unless otherwise specified or contradicted by context, a paratope residue, refers to an antibody residue (i) having a heavy atom (i.e., a non-hydrogen atom) that is within a distance of about 4 Å from a heavy atom of IFNβ, (ii) participating in a hydrogen bond with an IFNβ residue, or with a water molecule that is also hydrogen bonded to IFNβ (water-mediated hydrogen bonding), (iii) participating in a salt bridge to a residue of IFNβ, and/or (iv) having a non-zero change in buried surface area due to interaction with IFNβ. Again, unless otherwise specified, paratope residues under category (iv) are selected if it has a BSA of 20 Å$^2$ or greater, or is involved in electrostatic interactions when antibody binds to IFNβ. Residues identified by (i) distance or (iv) BSA are often referred to as "contact" residues.

From the fact that descriptions and definitions of epitopes, dependent on the epitope mapping method used, and obtained at different levels of detail, it follows that comparison of epitopes for different Abs on the same Ag can similarly be conducted at different levels of detail. For example, epitopes described on the amino acid level, e.g., determined from an X-ray structure, are said to be identical if they contain the same set of amino acid residues. Epitopes characterized by competition binding are said to be overlapping if the binding of the corresponding antibodies are mutually exclusive, i.e., binding of one antibody excludes simultaneous or consecutive binding of the other antibody; and epitopes are said to be separate (unique) if the antigen is able to accommodate binding of both corresponding antibodies simultaneously.

The epitope and paratope for a given antibody/antigen pair may be identified by routine methods. For example, the general location of an epitope may be determined by assessing the ability of an antibody to bind to different fragments or variant IFNβ polypeptides as more fully described previously elsewhere herein. Specific residues within IFNβ that make contact with specific residues within an antibody may also be determined using routine methods, such as those described in the examples. For example, antibody/antigen complex may be crystallized. The crystal structure may be determined and used to identify specific sites of interaction between the antibody and antigen.

The terms "specifically binds" and "specific binding" are terms well-understood in the art, and methods to determine such specific binding are also well known in the art. A molecule is said to exhibit "specific binding" if it reacts or associates more frequently, more rapidly, with greater duration and/or with greater affinity with a particular cell or substance, than it does with alternative cells or substances. An antibody, or antigen-binding fragment thereof, "specifically binds" to a target (e.g., IFNβ) if it binds with greater affinity, avidity, more readily, and/or with greater duration than it binds other substances.

For example, an antibody, or antigen-binding fragment thereof, that specifically binds IFNβ is an antibody that binds its cognate antigen (IFNβ) with greater affinity, avidity, more readily, and/or with greater duration than it binds other antigens, such as other members of the IFN superfamily (e.g., INFα, IFNγ, IFNω), or other unrelated molecules. For example, an anti-IFNβ antibody can specifically binds human IFNβ in a sample, but does not substantially recognize or bind other molecules in the sample under a standard binding assay condition. It is also understood that an antibody, or antigen-binding fragment thereof, which specifically binds a first target may or may not specifically bind to a second target. As such, "specific binding" does not necessarily require (although it can include) exclusive binding. Generally, but not necessarily, reference to "binding" means specific binding.

A variety of assay formats may be used to select an antibody, or antigen-binding fragment thereof, that specifically binds a molecule of interest. For example, solid-phase ELISA immunoassay, immunoprecipitation, BIACORE™ (GE Healthcare), KinExA, fluorescence-activated cell sorting (FACS), OCTET™ (FortéBio, Inc.) and Western blot analysis are among many assays that may be used to identify an antibody, or antigen-binding fragment thereof, that specifically binds an antigen. Typically, a specific binding will be at least twice of the background signal or noise, more typically at least 10 times of background, at least 50 times of background, at least 100 times of background, at least 500 times of background, at least 1000 of times background, or at least 10,000 times of background.

The specificity of an antibody binding may be assessed by determining and comparing the $K_D$ values of a specific binding between an antibody and IFNβ, with the $K_D$ value of a control antibody that is known not to bind to IFNβ. In general, an antibody is said to "specifically bind" an antigen when the $K_D$ is about $\times 10^{-5}$ M or less.

An antibody, or antigen-binding fragment thereof, "does not substantially bind" to an antigen when it does not bind to said antigen with greater affinity, avidity, more readily, and/or with greater duration than it binds other antigens. Typically, the binding will be no greater than twice of the background signal or noise. In general, it binds the antigen with a $K_D$ of $1\times 10^{-4}$ M or more, $1\times 10^{-3}$ M or more, $1\times 10^{-2}$ M or more, or $1\times 10^{-1}$ M or more.

The term "compete", as used herein with regard to an antibody, means that binding of a first antibody, or an antigen-binding portion thereof, to an antigen reduces the subsequent binding of the same antigen by a second antibody or an antigen-binding portion thereof. In general, binding of a first antibody creates steric hindrance, conformational change, or binding to a common epitope (or portion thereof), such that the binding of the second antibody to the same antigen is reduced. Standard competitive binding assays may be used to determine whether two antibodies compete with each other.

One suitable assay for antibody competition involves the use of the Biacore technology, which can measure the extent of interactions using surface plasmon resonance (SPR) technology, typically using a biosensor system (such as a BIACORE® system). For example, SPR can be used in an in vitro competitive binding inhibition assay to determine the ability of one antibody to inhibit the binding of a second antibody. Another assay for measuring antibody competition uses an ELISA-based approach. Furthermore, a high throughput process for "binning" antibodies based upon their competition is described in WO2003/48731. Competition is present if one antibody, or antigen-binding fragment thereof, reduces the binding of another antibody, or antigen-binding fragment thereof, to IFNβ. For example, a sequential binding competition assay may be used, with different antibodies being added sequentially. The first antibody may be added to reach binding that is close to saturation. Then, the second antibody is added. If the binding of second antibody to IFNβ is not detected, or is significantly reduced (e.g., at least about 10%, at least about 20%, at least about 30%, at least about 40%, at least about 50%, at least about 60%, at least about 70%, at least about 80%, or at least about 90% reduction) as compared to a parallel assay in the absence of the first antibody (which value can be set as 100%), the two antibodies are considered as competing with each other. An exemplary antibody competition assay (and overlapping epitope analysis) by SPR is provided in Example 1.

A competitive binding assay can also be conducted in which the binding of the antibody to the antigen is compared to the binding of the target by another binding partner of that target, such as another antibody or a soluble receptor that otherwise binds the target. The concentration at which 50% inhibition occurs is known as the $K_i$. Under ideal conditions, the $K_i$ is equivalent to $K_D$. Thus, in general, measurement of $K_i$ can conveniently be substituted to provide an upper limit for $K_D$. Binding affinities associated with different molecular interactions, e.g., comparison of the binding affinity of different antibodies for a given antigen, may be compared by comparison of the $K_D$ values for the individual antibody/antigen complexes. $K_D$ values for antibodies or other binding partners can be determined using methods well established in the art.

An "Fc fusion" protein is a protein wherein one or more polypeptides are operably linked to an Fc polypeptide. An Fc fusion combines the Fc region of an immunoglobulin with a fusion partner. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as described in Kabat et al., Sequences of Proteins of Immunological Interest, 5th Ed. Public Health Service, National Institutes of Health, Bethesda, MD, 1991. The Fc region of an immunoglobulin generally comprises two constant domains, $CH_2$ and $CH_3$. As is known in the art, an Fc region can be present in dimer or monomeric form.

The term "therapeutically effective amount" means an amount of an anti-IFNβ antibody, or an antigen-binding fragment thereof, or a combination comprising such antibody, or antigen-binding fragment thereof, that is of sufficient quantity to achieve the intended purpose, such as decreased binding of IFNβ to IFNAR, the decreased phosphorylation of STAT1 and/or STAT2, the decreased expression of IFNβ-dependent gene, or otherwise causing a measurable benefit in vivo to a subject in need. The precise amount will depend upon numerous factors, including, but not limited to the components and physical characteristics of the therapeutic composition, intended patient population, individual patient considerations, and the like, and can be determined by one skilled in the art.

The term "treatment" includes prophylactic and/or therapeutic treatments. If it is administered prior to clinical manifestation of a disease, disorder, or condition, the treatment is considered prophylactic. Therapeutic treatment includes, e.g., ameliorating or reducing the severity of a disease, disorder, or condition, or shortening the length of the disease, disorder, or condition. Preferably, the disease, disorder, or condition is mediated by or related to IFNβ binding to IFNAR.

The term "about", as used herein, refers to +/−10% of a value.

Biological Deposit

Representative materials of the present invention were deposited in the American Type Culture Collection, 10801 University Boulevard, Manassas, VA 20110-2209, USA, on Dec. 18, 2015. Vector CTI-AF1-VH, having ATCC Accession No. PTA-122727, comprises a DNA insert encoding the heavy chain variable region of antibody CTI-AF1, and vector CTI-AF1-VL, having ATCC Accession No. PTA-122726, comprises a DNA insert encoding the light chain variable region of antibody CTI-AF1. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc. and ATCC, which assures permanent and unrestricted availability of the progeny of the culture of the deposit to the public upon issuance of the pertinent U.S. patent or upon laying open to the public of any U. S. or foreign patent application, whichever comes first, and assures availability of the progeny to one determined by the U. S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The owner of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1. Generation Of Anti-IFNβ Antibodies

Antibody CTI-AF1 is a humanized IgG1 antibody against the soluble cytokine interferon beta (IFNβ). A mouse monoclonal antibody (mouse mAb) against human IFNβ was generated by standard immunizations of female BALB/c mice with human IFNβ, and subsequent hybridoma screening.

Two hybridoma clones were selected for humanization based on kinetic binding profile. The clones showed a $K_D$ value of about 20 nM and an $IC_{50}$ of about 20 nM. Hybridoma clones were humanized by using human germline frameworks sequences from IGKV1-39 (DPK9 light chain variable domain; Gene Bank Accession No. X59315) and IGHV1-69 (DP10 heavy chain variable domain; Gene Bank Accession No. L22582).

Multiple rounds of affinity maturation were used to increase the affinity of the antibody. The sequences of VL region of these antibodies are shown in Table 11. All antibodies in Table 11 have the same VH sequence. In particular, CTI-AF1 showed a decrease in $K_D$ value from 25 nM to 29 μM by introducing the following mutations in the light chain variable domain: S to G mutation in position 30, H to I and T to I mutations at position 92 and 93 respectively, and L to I mutation in position 96. No mutations were introduced in the heavy chain variable domain.

The affinities of CTI-AF antibodies to human interferon beta (IFNβ) were determined by SPR as follows, using a Biacore T200 instrument. Antibodies were directly immobilized on the surface of a CM5 sensor chip at room temperature, using standard amine-coupling technique. Immobilization levels covered a range from 49 to 375 resonance units (RU). The analyte, recombinant human IFNβ, was then injected in a series of dilutions ranging from 10 nM down to 0.078 nM (2-fold dilution), at a flow rate of 30 to 50 μL per minute for an association time ranging from 65 to 300 seconds, followed by a dissociation phase of 10 minutes. Each concentration was evaluated in duplicate. The analyte was removed by regeneration of the CM5 sensor chip surface between each cycle using 3 M $MgCl_2$ at pH 3.0 or 10 mM glycine-HCl at pH 1.5, followed by a buffer rinse. This regeneration step removed the bound analyte and returned the response signal to baseline. Data from the reference flow cell (without analyte) were subtracted from the antigen binding responses to remove systematic artifacts. The apparent binding affinity was determined with a 1:1 interaction model using Biacore T200 evaluation software version 2.0. The equilibrium constant $K_D$ was determined as the ratio of the kinetic rate constants, $k_d/k_a$. Binding was validated by repeating the binding experiments over multiple days, using two separate instruments and different flow cells on the CM5 sensor chip. The results are shown in Table 6.

TABLE 6 summaries of biological activities of the antibodies in Table 11

| Ab Name | $K_D$ (M)—biacore | Response rank (Octet) | IC50 (pM) ISRE Neutralization | IC50 (pM) pSTAT1 Inhibition |
|---|---|---|---|---|
| CTI-AF1 | 3.6E−11 | 1 | 2 | 4 |
| CTI-AF2 | — | — | — | — |
| CTI-AF3 | — | — | — | — |
| CTI-AF4 | — | 4 | — | — |
| CTI-AF5 | — | — | — | 10 |
| CTI-AF6 | — | — | — | — |
| CTI-AF7 | — | — | — | — |
| CTI-AF8 | — | 6 | 460 | — |
| CTI-AF9 | — | 12 | 75 | — |
| CTI-AF10 | — | 5 | — | — |
| CTI-AF11 | — | — | — | — |
| CTI-AF12 | — | — | — | — |
| CTI-AF13 | — | — | — | — |
| CTI-AF14 | — | 7 | — | 30 |
| CTI-AF15 | — | 3 | — | 80 |
| CTI-AF16 | — | 2 | 14 | — |
| CTI-AF17 | — | — | — | — |
| CTI-AF18 | — | — | — | — |
| CTI-AF19 | — | — | — | — |
| CTI-AF20 | 3.35E−10 | 8 | — | 20 |
| CTI-AF21 | — | 11 | — | — |
| CTI-AF22 | — | — | — | — |
| CTI-AF23 | — | 9 | — | — |
| CTI-AF24 | — | — | — | — |
| CTI-AF25 | — | — | — | — |
| CTI-AF26 | — | — | — | — |
| CTI-AF27 | — | 10 | — | 70 |

Example 2. Biophysical Properties of Anti-IFNβ Antibodies

CTI-AF1 was dialyzed and concentrated to 150 mg/mL in MOD1 buffer with 10K MWCO regenerated cellulose membrane. The cynomolgus monkey ETS material was ultrafiltrated/diafiltrated into the same buffer to a final concentration of 72 mg/mL with minimal losses of product. When formulated in PBS, pH 7.2 at ~50 mg/mL, CTI-AF1 phase-separated at 2-8° C. and formed a stable milky emulsion. Upon warming up to room temperature, the solution becomes clear again. In MOD1 buffer, no phase-separation occurred.

Viscosity was measured at 22° C. using the mVROC viscometer. Injections were performed at 100 μL/min using a 100 μL Hamilton syringe. The dependence of viscosity on concentration is shown in FIG. 1. Even at the maximum concentration the viscosity is still below 10 cP.

Figure 2:
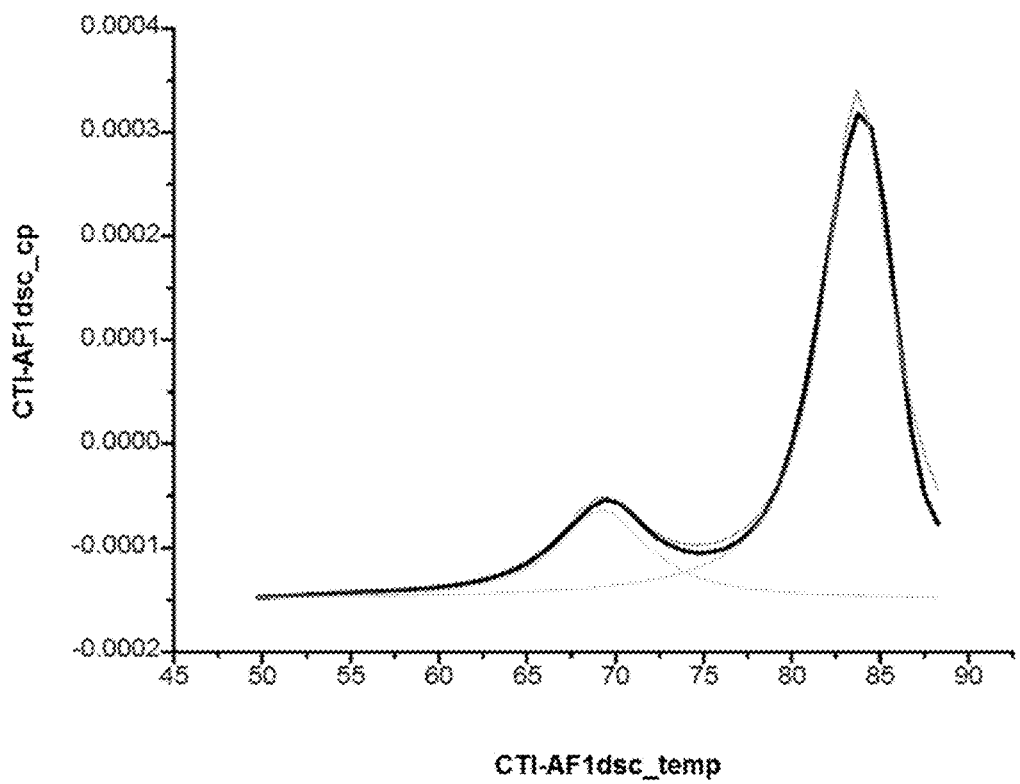
FIG. 2 is a differential scanning calorimetry (DSC) graph of antibody CTI-AF1.

Thermal stability was evaluated using MicroCal VP-DSC (Malvern). CTI-AF1 was scanned at 1 mg/mL protein in MOD1 buffer at 1 deg/min. As shown in FIG. 2, the first melting transition of this molecule occurs at 69.4° C., which is well above the known required stability threshold for commercial scale manufacturability.

Figure 3:
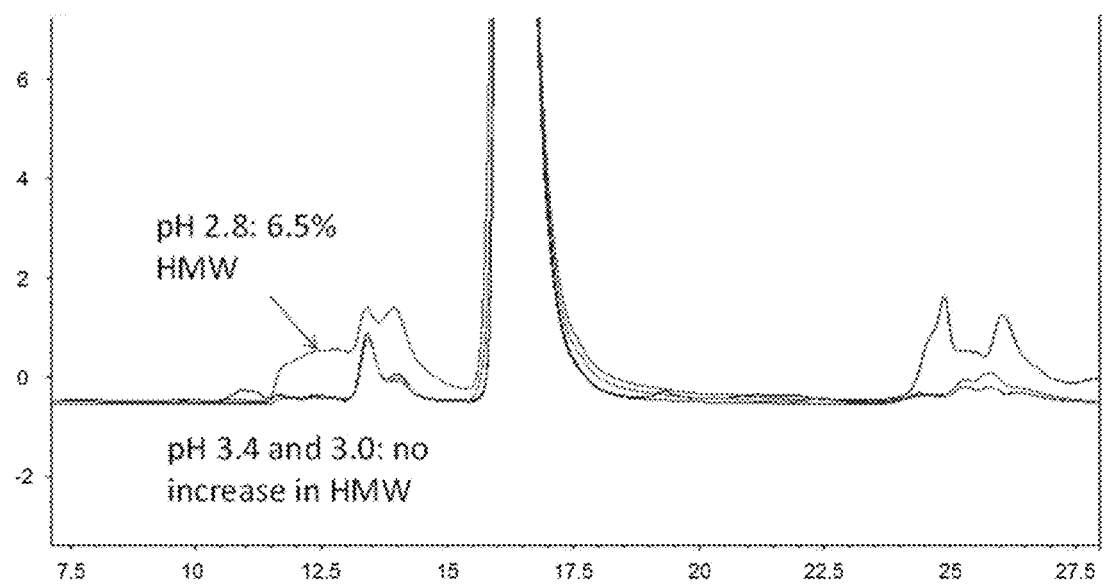
FIG. 3 is the Size-Exclusion HPLC (SE-HPLC) analysis of CTI-AF1 aggregation, as a result of low-pH hold.

Low-pH stability was evaluated by titrating protein A pool with citric acid down to pH 2.8, 3.0 and 3.4 and incubating for 5 hours at room temperature before neutralizing to pH 7.0. As shown in FIG. 3, the formation of HMMS occurs only at pH 2.8, while at higher pH levels the product is stable. This stability will enable inactivation of enveloped viruses at low pH, as required for commercial manufacture.

Freeze/thaw stability was performed at 72 mg/mL in MOD1 buffer by placing an Eppendorf tube containing 1 mL of product at −80° C. for 10 min, followed by thawing at room temperature. No significant aggregation was observed after 3 cycles of freeze-thaw.

Figure 4A:
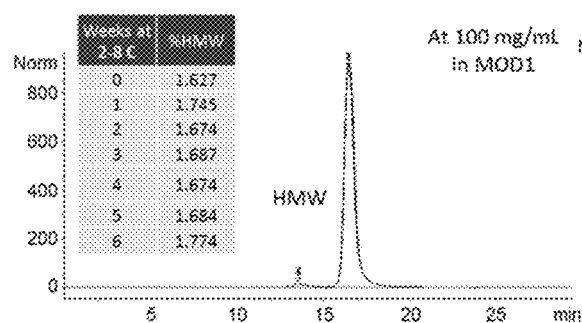
FIGS. 4A-4D show the SE-HPLC analysis of time points from stability studies.
Figure 4B:
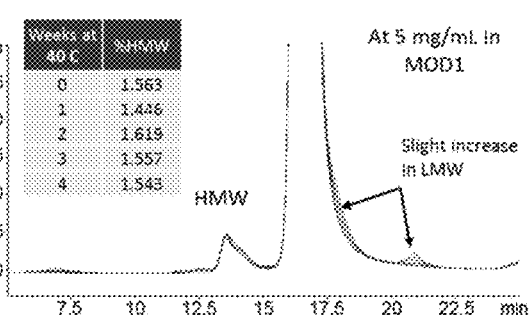
Figure 4C:
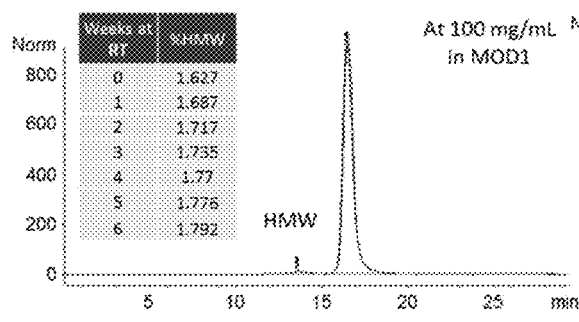
Figure 4D:
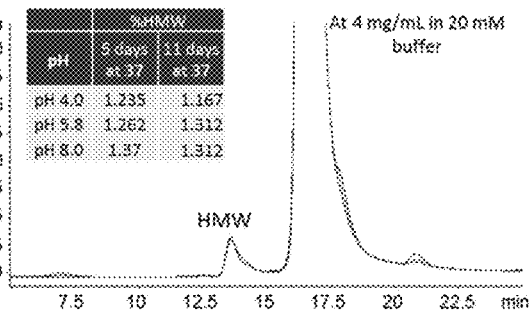
Figure 5A:
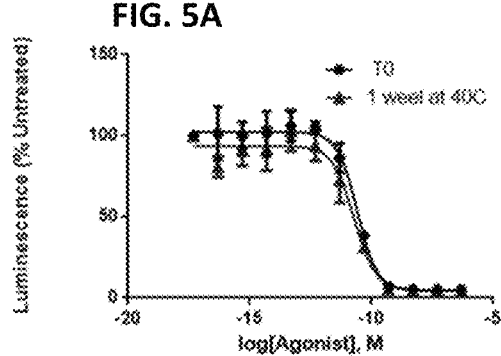
FIGS. 5A-5D show graphs demonstrating that CTI-AF1 is stable over time when stored at 40° C. and does not lose the ability to neutralize IFNβ. CTI-AF1 was stored at various temperatures and time periods then the ability of the antibody to neutralize IFNβ in an IFN dependent luciferase reporter assay was evaluated. Material stored for 1 week at 40° C.
Figure 5B:
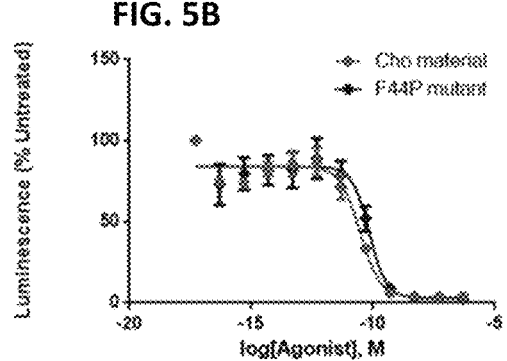
Figure 5C:
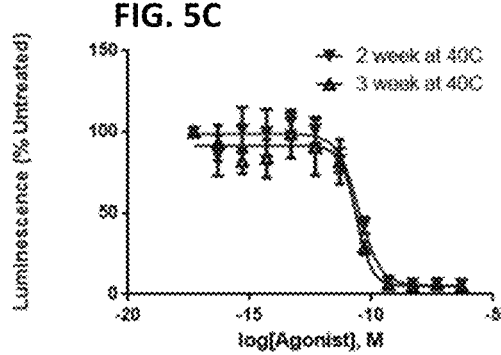
Figure 5D:
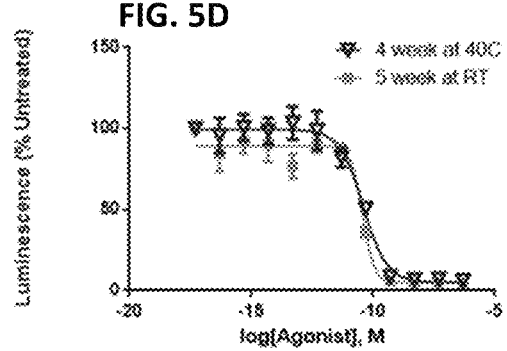

Stability studies were performed at 100 mg/mL in MOD1 buffer for 6 weeks at 2-8° C. (FIG. 4A) and ambient temperature (22° C., FIG. 4C); in MOD1 buffer at 5 mg/mL for 4 weeks at 40° C. (FIG. 4B); in 20 mM buffer (glutamic acid pH 4.0, histidine pH 5.8, tris pH 8.0) at 4 mg/mL for 5 or 11 days at 37° C. (FIG. 4D). Testing of the time points was performed by SE-HPLC. No significant increase in HMW was detected in any of the studies. Similarly analysis by CGE did not show any significant differences between the time points. Charge heterogeneity was assayed by iCE (Table 7), which showed an increase in acidic species at 37° C. (particularly at pH 8.0) and 40° C., indicating some degree of deamidation and/or oxidation. However, no major changes were detected to trigger a liquid chromatography (LS)/mass spectrometry (MS) investigation. Other stability series (2-8° C. and ambient temperature) did not show significant changes in % acidic and % basic species by iCE.

The stability time points from the 40° C. series were tested in the cell-based assay measuring the neutralization of IFNβ activity (FIGS. 5 A-D). On day 1, 20,000 HEK293 ISRE-Luc (IFNβ responsive luciferase reporter) cells were plated in 100 μL of DMEM containing 10% fetal bovine serum (FBS) per well in tissue culture treated 96 well plates. Antibody solutions were prepared as 2× stocks starting at a top concentration of 1 μM in DMEM/10% FBS, and then an 11 point, 10-fold dilution series was made with media. A 20× stock of IFNβ (0.625 ng/mL) was prepared in media and added to the antibody titration stocks to a final 2× concentration. The antibody:IFNβ solutions were incubated for 2 hours at 37° C., then 100 μL of the solution was added per well and plates were cultured overnight at 37° C. On day 3, a 150 μg/mL solution of Beetle Luciferine, potassium salt was prepared and 20 μL/well was added and plates were incubated for 15 minutes at 37° C. Luminesence was read on an EnVision multilabel plate reader. No changes in neutralizing activity were detected.

CTI-AF1 is compatible with a formulation buffer (20 mM His, 8.5% Sucrose, 0.05 mg/mL EDTA, pH 5.8) and maintains solubility up to 150 mg/mL with acceptable viscosity.

TABLE 7

Charge heterogeneity in the stability samples

| Sample Name | pI | Acidic | Main | Basic |
|---|---|---|---|---|
| HC_T0 | 8.74 | 17.3 | 79.5 | 3.2 |
| HC_1wk4C | 8.74 | 17.4 | 79.7 | 3 |
| HC_2wk4C | 8.75 | 17.5 | 79.1 | 3.3 |
| HC_3wk4C | 8.74 | 17.7 | 78.9 | 3.4 |
| HC_4wk4C | 8.75 | 18.1 | 78.9 | 3 |
| HC_5wk4C | 8.74 | 19.1 | 77.1 | 3.8 |
| HC_6wk4C | 8.74 | 17.8 | 79.2 | 3 |
| HC_1wk25C | 8.74 | 17.4 | 79.3 | 3.4 |
| HC_2wk25C | 8.74 | 17.9 | 78.9 | 3.2 |
| HC_3wk_25C | 8.73 | 18.2 | 78.5 | 3.4 |
| HC_4wk25C | 8.73 | 19.2 | 76.9 | 3.9 |
| HC_5wk25C | 8.73 | 19.8 | 76.7 | 3.5 |
| HC_6wk25C | 8.72 | 20.3 | 76.4 | 3.4 |
| 40C_1wk | 8.71 | 23.9 | 70.8 | 5.2 |
| 40C_2wk | 8.7 | 32.8 | 60.8 | 6.4 |
| 40C_3wk | 8.7 | 37.4 | 56.7 | 5.9 |
| 40C_4wk | 8.7 | 42.1 | 52.1 | 5.7 |
| pH4_T0 | 8.7 | 18.7 | 78.5 | 2.8 |
| pH4_5d | 8.7 | 22 | 74.9 | 3.1 |
| pH4_11d | 8.69 | 25.9 | 67.4 | 6.7 |
| PH5_8_T0 | 8.74 | 19.3 | 77.7 | 3 |

TABLE 7-continued

Charge heterogeneity in the stability samples

| Sample Name | pI | Acidic | Main | Basic |
|---|---|---|---|---|
| pH5_8_5d | 8.73 | 21.3 | 75.6 | 3.2 |
| pH5_8_11d | 8.74 | 24.4 | 70.8 | 4.8 |
| pH8_T0 | 8.73 | 21 | 76.3 | 2.7 |
| pH8_5d | 8.74 | 27.5 | 70.1 | 2.4 |
| pH8_11d | 8.74 | 34.1 | 63.6 | 2.3 |

Example 3. Pharmacology

Brief Summary

CTI-AF1 is a potent and highly selective humanized IgG1 antibody against the soluble cytokine interferon beta (IFNβ). In vitro, CTI-AF1 showed high affinity for human IFNβ ($K_D$ of 36.7±12.4 µM). The antibody showed similar $EC_{50}$ binding for human and cynomolgus monkey IFNβ (15.28±2.11 µM and 25.04±5.11 µM, respectively). In human cell-based functional assays, CTI-AF1 showed potent neutralization of IFNβ induced STAT1 phosphorylation ($IC_{50}$ 7.7±5.0 to 29.8±6.9 µM) and expression of a type I interferon stimulated luciferase reporter in cultured human cells (ISRE assay; $IC_{50}$ 28.8±7.6 µM). CTI-AF1 also inhibited the IFNβ-driven expression of MxA (Mx1) in gene expression assays ($IC_{50}$ 29.4±23.5 µM) and was able to inhibit IFNβ endogenously expressed by human dermal fibroblasts, a disease relevant cell type, after polyinosinic:polycytidylic acid (poly I:C) stimulation.

Primary Pharmacology, In Vitro

Figure 6:
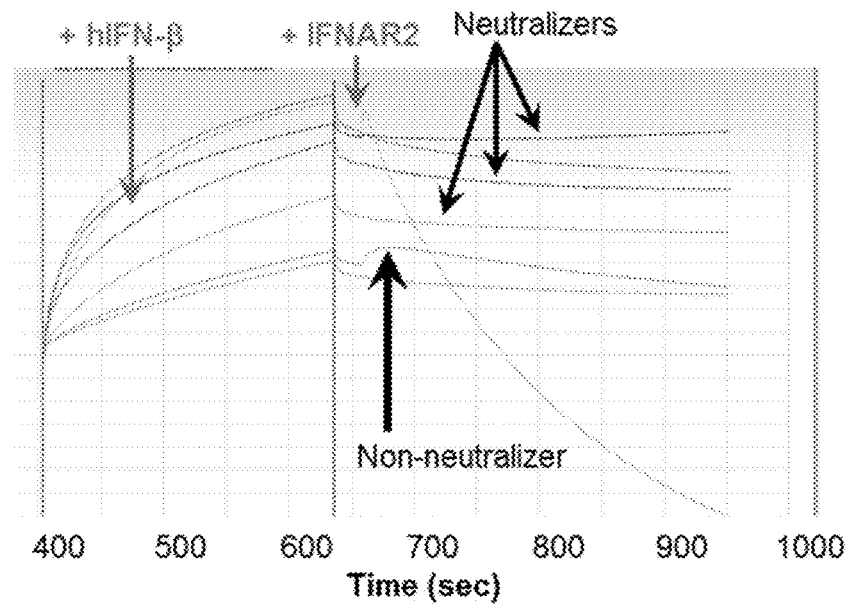
FIG. 6 depicts data showing identification of mouse anti-human IFNβ hybridomas that could block the binding of IFNβ to IFNAR2 by bio-layer interferometry (BLI) using the ForteBio Octet to measure molecular interaction. First, mouse anti-human IFNβ Abs were captured on a protein G sensor from conditioned culture media; next, human IFNβ was bound (indicated by the +hIFN-β arrow), then the Ab:IFNβ complexes were exposed to the high affinity chain of the human receptor, IFNAR2 (indicated by the+IFNAR2 arrow). Non-blocking antibodies show an upward bump in the curve indicative of additional binding (as indicated by the non-neutralizer arrow, bottom), whereas neutralizing antibodies demonstrated a relatively flat curve (as indicated by neutralizer arrows, top). Several mouse hybridomas demonstrated the ability to neutralize binding of IFNAR2 to IFNβ and were selected for further characterization and eventual humanization.

During the initial hybridoma screening, antibodies were selected based upon their ability to block the binding of IFNβ to IFNAR2, the high affinity component of the type I IFN receptor (FIG. 6). In subsequent screenings post humanization and affinity maturation, antibody selection was based upon functional neutralization of IFNβ in cell based assays.

Figure 7:
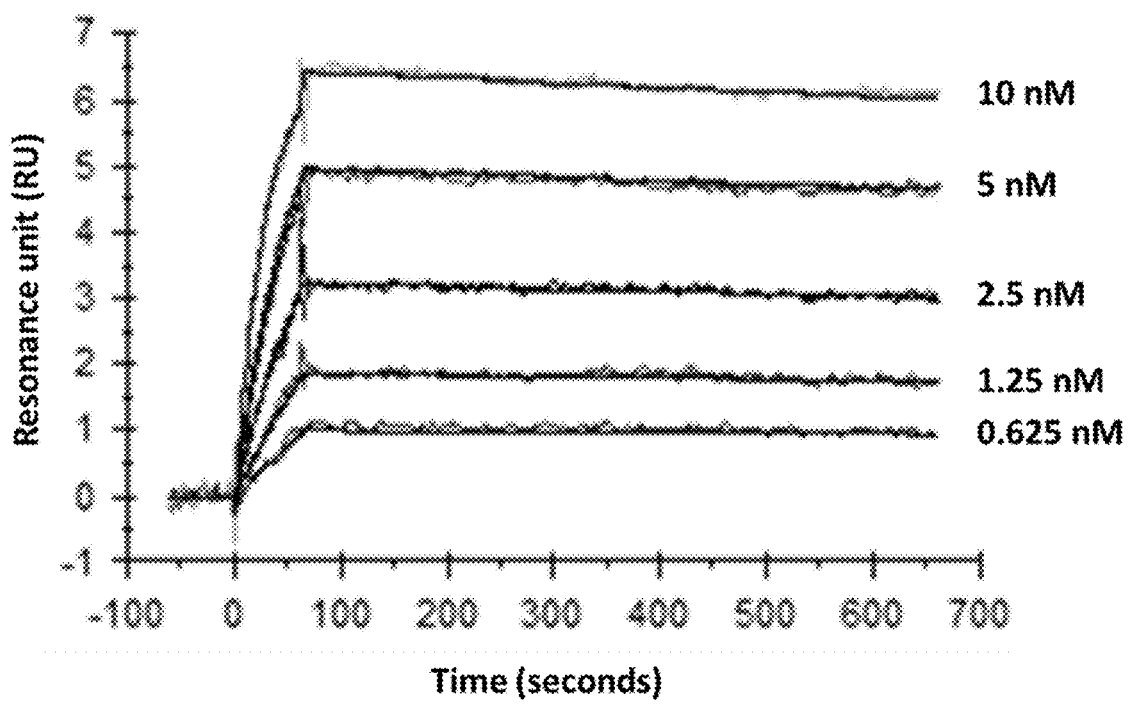
FIG. 7 depicts data showing determination of CTI-AF1's $K_D$ for human IFNβ by surface plasmon resonance (SPR). CTI-AF1 was captured on a CM5 sensor chip, then, starting at 2.5 nM IFNβ, a 6 point, 2-fold titration series of recombinant human IFNβ was flowed over CTI-AF1. The samples were run in duplicate and the concentration of IFNβ is indicated to the right of the graph. For each concentration of IFNβ, the thin grey lines depict the binding of IFNβ in each replicate sample; the heavier grey line represents the average fitted curve calculated by the analysis program. The $K_D$ of CTI-AF1 for human IFNβ was determined to be about 36 μM.

SPR was used to determine the $K_D$ of CTI-AF1 to human IFNβ; binding experiments were performed using a Biacore T200 optical biosensor equipped with research-grade CM5 sensor chip and human IFNβ (Peprotech). Regeneration of the chip was performed using stripping buffer (3 M $MgCl_2$ at pH 3.0 or 10 mM glycine at pH 1.5) followed by a buffer rinse. CTI-AF1 was immobilized on the surface of a CM5 sensor chip at room temperature. The capture level covered a range of 50 to 375 resonance units (RU). The analyte, human IFNβ, was then injected at a flow rate of 30-50 µL per minute for an association time ranging from 65-300 seconds, followed by a dissociation phase of 10 minutes. The kinetic characterization of the interactions was performed using the traditional multi-cycle method, using a series of human IFNβ concentrations from 10 nM down to 0.078125 nM in a series of 2-fold dilutions. Each concentration was evaluated in duplicate. The analyte was removed by regeneration of the array surface between each cycle using 3 M $MgCl_2$ at pH 3.0 or 10 mM glycine at pH 1.5, followed by a buffer rinse. This regeneration step removed the bound analyte and returned the response signal to baseline. Data from the reference flow cell (without analyte) were subtracted from the antigen binding responses to remove systematic artifacts. The apparent binding affinity was determined using a simple 1:1 interaction model and the equilibrium constant $K_D$ was determined as the ratio of the kinetic rate constants. The apparent binding affinity of CTI-AF1 for human IFNβ was determined to be 36.7±12.4 µM (FIG. 7).

Binding of CTI-AF1 to human IFNβ along with cynomolgus monkey, rabbit, rat and mouse orthologs and three of the nearest type I human homologs and IFNγ (type II) were evaluated in plate-based ELISAs. ELISA plates were coated overnight at 4° C. with 5 µg/mL of one of the following cytokines: human IFNβ, cynomolgus monkey IFNβ, rat IFNβ, human IFNα2, IFNγ, human IFNω; mouse IFNβ or human IFNα14(H2) were coated at 1 µg/mL, and rabbit IFNβ was coated at 10 ng/mL. All proteins were diluted in calcium and magnesium-free phosphate buffered saline. Coated plates were washed with phosphate buffered saline containing 0.05% Tween-20 (PBST) and blocked for 1 hour at room temperature with blocking buffer (PBST+0.5% BSA). Plates were washed again with PBST and primary antibodies were added to the plate at 30 nM starting concentration, followed by 1:3 dilutions in blocking buffer. For the anti-rabbit IFNβ, 1:10 dilutions were performed. Plates were incubated for 1 hour at room temperature and then washed with PBST. Binding was detected with species-specific peroxidase-linked secondary antibodies and tetramethylbenzidine (TMB1) substrate. The reaction was stopped with 0.18 M sulfuric acid ($H_2SO_4$) and absorbance was read at 450 nm in an EnVision multilabel reader (PerkinElmer). Table 8 shows similar reactivity for human and cynomolgus monkey IFNβ, while reactivity to rabbit IFNβ is 200 times lower. There was no detectable binding to rat or mouse IFNβ, or to the three nearest human homologs or IFNγ (type II).

TABLE 8

Reactivity of CTI-AFI to IFNβ orthologs and nearest type I homologs and IFNγ as measured by ELISA

| Target | Homology (%) | CTI-AF1 $EC_{50}$ (pM) |
|---|---|---|
| Cross-species binding | | |
| Human IFNβ | 100 | 15.14 |
| Cynomolgus monkey IFNβ | 95.7 | 24.67 |
| Rabbit IFNβ | 56.1 | 2948 |
| Rat IFNβ | 48.6 | No binding |
| Mouse IFNβ | 47.5 | No binding |
| Cross-reactivity | | |
| Human IFNα2 | 30.2 | No binding |
| Human IFNα17 | 38.2 | No binding |
| Human IFNω | 29.0 | No binding |
| Human IFNγ | 13.2 | No binding |

"No binding": when the absorbance at 450 nm was < 2x the absorbance of the blank control wells.

Figure 8A:
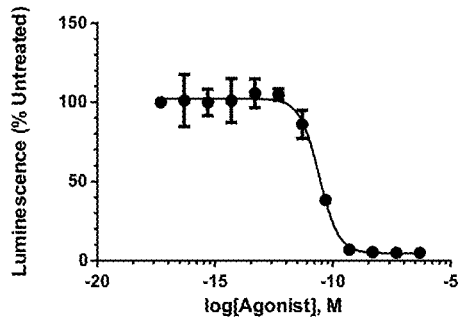
FIGS. 8A-8B demonstrate that CTI-AF1 is a potent neutralizer of IFNβ induced signaling in multiple assays.

Two in vitro assays were used to demonstrate CTI-AF1 dependent inhibition of IFNβ induced signals. Firstly, HEK293 cells stably transduced with a human ISRE luciferase reporter were used as a measure of IFNβ dependent gene expression; on day 1, 20,000 HEK293 ISRE-Luc (IFNβ responsive luciferase reporter) cells were plated in 100 µL of DMEM containing 10% fetal bovine serum (FBS) per well in tissue culture treated 96 well plates. Antibody solutions were prepared as 2x stocks starting at a top concentration of 1 µM in DMEM/10% FBS. An 11 point, 10-fold dilution series was made with media. A 20x stock of IFNβ (28 nM, final assay concentration was 1.4 nM, the $EC_{50}$) was prepared in media and added to the antibody titration stocks to a final 2x concentration. The antibody:IFNβ solutions were incubated for 2 hours at 37° C., then 100 µL was added per well and plates were cultured overnight at 37° C. On day 3, a 150 µg/mL solution of Beetle Luciferine, potassium salt was prepared and 20 µL/well was added and plates were incubated for 15 minutes at 37° C. Luminesence was read on an EnVision multilabel plate reader. FIG. 8A shows CTI-AF1 dose-dependent inhibition of IFNβ induced luciferase activity with an $IC_{50}$ of 28.8±7.6 µM.

Figure 8B:
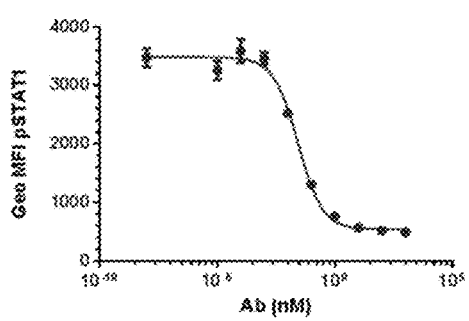

Secondly, CTI-AF1 mediated inhibition of IFNβ induced STAT1 phosphorylation was evaluated by phosflow. U937 cells, a human monocytic cell line, were grown in RPMI 1640 containing 10% FBS and 2 mM Glutamax (cRPMI). Antibody stocks were made at 4×, with a top concentration of 4 µM (final top concentration was 1 µM) and a 12 point, 10-fold dilution series was made in cRPMI; 25 µL was added/well in a u-bottom 96 well tissue culture plate. An equal volume of 4×IFNβ (200 µM, final concentration was 50 µM, $EC_{90}$) was added to the antibody stocks and incubated for 2 hours at 37° C. Control wells included media alone (no stimulation background pSTAT1 expression) and 50 µM IFNβ only (maximum pSTAT1 signal). U937 cells were harvested, centrifuged for 5 min at 1500 rpm, room temperature and then resuspended at a concentration of $2×10^6$/mL in cRPMI warmed to 37° C.; 50 µL of cell suspension was added per well and plates placed at 37° C. for 15 minutes. Next, 100 µL of pre-warmed cytofix buffer was added and plates were placed back at 37° C. for 15 minutes. Plates were removed and centrifuged as described above. Media was removed from the plates, cells resuspended and washed in 200 µL of PBS and centrifuged again. Media was removed again, then cells were resuspended in 100 µL of permeabilization buffer IV and incubated at room temperature for 15 minutes. At the end of the incubation, cells were centrifuged and washed as described above. After the PBS wash, cells were resuspended in 100 µL of PBS/5% FBS; 5 µL of TruStain FcX/well was added and plates were incubated for 10 min at 4° C. Ten microliters of Alexa Fluor 674 (AF647) conjugated anti-phospho STAT1 antibody was added per well and incubated for 20 min at 4° C. After incubation, 120 µL of FACS buffer was added per well and plates were centrifuged as described above. The wash was repeated with 220 µL of FACS buffer and cells were resuspended in 120 uL of FACS buffer. A Fortessa cytometer was used to acquire the data and analysis was performed using FlowJo software. The geometric mean fluorescence intensity (Geo MFI) in the AF647 channel was calculated and prism software was used to calculate the $IC_{50}$. CTI-AF1 is a potent neutralizer of human IFNβ with an $IC_{50}$ of 29.8±6.9 µM (FIG. 8B).

Figure 9:
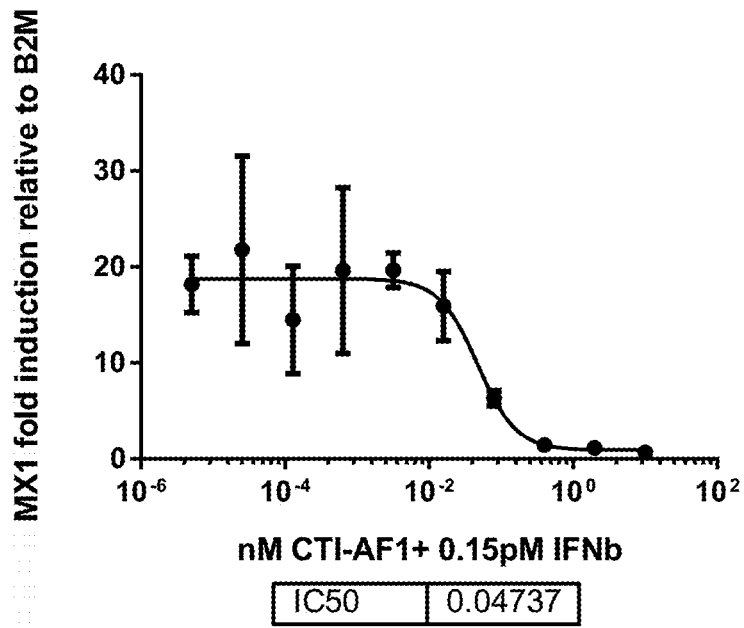
FIG. 9 demonstrates that CTI-AF1 neutralized expression of IFN stimulated gene Mx1 (MxA) in primary human dermal fibroblasts (HDF). There are a number of genes that are known to be expressed in response to stimulation with IFNs, IFN stimulated genes (ISG). Mx1 (MxA) is well characterized as a type I IFN ISG. Mx1 (MxA) gene expression after stimulation with recombinant IFNβ was evaluated in primary HDF in the presence or absence of indicated amounts of CTI-AF1. Cells were stimulated for 5 hours then RNA was isolated. RNA was converted into cDNA and quantitative PCR (qPCR) was performed to determine the level of Mx1 (MxA) expression and B2 M was used as a control. Data are presented as fold induction; a dose-dependent inhibition of Mx1 (MxA) gene expression was seen indicating neutralization of IFNβ signaling.

To evaluate the ability of CTI-AF1 to neutralize recombinant IFNβ induced MxA (Mx1) gene expression normal human dermal fibroblasts (HDF) were plated in a T-150 flask in fibroblast culture medium. To set up the assay, cells were dislodged from the flask using trypsin/EDTA solution and plated in a 48 well plate with three wells assigned per experimental condition. On day 3, the cells were stimulated for 5 hours with culture medium spiked with 0.15 µM IFNβ that was pre-incubated for 2 hours with or without dilutions of CTI-AF1 ranging from 10 nM to 0.016 nM. A combination of 0.15 µM IFNβ and 50 nM of isotype control antibody was used as a negative control for the experiment. After 5 hours, cells were harvested, RNA was isolated using RNeasy micro kit and cDNA synthesized using high capacity cDNA reverse transcription kit. Taqman real time PCR analyses were performed in a Vii A7 system (Thermo Fisher) using human gene specific primer probes for Mx1 and 82 M. The relative quantification (fold change) was calculated from the resultant $C_t$ values using the ΔΔCt method as follows: for each condition, $C_t$ values of the endogenous control gene (82 M) were subtracted from respective $C_t$ values for target gene (Mx1). This was followed by normalization against the untreated sample to calculate the ΔΔCt values, which were subsequently used to calculate the fold change ($2^{-\Delta\Delta C_t}$). The isotype negative control antibody had no impact on MxA (Mx1) expression; however, in the presence of CTI-AF1, a dose-dependent inhibition of gene transcription was seen with an $IC_{50}$ of 29.4±23.5 pM (FIG. 9).

Figure 10A:
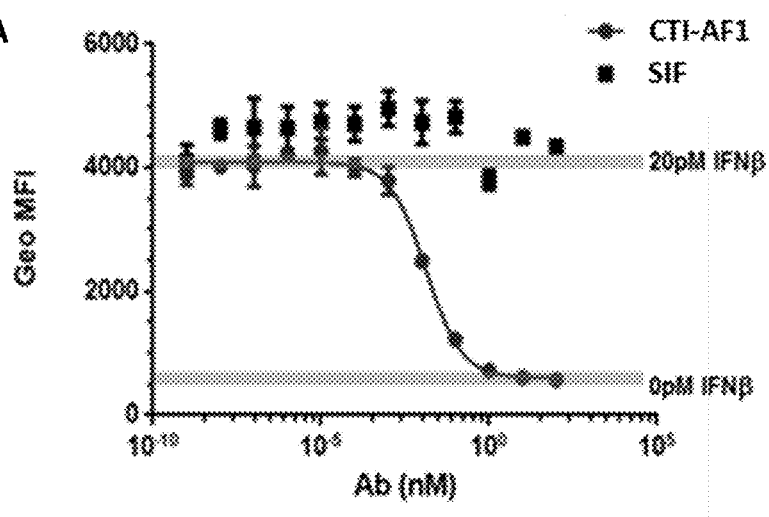
FIGS. 10A-10B demonstrate that CTI-AF1 specifically neutralized IFNβ. U937 cells were stimulated with either IFNβ (FIG. 10A) or IFNα (FIG. 10B) for 15 minutes in the presence of neutralizing antibodies to IFNβ (CTI-AF1) or IFNα (sifalimumab, SIF). CTI-AF1 inhibited IFNβ dependent STAT1 phosphorylation (panel A), but had no impact on IFNα-induced STAT1 phosphorylation (panel B). As a control, a neutralizing anti-IFNα (SIF) was used in conjunction with IFNα stimulation to demonstrate IFNα dependent STAT1 phosphorylation could be inhibited.
Figure 10B:
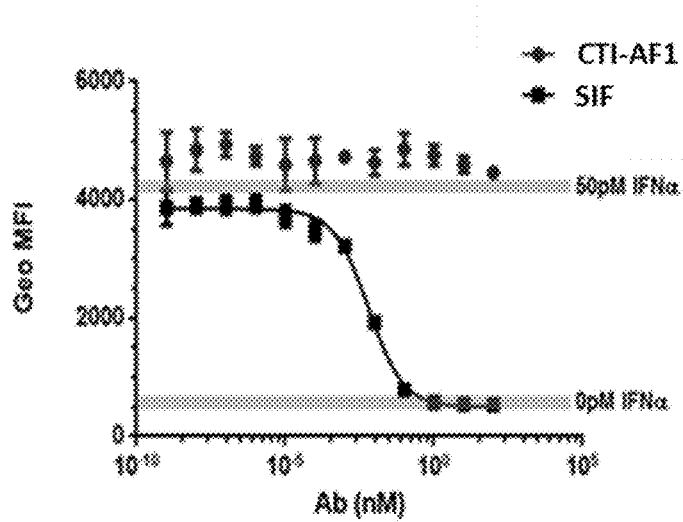
Figure 16A:
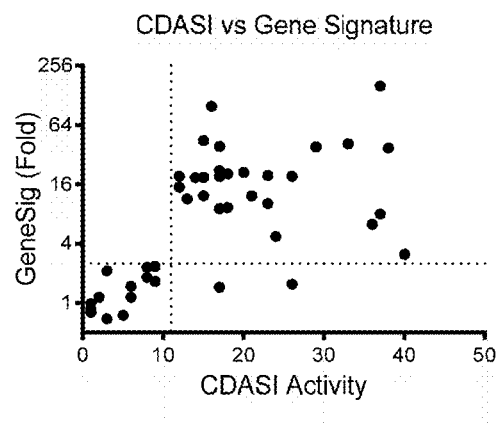
FIG. 16A shows the relationship between cutaneous dermatomyositis disease area and severity index (CDASI) activity and a blood 10-gene signature score. CDASI activity score correlates with an elevated 10-gene blood IRG "signature" (Spearman rank correlation r=0.61; p<0.0001).
Figure 16B:
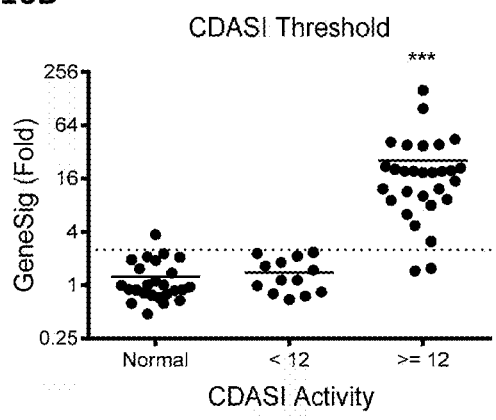
FIG. 16B shows a strong threshold effect observed with a CDASI cutoff of 12 that is associated with IRG signature cutoff of 3-fold (P=0.0004, Mann-Whitney test).

The specificity of CTI-AF1 neutralization was evaluated by using the same pSTAT assay as described earlier for FIG. 8B, however, U937 cells were stimulated with either a final concentration of 20 pM IFNβ or 50 pM IFNα. The different concentrations of type I IFNs were selected to provide a similar level of STAT1 phosphorylation as IFNα is a less potent activator of IFNAR signaling. A similar 12 point, 10-fold dilution series was made with sifalimumab (SIF) as a positive control for IFNα neutralization. As can be seen, CTI-AF1 specifically inhibited IFNβ induced STAT1 phosphorylation, but did not inhibit phosphorylation induced by IFNα (FIGS. 10 A and B, respectively). A single experiment was conducted using either IFNω (at 100 µM) or IFNα14 (at 4 pM) and CTI-AF1 had no effect on IFNω or IFNα14 induced STAT1 phosphorylation.

To ensure that CTI-AF1 neutralized endogenously expressed IFNβ, normal human dermal fibroblasts were seeded in a 48 well plate with three wells assigned per experimental condition. On day 3, cells were stimulated with or without a combination of 1 µg/mL poly I:C and dilutions of CTI-AF1 (dose range: 50 pM-100 nM) or 100 nM sifalumumab. After 2.5 and 24 hours, cells were harvested, RNA isolated using RNeasy micro kit and cDNA synthesized using high capacity cDNA reverse transcription kit. Taqman real time PCR and fold change calculations were performed as described above (FIG. 9). While the amount of IFNβ induced by poly I:C stimulation was unknown, a dose-dependent inhibition of MxA (Mx1) expression was seen in the presence of CTI-AF1 (FIG. 11).

Example 4. Translational Pharmacology

The PK/PD relationship for IFNβ in dermatomyositis (DM) has not been defined. There are no relevant translatable preclinical models available for DM and the preclinical efficacious concentration (Ceff) is not understood. A type 1 Interferon gene signature will be used clinically as a mechanistic biomarker of pharmacology modulation. Type 1 Interferon genes are typically elevated in DM and SLE patients and the mean fold-change of the type 1 Interferon gene signature has been used previously in clinical studies for anti-IFNα (sifalimumab and rontalizumab) and anti-IFNAR (anifrolumab) mAbs. However, a quantitative understanding of the gene signature modulation has not been established and the relationship between in vivo exposure, target engagement, downstream pharmacology and efficacy over time is not understood. Human efficacious dose feasibility projections are based on the ability of CTI-AF1 to neutralize >95% of IFNβ in skin.

An LC\MS\MS assay is used to measure total IFNβ in clinical serum and tissue biopsies, and in combination with CTI-AF1 clinical PK and $K_D$, is used to assess and confirm target engagement. Type 1 IFN gene signature in blood and skin, as well as IP-10 (CXCL10), are assessed as mechanistic biomarkers. In a subsequent Proof of Mechanism (PoM)/Early Signal of Efficacy (ESoE) study in DM patients, cutaneous dermatomyositis disease area and severity index (CDASI) is used as the primary endpoint (outcome biomarker) in addition to any relevant mechanistic biomarkers.

Pharmacokinetics-Pharmacodynamics Relationship and Human Dose

The pharmacokinetic and pharmacodynamic (PK/PD) relationships between antibody drug exposure and IFNβ for CTI-AF1 have been simulated using reported PK parameters for typical IgG$_1$ therapeutics, IFNβ-CTI-AF1 equilibrium binding constant, IFNβ concentrations in skin and serum, and IFNβ turnover half-life.

Figure 17:
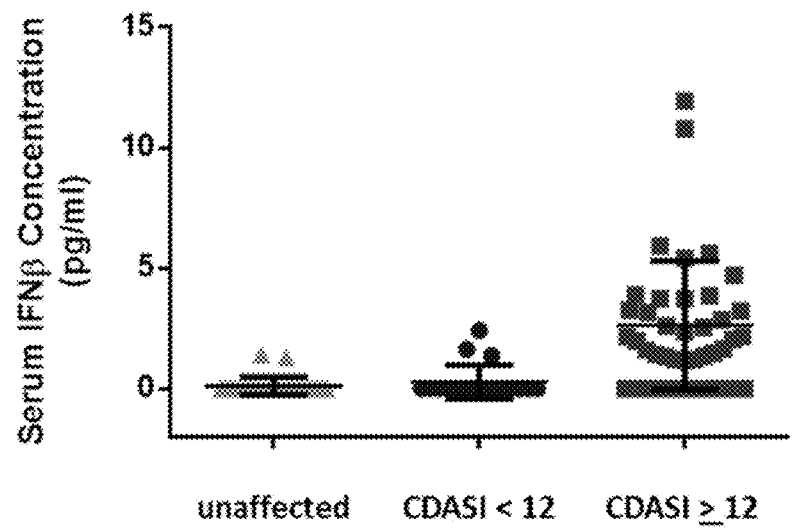
FIG. 17 shows serum samples from 25 normal (unaffected) donors, 19 DM donors with a CDASI of <12, and 38 DM donors with a CDASI of ≥12 analyzed for the presence of IFNβ protein using a high-sensitivity ELISA kit (PBL Assay Science) (Wilcoxon test 'unaffected vs CDASI <12' p=0.39; Wilcoxon test 'unaffected vs CDASI p≥12' p<0.0001).
Figure 18A:
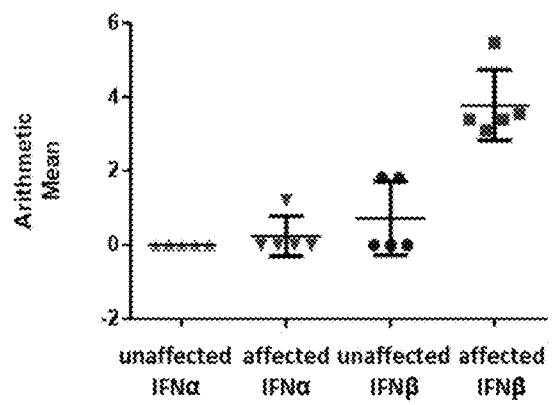
FIGS. 18A-18B show levels of IFNα or IFNβ mRNA (FIG. 18A) or an IRG signature in unaffected versus affected skin samples (FIG. 18B) in paired skin biopsies (i.e., unaffected and affected tissue) collected from 5 DM patients and evaluated by a custom Type I IFN TaqMan Low Density Array (TLDA) (96 assay array). Each data point represents the average of 2 independent qPCR reactions per sample; mean±SEM. Panel A: Signed Rank test p-value "unaffected IFNβ vs affected IFNβ"=0.06; Signed Rank test p-value "unaffected IFNα vs affected IFNα"=1.0. Panel B: Signed Rank test p-value "unaffected vs affected"=0.002.
Figure 18B:
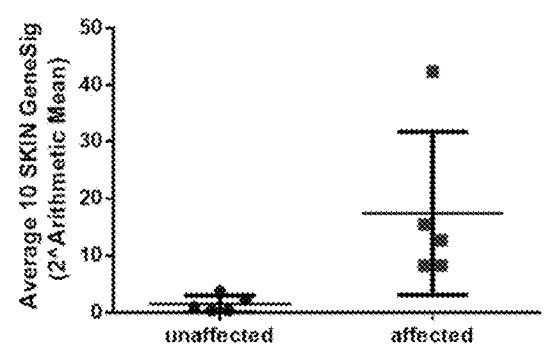
Figure 19:
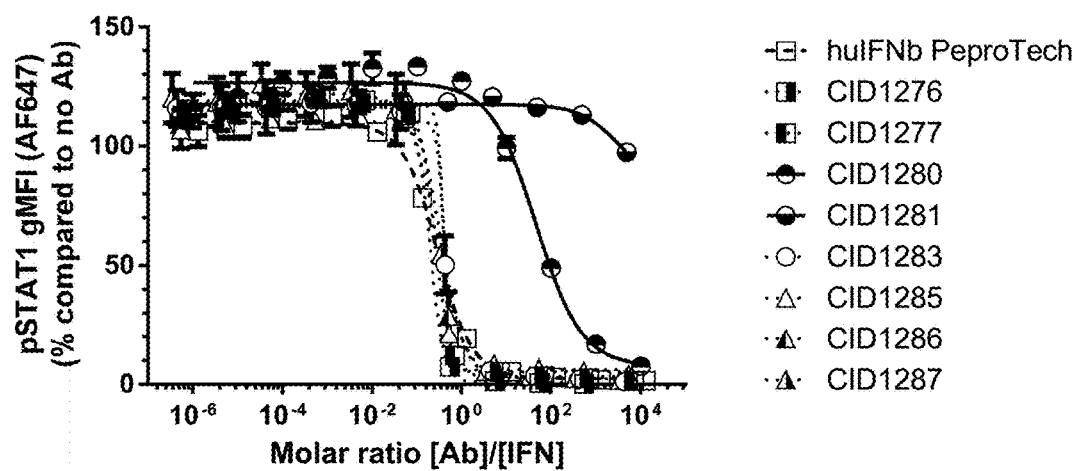
FIG. 19 is a graph showing dose-dependent CTI-AF1 inhibition of hybrid IFNα/β proteins. Absence (CID1281) or decreased (CID1280) inhibition of IFN-induced STAT1 phosphorylation indicates that insertion of the IFNα sequence has disrupted the epitope within IFNβ that is recognized byCTI-AF1.
Figure 20A:
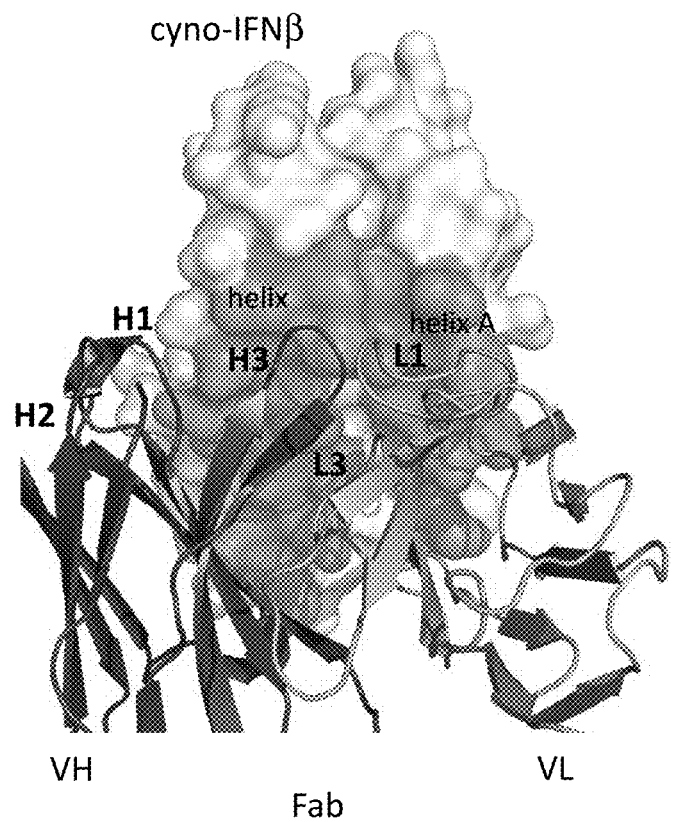
FIGS. 20A-20B shows the co-crystal structure of cyno-IFNβ and Fab of CTI-AF1. Binding epitope residues are depicted in grey in FIG. 20A, and binding paratope residues are depicted in grey in FIG. 20B.
Figure 20B:
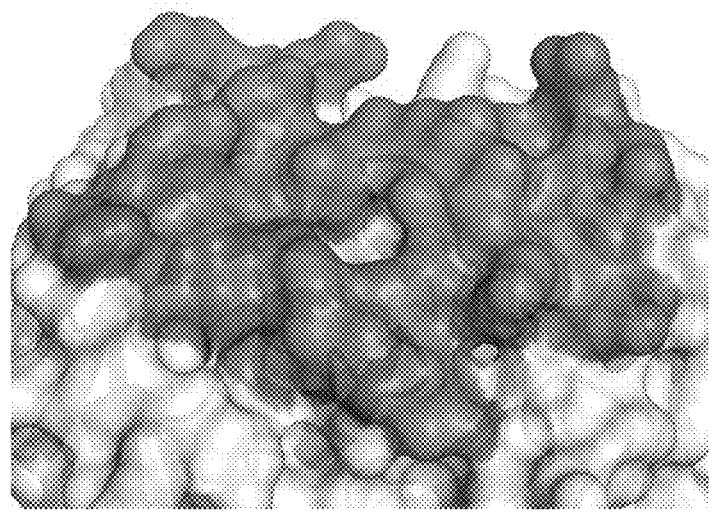

A "Site-of-Action" PK/PD model was used to predict the coverage of IFNβ in DM patients. An IFNβ coverage of >95% at trough was considered necessary to achieve efficacy. Skin interstitial concentrations of CTI-AF1 were assumed to be 30% of serum concentrations. The binding affinity of CTI-AF1 to IFNβ determined by SPR (Biacore $K_D$=36.7 μM) was used for PK/PD modeling. Consistent with this, in cell-based functional assays, CTI-AF1 showed potent neutralization of IFNβ-induced STAT1 phosphorylation ($IC_{50}$ 29.8 μM).

The median IFNβ concentration in DM patient serum was 3 pg/mL (N=26); however, the IFNβ concentration in DM patient skin is not known. Therefore, in the model, the impact of IFNβ skin:plasma ratio was investigated at ratios of 10 and 100. Since this is a sensitive parameter for the model, these ratios were used as proposed boundary conditions to demonstrate the impact of the skin:plasma ratio on target coverage.

The in vivo half-life of IFNβ turnover was estimated by fitting a 3-compartmental model to the human PK data for IFNβ1α, which included 3 IV doses. This fitting resulted in two different half-lives for IFNβ turnover which are considered most relevant, depending on the phase and compartments considered ranging from 3 minutes (based on the initial phase) to 126 minutes (based on the effective half-life). To increase confidence in this model parameter, an IFNβ assay for cynomolgus monkey serum was developed for use in cynomolgus monkey.

The IFNβ skin:plasma ratio and the IFNβ turnover rate are sensitive parameters for the PK/PD model. Thus, the human efficacious dose feasibility assessment was performed using the ranges described above for both IFNβ skin:plasma ratio and IFNβ turnover rate. Example assessments for two likely clinical ESoE dose regimens are shown in FIGS. 12 A-D (IV Q4W) and FIGS. 13A-D (SC Q1W). CTI-AF1 solubility of 150 mg/mL would enable a clinical dose of 2 mg/kg, as it can be delivered via a 1 mL injection pen. Hence a dose of 2 mg/kg was used for the dose feasibility assessments below.

FIGS. 12A-D show that at a dose of 2 mg/kg IV Q4W, irrespective of IFNβ skin:plasma ratio, only the 126 min half-life for IFNβ predicts >95% IFNβ coverage in skin. If the half-life of IFNβ was 3 min, >95% IFNβ coverage in skin is predicted to require doses higher than 2 mg/kg. FIGS. 13A-D show that at a dose of 2 mg/kg SC Q1W, irrespective of IFNβ skin:plasma ratio, the 126 min half-life for IFNβ predicts >95% IFNβ coverage in skin. If the half-life of IFNβ was 3 min, then only the IFNβ skin:plasma ratio of 100 will result in >95% IFNβ coverage in skin at 2 mg/kg. By contrast, if IFNβ skin:plasma ratio is 10, achieving >95% coverage will require doses higher than 2 mg/kg.

Human PK/Exposure

Based on the pharmacokinetic profiles of CTI-AF1 in cynomolgus monkey, the pharmacokinetics of CTI-AF1 in human are expected to be similar to the reported values for a typical $IgG_1$ therapeutic. The 2-compartment pharmacokinetic parameter values are summarized in Table 9. Simulated concentration-time profiles of CTI-AF1 at projected efficacious dose levels are depicted in the top panels of FIGS. 12A-D and 13A-D.

TABLE 9

Projected Pharmacokinetic Parameters of CTI-AF1 in Human

| Parameter | Definition | Projection |
|---|---|---|
| CL | central clearance | 0.00258 mL/min/kg |
| V1 | central volume | 43.7 mL/kg |
| CLD | distribution clearance | 0.00565 mL/min/kg |
| V2 | peripheral volume | 44.3 mL/kg |
| Ka | absorption rate constant for SC dosing | 0.000181/min |
| F_sc | SC bioavailability | 60% |
| Vdss | steady-state volume of distribution | 88 mL/kg |
| $T_{1/2}$ | terminal half life | 19 days |

Nonclinical Pharmacokinetics

IV and SC pharmacokinetics of CTI-AF1 have been assessed in cynomolgus monkeys using data from a single-dose exploratory toxicity study. Mean serum pharmacokinetic parameter values for cynomolgus monkeys are summarized in Table 10 and mean serum concentrations of CTI-AF1 are shown in FIG. 14.

TABLE 10

Summary Table of CTI-AF1 Pharmacokinetics in Cynomolgus Monkeys

| Dose (mg/kg) | Route | Cmax (μg/mL) | AUCinf (μg*hr/mL) | CL (mL/h/kg) | $V_{ss}$ (L/kg) | $T_{1/2}$ (h) | F (%) |
|---|---|---|---|---|---|---|---|
| 10 | SC | 97.7 | 50000 | n/a | n/a | 379 | 87.3 |
| 10 | IV | 248 | 54900 | 0.183 | 0.0823 | 337 | n/a |
| 200 | IV | 4980 | 1000000 | 0.209 | 0.0747 | 273 | n/a |

Mean N = 2 monkeys/group, 1 male and 1 female

Example 5. IFNβ as a Target for SLE and DM

There is increasing evidence that IFN production is linked to SLE and other rheumatic diseases, such as DM. Moreover, the perpetuation of the SLE disease process likely involves further production of type I IFNs and a vicious pathogenic cycle.

DM is a rare autoimmune disease (about 20,000 patients in the U. S.) characterized by inflammation of skeletal muscle and skin, and, concomitantly, skeletal muscle weakness and skin rash. DM is typically associated with autoantibodies, and the pathogenesis of the disease may involve sequential binding of these autoantibodies to an endothelial autoantigen, triggering complement activation and vascular inflammation, ultimately leading to perifascicular atrophy.

As shown in FIGS. 16 A-B, data indicated an association of type I interferon-regulated gene (IRG) transcript "signature" in DM blood with skin rash activity, as measured by the cutaneous dermatomyositis disease area and severity index (CDASI). The highly IFNβ-inducible gene MxA (Mx1) is expressed in DM perifascicular myofibers and capillaries, and blood serum IFNβ—but not IFNα or IFNω—is associated with DM, but not with other inflammatory myopathies or normal sera. These data support the notion that injury to capillaries, myofibers and skin in DM results from a pathogenic overproduction of IFNβ message and protein. Data have also demonstrated an association between CDASI scores and serum levels of IFNβ protein (FIG. 17). Analyses of paired skin biopsies indicate the presence of both IFNβ mRNA and upregulation of an IRG signature only in affected tissue (FIGS. 18 A-B). Taken together, these data strongly suggest that DM is an IFNβ-driven disease.

Given that in many tissue contexts IFNβ production may precede IFNα production and initiate a pathogenic elevation of IRG signature expression, together with the notion that DM may be a largely IFNβ-driven disease, it is believed that DM and SLE share many pathogenic features and attributes. Indeed, skin lesions of DM are difficult if not impossible to distinguish histologically from those of SLE, and a diagnosis of DM skin lesions typically requires clinical determination of increased CD4+ and CXCR3+ cell types and endothelial expression of Mx1. Moreover, both DM and SLE are characterized by B cell activation and autoantibody mediated inflammation and tissue destruction.

TABLE 11

Sequences of anti-IFN antibodies

| Seq ID | Ab Name | | Sequences (CDR-L1, CDR-L2, CDR-L3, CDR-H1, CDR-H2, and CDR-H3 underlined when applicable)) |
|---|---|---|---|
| 1 | CTI-AF1 | VL | DIQMTQSPSSLSASVGDRVTITCRTSQDIGNYLNWYQQKPGKAFKLLIYSTSRLHSG VPSRFSGSGSGTDFTLTISSLQPEDFATYYCQQGIILPITFGGGTKVEIK (CDR-L1, CDR-L2, CDR-L3: SEQ ID NOs 34, 35, and 36, respectively) |
| 2 | CTI-AF2 | VL | DIQMTQSPSSLSASVGDRVTITCRTSQDIGNYLNWYQQKPGKAFKLLIYSTSRLHSG VPSRFSGSGSGTDFTLTISSLQPEDFATYYCQQGIVLPITFGGGTKVEIK |
| 3 | CTI-AF3 | VL | DIQMTQSPSSLSASVGDRVTITCRTSQDISNYLNWYQQKPGKAFKLLIFSTSRLHSG VPSRFSGSGSGTDFTLTISSLQPEDFATYYCQQGIVLPITFGGGTKVEIK |
| 4 | CTI-AF4 | VL | DIQMTQSPSSLSASVGDRVTITCRTSQDISSYLNWYQQKPGKAFKLLIYSTSRLHSG VPSRFSGSGSGTDFTLTISSLQPEDFATYYCQQGIVLPITFGGGTKVEIK |
| 5 | CTI-AF5 | VL | DIQMTQSPSSLSASVGDRVTITCRTSQDISNYLNWYQQKPGKAFKLLIYTTSRLRSG VPSRFSGSGSGTDFTLTISSLQPEDFATYYCQQGIVLPITFGGGTKVEIK |
| 6 | CTI-AF6 | VL | DIQMTQSPSSLSASVGDRVTITCRTSQDIDNFLQWYQQKPGKAFKLLIYSTSRLHSG VPSRFSGSGSGTDFTLTISSLQPEDFATYYCQQGIVLPITFGGGTKVEIK |
| 7 | CTI-AF7 | VL | DIQMTQSPSSLSASVGDRVTITCRTSQDISNYLNWYQQKPGKAFKLLIYSTSKLHSG VPSRFSGSGSGTDFTLTISSLQPEDFATYYCQQGIVLPITFGGGTKVEIK |
| 8 | CTI-AF8 | VL | DIQMTQSPSSLSASVGDRVTITCRTSQDIGNYLNWYQQKPGKAFKLLIYSTSRLHSG VPSRFSGSGSGTDFTLTISSLQPEDFATYYCQQSTILPLTFGGGTKVEIK |
| 9 | CTI-AF9 | VL | DIQMTQSPSSLSASVGDRVTITCRTSQDISNYLNWYQQKPGKAFKLLIFSTSRLHSG VPSRFSGSGSGTDFTLTISSLQPEDFATYYCQQSTILPLTFGGGTKVEIK |
| 10 | CTI-AF10 | VL | DIQMTQSPSSLSASVGDRVTITCRTSQDISSYLNWYQQKPGKAFKLLIYSTSRLHSG VPSRFSGSGSGTDFTLTISSLQPEDFATYYCQQSTILPLTFGGGTKVEIK |
| 11 | CTI-AF11 | VL | DIQMTQSPSSLSASVGDRVTITCRTSQDISNYLNWYQQKPGKAFKLLIYTTSRLRSG VPSRFSGSGSGTDFTLTISSLQPEDFATYYCQQSTILPLTFGGGTKVEIK |
| 12 | CTI-AF12 | VL | DIQMTQSPSSLSASVGDRVTITCRTSQDIDNFLQWYQQKPGKAFKLLIYSTSRLHSG VPSRFSGSGSGTDFTLTISSLQPEDFATYYCQQSTILPLTFGGGTKVEIK |
| 13 | CTI-AF13 | VL | DIQMTQSPSSLSASVGDRVTITCRTSQDISNYLNWYQQKPGKAFKLLIYSTSKLHSG VPSRFSGSGSGTDFTLTISSLQPEDFATYYCQQSTILPLTFGGGTKVEIK |
| 14 | CTI-AF14 | VL | DIQMTQSPSSLSASVGDRVTITCRTSQDISNYLNWYQQKPGKAFKLLIFSTSRLHSG VPSRFSGSGSGTDFTLTISSLQPEDFATYYCQQGIILPITFGGGTKVEIK |
| 15 | CTI-AF15 | VL | DIQMTQSPSSLSASVGDRVTITCRTSQDISSYLNWYQQKPGKAFKLLIYSTSRLHSG VPSRFSGSGSGTDFTLTISSLQPEDFATYYCQQGIILPITFGGGTKVEIK |
| 16 | CTI-AF16 | VL | DIQMTQSPSSLSASVGDRVTITCRTSQDISNYLNWYQQKPGKAFKLLIYTTSRLRSG VPSRFSGSGSGTDFTLTISSLQPEDFATYYCQQGIILPITFGGGTKVEIK |
| 17 | CTI-AF17 | VL | DIQMTQSPSSLSASVGDRVTITCRTSQDIDNFLQWYQQKPGKAFKLLIYSTSRLHSG VPSRFSGSGSGTDFTLTISSLQPEDFATYYCQQGIILPITFGGGTKVEIK |

TABLE 11-continued

Sequences of anti-IFN antibodies

| Seq ID | Ab Name | | Sequences (CDR-L1, CDR-L2, CDR-L3, CDR-H1, CDR-H2, and CDR-H3 underlined when applicable)) |
|---|---|---|---|
| 18 | CTI-AF18 | VL | DIQMTQSPSSLSASVGDRVTITCRTSQDISNYLNWYQQKPGKAFKLLIYSTSKLHSG VPSRFSGSGSGTDFTLTISSLQPEDFATYYCQQGIILPITFGGGTKVEIK |
| 19 | CTI-AF19 | VL | DIQMTQSPSSLSASVGDRVTITCRTSQDIGNYLNWYQQKPGKAFKLLIFSTSRLHSG VPSRFSGSGSGTDFTLTISSLQPEDFATYYCQQGIVLPITFGGGTKVEIK |
| 20 | CTI-AF20 | VL | DIQMTQSPSSLSASVGDRVTITCRTSQDISSYLNWYQQKPGKAFKLLIYTTSRLRSG VPSRFSGSGSGTDFTLTISSLQPEDFATYYCQQGIVLPITFGGGTKVEIK |
| 21 | CTI-AF21 | VL | DIQMTQSPSSLSASVGDRVTITCRTSQDIDNFLQWYQQKPGKAFKLLIFSTSKLHSG VPSRFSGSGSGTDFTLTISSLQPEDFATYYCQQGIVLPITFGGGTKVEIK |
| 22 | CTI-AF22 | VL | DIQMTQSPSSLSASVGDRVTITCRTSQDIGNYLNWYQQKPGKAFKLLIFSTSRLHSG VPSRFSGSGSGTDFTLTISSLQPEDFATYYCQQSTILPLTFGGGTKVEIK |
| 23 | CTI-AF23 | VL | DIQMTQSPSSLSASVGDRVTITCRTSQDISSYLNWYQQKPGKAFKLLIYTTSRLRSG VPSRFSGSGSGTDFTLTISSLQPEDFATYYCQQSTILPLTFGGGTKVEIK |
| 24 | CTI-AF24 | VL | DIQMTQSPSSLSASVGDRVTITCRTSQDIDNFLQWYQQKPGKAFKLLIFSTSKLHSG VPSRFSGSGSGTDFTLTISSLQPEDFATYYCQQSTILPLTFGGGTKVEIK |
| 25 | CTI-AF25 | VL | DIQMTQSPSSLSASVGDRVTITCRTSQDIGNYLNWYQQKPGKAFKLLIFSTSRLHSG VPSRFSGSGSGTDFTLTISSLQPEDFATYYCQQGIILPITFGGGTKVEIK |
| 26 | CTI-AF26 | VL | DIQMTQSPSSLSASVGDRVTITCRTSQDISSYLNWYQQKPGKAFKLLIYTTSRLRSG VPSRFSGSGSGTDFTLTISSLQPEDFATYYCQQGIILPITFGGGTKVEIK |
| 27 | CTI-AF27 | VL | DIQMTQSPSSLSASVGDRVTITCRTSQDIDNFLQWYQQKPGKAFKLLIFSTSKLHSG VPSRFSGSGSGTDFTLTISSLQPEDFATYYCQQGIILPITFGGGTKVEIK |
| 28 | CTI-AF1 to ACT-AF27 | VH | QVQLVQSGAEVKKPGSSVKVSCKASGYTFSRYWMHWVRQAPGQGLEWMGHIDPSDSY TYYNQKFKGRVTITADESTSTAYMELSSLRSEDTAVYYCARWDYGNLLFEYWGQGTL VTVSS (CDR-H1, CDR-H2, CDR-H3: SEQ ID NOs 37, 38, and 39, respectively) |
| 29 | All CTI-AFs | CH | ASTKGPSVFPLAPSSKSTSGGTAALGCLVKDYFPEPVTVSWNSGALTSGVHTFPAVL QSSGLYSLSSVVTVPSSSLGTQTYICNVNHKPSNTKVDKKVEPKSCDKTHTCPPCPA PEAAGAPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPRE PQVYTLPPSREEMTKNQVSLTCLVKGFYPSDIAVEWESNGQPENNYKTTPPVLDSDG SFFLYSKLTVDKSRWQQGNVFSCSVMHEALHNHYTQKSLSLSPG(K) |
| 30 | All CTI-AFs | CL | RTVAAPSVFIFPPSDEQLKSGTASVVCLLNNFYPREAKVQWKVDNALQSGNSQESVT EQDSKDSTYSLSSTLTLSKADYEKHKVYACEVTHQGLSSPVTKSFNRGEC |
| 32 | CTI-AF1 | Light chain | DIQMTQSPSSLSASVGDRVTITCRTSQDIGNYLNWYQQKPGKAFKLLIYSTSRLHSGV PSRFSGSGSGTDFTLTISSLQPEDFATYYCQQGIILPITFGGGTKVEIKRTVAAPSVF IFPPSDEQLKSGTASVVCLLNNFYPREAKVQWKVDNALQSGNSQESVTEQDSKDSTYS LSSTLTLSKADYEKHKVYACEVTHQGLSSPVTKSFNRGEC |
| 33 | CTI-AF1 | Heavy chain | QVQLVQSGAEVKKPGSSVKVSCKASGYTFSRYWMHWVRQAPGQGLEWMGHIDPSDSY TYYNQKFKGRVTITADESTSTAYMELSSLRSEDTAVYYCARWDYGNLLFEYWGQGTL VTVSSASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKKVEPKSCDKTHTC PPCPAPEAAGAPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAPIEKTISKAK GQPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPG(K) |
| 34 | CTI-AF1 | CDR-L1 | RTSQDIGNYLN |
| 35 | CTI-AF1 | CDR-L2 | STSRLHS |
| 36 | CTI-AF1 | CDR-L3 | QQGIILPIT |
| 37 | CTI-AF1 | CDR-H1 | GYTFSRYWMH |

TABLE 11-continued

Sequences of anti-IFN antibodies

| Seq ID | Ab Name | | Sequences (CDR-L1, CDR-L2, CDR-L3, CDR-H1, CDR-H2, and CDR-H3 underlined when applicable)) |
|---|---|---|---|
| 38 | CTI-AF1 | CDR-H2 | HIDPSDSYTYYNQKFKG |
| 39 | CTI-AF1 | CDR-H3 | WDYGNLLFEY |
| 166 | CTI-AF1 | VH nucleic acid | CAGGTGCAGCTGGTGCAGAGCGGCGCCGAGGTGAAGAAGCCCGGCAGCAGCGTGAAG GTGAGCTGCAAGGCCAGCGGCTACACCTTCAGCCGGTACTGGATGCACTGGGTGCGG CAGGCCCCCGGCCAGGGCCTGGAGTGGATGGGCCACATCGACCCCAGCGACAGCTAC ACCTACTACAACCAGAAGTTCAAGGGCCGGGTGACCATCACCGCCGACGAGAGCACC AGCACCGCCTACATGGAGCTGAGCAGCCTGCGGAGCGAGGACACCGCCGTGTACTAC TGCGCCCGGTGGGACTACGGCAACCTGCTGTTCGAGTACTGGGGCCAGGGCACCCTG GTGACCGTCTCGAGC |
| 167 | CTI-AF1 | VL nucleic acid | GACATCCAGATGACCCAGAGCCCCAGCAGCCTGAGCGCCAGCGTGGGCGACCGGGTG ACCATCACCTGCCGGACCAGCCAGGACATCGGCAACTACCTGAACTGGTACCAGCAG AAGCCCGGCAAGGCCTTCAAGCTGCTGATCTACAGCACCAGCCGGCTGCACAGCGGC GTGCCCAGCCGGTTCAGCGGCAGCGGCAGCGGCACCGACTTCACCCTGACCATCAGC AGCCTGCAGCCCGAGGACTTCGCCACCTACTACTGCCAGCAGGGGATTATTTTGCCC ATTACCTTCGGCGGCGGCACCAAGGTGGAGATCAAG |

Example 6. Epitope Mapping

To elucidate the epitope recognized by CTI-AF1, hybrid IFNβ proteins were made where selected portions of IFNβ sequences were replaced with IFNα sequence. CTI-AF1 specifically neutralizes IFNβ but not IFNα, therefore the inability of CTI-AF1 to neutralize a given hybrid protein would indicate loss of the epitope. Hybrid proteins were produced, purified and ability to induce STAT1 phosphorylation was confirmed (Table 12).

TABLE 12 sequences of hybrid IFN proteins

| Seq ID | Hybrid IFN name | Sequences (mutated residues underlined) |
|---|---|---|
| 41 | Human IFNβ | MSYNLLGFLQ RSSNFQCQKL LWQLNGRLEY CLKDRMNFDI PEEIKQLQQF QKEDAALTIY EMLQNIFAIF RQDSSSTGWN ETIVENLLAN VYHQINHLKT VLEEKLEKED FTRGKLMSSL HLKRYYGRIL HYLKAKEYSH CAWTIVRVEI LRNFYFINRL TGYLRN |
| 158 | CID1276 | MSYNLLGFLQ RSSNRRCLML LAQLNGRLEY CLKDRMNFDI PEEIKQLQQF QKEDAALTIY EMLQNIFAIF RQDSSSTGWN ETIVENLLAN VYHQINHLKT VLEEKLEKED FTRGKLMSSL HLKRYYGRIL HYLKAKEYSH CAWTIVRVEI LRNFYFINRL TGYLRN |
| 159 | CID1277 | MSYNLLGFLQ RSSNFQCQKL LWQLNGRLEY CLKDRHDFGI PQEIKQLQQF QKEDAALTIY EMLQNIFAIF RQDSSSTGWN ETIVENLLAN VYHQINHLKT VLEEKLEKED FTRGKLMSSL HLKRYYGRIL HYLKAKEYSH CAWTIVRVEI LRNFYFINRL TGYLRN |
| 160 | CID1280 | MSYNLLGFLQ RSSNFQCQKL LWQLNGRLEY CLKDRMNFDI PEEIKQLQQF QKEDAALTIY EMLQNIFAIF RQDSSSTGWN ETIVDKLLTN VYHQINHLKT VLEEKLEKED FTRGKLMSSL HLKRYYGRIL HYLKAKEYSH CAWTIVRVEI LRNFYFINRL TGYLRN |
| 161 | CID1281 | MSYNLLGFLQ RSSNFQCQKL LWQLNGRLEY CLKDRMNFDI PEEIKQLQQF QKEDAALTIY EMLQNIFAIF RQDSSSTGWN ETIVENLLAE VYQQINDLEA VLEEKLEKED FTRGKLMSSL HLKRYYGRIL HYLKAKEYSH CAWTIVRVEI LRNFYFINRL TGYLRN |
| 162 | CID1283 | MSYNLLGFLQ RSSNFQCQKL LWQLNGRLEY CLKDRMNFDI PEEIKQLQQF QKEDAALTIY EMLQNIFAIF RQDSSSTGWN ETIVENLLAN VYHQINHLKT VLEEKLEKED FTRGKLMSIL HLRKYYGRIL HYLKAKEYSH CAWTIVRVEI LRNFYFINRL TGYLRN |

TABLE 12-continued sequences of hybrid IFN proteins

| Seq ID | Hybrid IFN name | Sequences (mutated residues underlined) |
|---|---|---|
| 163 | CID1285 | MSYNLLGFLQ RSSNFQCQKL LWQLNGRLEY CLKDRMNFDI PEEIKQLQQF<br>QKEDAALTIY EMLQNIFAIF RQDSSSTGWN ETIVENLLAN VYHQINHLKT<br>VLEEKLEKED FTRGKLMSSL HLKRYYGRIL HYLKEKKYSH CAWTIVRVEI<br>LRNFYFINRL TGYLRN |
| 164 | CID1286 | MSYNLLGFLQ RSSNFQCQKL LWQLNGRLEY CLKDRMNFDI PEEIKQLQQF<br>QKEDAALTIY EMLQNIFAIF RQDSSSTGWN ETIVENLLAN VYHQINHLKT<br>VLEEKLEKED FTRGKLMSSL HLKRYYGRIL HYLKAKEYSP CAWTIVRVEI<br>LRNFYFINRL TGYLRN |
| 165 | CID1287 | MSYNLLGFLQ RSSNFQCQKL LWQLNGRLEY CLKDRMNFDI PEEIKQLQQF<br>QKEDAALTIY EMLQNIFAIF RQDSSSTGWN ETIVENLLAN VYHQINHLKT<br>VLEEKLEKED FTRGKLMSSL HLKRYYGRIL HYLKAKEYSH CAWTIVRAEI<br>LRNFSLITRL TGYLRN |

All purified hybrid proteins were able to induce STAT1 phosphorylation, however, there were differences in the biological activity. Each hybrid protein was used at the $EC_{80}$ concentration in the following phospho-STAT1 assay (pSTAT1). U937 cells, a human monocytic cell line, were grown in RPMI 1640 containing 10% FBS (cRPMI). Antibody stocks were made at 4×, with a top concentration of 4-400 µM (final top concentration was 1-100 µM) and a 11 point, 10-fold dilution series was made in cRPMI; 25 µl was added/well in a u-bottom 96 well tissue culture plate. An equal volume of 4× hybrid or control IFNβ was added at the appropriate $EC_{80}$ concentration to the antibody stocks and incubated for 2 hours at 37° C. Control wells included media alone (no stimulation background pSTAT1 expression) or no addition of antibody (maximum pSTAT1 signal). U937 cells were harvested, centrifuged for 5 min at 1500 rpm at room temperature and then resuspended at a concentration of $2\times10^6$/ml in cRPMI warmed to 37° C.; 50 µl of cell suspension was added per well and plates placed at 37° C. for 15 minutes. Next 100 µl of pre-warmed cytofix buffer (BD Biosciences, catalog #554655) was added and plates were placed back at 37° C. for 15 minutes. Plates were removed and centrifuged as described above. Media was removed from the plates, cells resuspended and washed in 200 µl of PBS and centrifuged again. Media was removed again, cells were resuspended in 100 µl of permeabilization buffer IV (BD Biosciences) and incubated at room temperature for 15 minutes. At the end of the incubation, cells were centrifuged and washed as described above. After the PBS wash, cells were resuspended in 100 µl of PBS/5% FBS (FACS buffer); 5 µl of TruStain FcX/well (BioLegend) was added and plates were incubated for 10 min at 4° C. Ten microliters of Alexa Fluor 674 (AF647) conjugated anti-phospho STAT1 Ab (BD Biosciences) was added per well and incubated 20 min at 4° C. After incubation, 120 µl of FACS buffer was added per well and plates were centrifuged as described above. The wash was repeated with 220 µl of FACS buffer and cells were resuspended in 120 ul of FACS buffer; a Fortessa cytometer (BD Biosciences) was used to acquire the data and analysis was performed using FlowJo software (TreeStar). The geometric mean fluorescence intensity (Geo MFI) in the AF647 channel was calculated and prism software was used to calculate the $IC_{50}$. Data was normalized as the ratio of antibody concentration/IFN concentration and the percentage of the maximum signal was determined after subtracting the background.

U937 cells were stimulated with IFNα/IFNβ hybrid proteins for 15 minutes in the presence of CTI-AF1 after which the presence of phosphorylated STAT1 was assessed by intracellular flow cytometry. CTI-AF1 did not inhibit CID1280-dependent STAT1 phosphorylation and the potency for CID1281-induced STAT1 phosphorylation neutralization was greatly reduced. CTI-AF1 neutralized STAT1 phosphorylation of all other hybrid IFN proteins with equal potency relative to human IFNβ. See FIG. 19 and Table 13. These data combined indicate that the epitope residues recognized by CTI-AF1 are contained within the constructs CID1280 and CID1281, in which the IFNα sequence substitutions span amino acids 85-89 and 90-100, respectively (see Table 12).

TABLE 13

$IC_{50}$ and fold change of CTI-AF1 mediated neutralization of type I IFN-induced STAT1 phosphorylation

| IFN protein | $IC_{50}$ (nM) | Fold difference from IFNβ |
|---|---|---|
| Human IFNβ | 0.3 | |
| CID1276 | 0.2 | 0.7 |
| CID1277 | 0.3 | 0.9 |
| CID1280 | 47.7 | 161.8 |
| CID1281 | 3281.0 | 11137.1 |
| CID1283 | 0.4 | 1.2 |
| CID1285 | 0.4 | 1.4 |
| CID1286 | 0.4 | 1.4 |
| CID1287 | 0.3 | 1.0 |

Example 7. Crystal Structure of Anti-IFNβ Antibodies

The co-crystals of the complex between Cynomolgus monkey IFNβ and CTI-AF1 Fab were grown using the following solution as a precipitant: 19% PEG 3350, 250 mM sodium Citrate, 100 mM Bis-Tris propane pH 8.5. The crystals belong to space group P21 (unit cell parameters a=49.58 Å; b=91.76 Å; c=162.52 Å; b=94.86 deg) and contain two copies of complex per crystal asymmetric unit. The structure has been determined at 3.2 Å resolution using Molecular Replacement method and the refinement was performed using autoBUSTER.

CTI-AF1 Fab binds to IFNβ on the side formed by two α-helices, A and C, which define the binding epitope of CTI-AF1 (Table 13)

TABLE 13

Epitope analysis

| | cyno-IFNβ | | | | human IFNβ | | | |
|---|---|---|---|---|---|---|---|---|
| Structure elements | Amino Acids | Primary epitope | Secondary epitope | Optional epitope | Structural | Amino Acids | Primary epitope | Secondary epitope | Optional epitope |
| Helix A | Leu 5 | | | Leu 5 | Helix A | Leu 5 | | | Leu 5 |
| | Leu 6 | | | Leu 6 | | Leu 6 | | | Leu 6 |
| | Phe 8 | | Phe 8 | | | Phe 8 | | Phe 8 | |
| | Leu 9 | | Leu 9 | | | Leu 9 | | Leu 9 | |
| | Ser 12 | | Ser 12 | | | Ser 12 | | Ser 12 | |
| | Ser 13 | | | Ser 13 | | Ser 13 | | | Ser 13 |
| | Phe 15 | | | Phe 15 | | Phe 15 | | | Phe 15 |
| | Gln 16 | | Gln 16 | | | Gln 16 | | Gln 16 | |
| Helix C | Thr 82 | | | Thr 82 | Helix C | Thr 82 | | | Thr 82 |
| | Asn 86 | | Asn 86 | | | Asn 86 | | Asn 86 | |
| | Ala 89 | Ala 89 | | | | Ala 89 | Ala 89 | | |
| | Asn 90 | | Asn 90 | | | Asn 90 | | Asn 90 | |
| | Tyr 92 | Tyr 92 | | | | Tyr 92 | Tyr 92 | | |
| | His 93 | His 93 | | | | His 93 | His 93 | | |
| | Asp 96 | | Asp 96 | | | Asn 96 | | Asn 96 | |
| | His 97 | His 97 | | | | His 97 | His 97 | | |
| | Thr 100 | | Thr 100 | | | Thr 100 | | Thr 100 | |
| Helix B | Tyr 67 | | Tyr 67 | | Helix B | Phe 67 is not part of the epitope on human IFNβ | | | |

All amino acids that are within 3.8 Å from of CTI-AF1 were selected as "potential" epitope residues. "Primary" epitope residues are characterized as highly buried residues at the of CTI-AF1-IFNβ interface and zero-to-low sequence tolerance to any other amino acid substitutions at this position. "Secondary" epitope residues are characterized as residues with medium buried surface area at the interface and medium sequence tolerance to amino acid substitutions at these positions. "Optional" epitope residues are characterized as residues with low buried surface area at the interface and high sequence tolerance to amino acid substitutions at these positions.

The binding paratope is made up by five CDR-variable regions: CDR-H1, -H2, -H3 and CDR-L1, -L3 (Table 14). The total surface area buried under the binding interface is 1,920 Å$^2$. Analysis of CTI-AF1-IFNβ binding mode reveals that the neutralizing effect of CTI-AF1 is achieved through direct blockage on the IFNAR1 binding site.

TABLE 14

Paratope analysis

| CDRs | Amino Acids* | Primary Paratope | Secondary paratope |
|---|---|---|---|
| CDR-H1 | Trp 33H | Trp 33H | |
| CDR-H2 | Asp 54H | | Asp 54H |
| | Tyr 56H | Tyr 56H | |
| | Tyr 58H | Tyr 58H | |
| | Gln 61H | | Gln 61H |
| CDR-H3 | Tyr 97H | Tyr 97H | |
| | Gly 98H | | Gly 98H |
| | Leu 100H | | Leu 100H |
| CDR-L1 | Gln 27L | | Gln 27L |
| | Asp 28L | | Asp 28L |
| | Ile 29L | | Ile 29L |
| | Gly 30L | | Gly 30L |
| | Tyr 32L | Tyr 32L | |
| CDR-L3 | Ile 92L | Ile 92L | |
| | Ile 93L | | Ile 93L |
| | Leu 94L | Leu 94L | |

All amino acids that are within 3.8 Å from IFNβ were selected as "potential" binding paratope. "Primary" paratope residues are characterized as highly buried residues at the CTI-AF1-IFNβ interface and low sequence tolerance to any other amino acid substitutions at this position. "Secondary" paratope residues are characterized as residues with lower buried surface area at the interface and higher sequence tolerance to amino acid substitutions at these positions.

Table 15 summarizes the epitope-paratope interaction pairs. Table 16 summarizes epitope and paratope analysis based on BSA.

TABLE 15

Epitope-paratope interaction pairs

| Human IFNβ epitope residue | CTI-AF1 paratope residue(s) | Type of interaction |
|---|---|---|
| 5 Leu | 32L Tyr | H-bond |
| 6 Leu | 32L Tyr | H-bond |
| 8 Phe | 28L Asp, 29L Ile, 30L Gly, 32L Tyr | van der Waals |
| 9 Leu | 32L Tyr, 92L Ile | van der Waals |
| 12 Ser | 28L Asp | H-bond |
| | 92L Ile | van der Waals |
| 13 Ser | 92L Ile | van der Waals |
| 15 Phe | 27L Gln | van der Waals |
| 16 Gln | 27L Gln | H-bond |
| | 28L Asp, 93L Ile | van der Waals |
| 82 Thr | 61H Gln | van der Waals |
| 86 Asn | 58H Tyr, 94L Leu | van der Waals |
| 89 Ala | 58H Tyr, 94L Leu | van der Waals |
| 90 Asn | 93L Ile, | van der Waals |
| | 94L Leu | H-bond |
| 92 Tyr | 33H Trp, 56H Tyr | van der Waals |
| 93 His | 97H Tyr, | H-bond |
| | 100H Leu, | van der Waals |
| | 92L Ile | H-bond |
| 96 Asp | 97H Tyr, | van der Waals |
| | 33H Trp | H-bond |
| 97 His | 97H Tyr, 98H Gly, 100H Leu | van der Waals |
| 100 Thr | 97H Tyr | H-bond |

TABLE 16

Epitope and paratope analysis based on BSA

| Potential IFNβ epitope residues | BSA (Å²) |
|---|---|
| 5 Leu | 89.8 |
| 6 Leu | 3.5 |
| 8 Phe | 72.4 |
| 9 Leu | 51.8 |
| 12 Ser | 30.1 |
| 13 Ser | 18.9 |
| 16 Gln | 77.4 |
| 82 Thr | 40.2 |
| 86 Asn | 51.8 |
| 89 Ala | 52.0 |
| 90 Asn | 53.1 |
| 92 Tyr | 75.7 |
| 93 His | 119.4 |

| Potential paratope residues | Amino Acids* | BSA (Å²) |
|---|---|---|
| CDR-H1 | Trp 33H | 34.5 |
| CDR-H2 | Asp 54H | 18.7 |
|  | Tyr 56H | 67.6 |
|  | Tyr 58H | 69.9 |
|  | Gln 61H | 52.1 |
| CDR-H3 | Tyr 97H | 101.7 |
|  | Gly 98H | 31.7 |
|  | Leu 100H | 31.3 |
| CDR-L1 | Gln 27L | 54.4 |
|  | Asp 28L | 39.1 |
|  | Ile 29L | 7.8 |
|  | Gly 30L | 16.6 |
|  | Tyr 32L | 91.9 |
| CDR-L3 | Ile 92L | 80.3 |
|  | Ile 93L | 55.2 |
|  | Leu 94L | 79.7 |

Example 8. Type I Interferon Expression Profiles

In this example, we studied type I IFN expression profiles of 4 disease relevant cell lines in response to toll-like receptor ligand stimulation. Four types of cells were used: PBMCs, a dermal fibroblast cell line, a muscle cell line and a kidney cell line, which were stimulated with a TLR3, TLR4, TLR7/8 and TLR9 agonist in the presence and absence of anti-IFNβ antibody.

Gene expression levels of Type I IFN and Mx1 in different primary human cell types was measured using quantitative-PCR. Primary cells were cultured in the relevant media as follows: normal human dermal fibroblasts in FGM-2 bulletkit media, normal human mesangial in MsGM bulletkit media, and primary human skeletal muscle derived cells in Myotonic growth medium. Peripheral blood mononuclear cells (PBMC) were isolated by centrifugation over Ficoll-Paque Plus. Mononuclear cells were cultured in RPM11640 supplemented with 10% FBS and penicillin-streptomycin. To measure the type I IFN gene expression, cells were seeded then stimulated with the relevant TLR ligand for 1, 2.5, 5, 8 and 24 hours. After culture, cells were harvested, RNA was isolated and cDNA was synthesized. Expression of the following genes was assessed by Taqman PCR: IFNβ, Mx1, IFNα1, IFNα2, IFNα4, IFNα5, IFNα6, IFNα7, IFNα8, IFNα14, IFNα16, IFNα17, and B2m. Taqman real time PCR and fold change calculations were performed as described above (FIG. 9).

Table 17A shows that IFNβ is the predominant Type I IFN produced by various tissue resident primary human cell types upon Toll like receptor (TLR) ligand stimulation. Dermal fibroblasts, skeletal muscle cells, glomerular mesangial cells and PBMCs from normal human donors were stimulated with poly I:C (TLR3 ligand), LPS (TLR4 ligand), R848 (TLR7/8 ligand) and ODN2216 (TLR9 ligand) in a time and dose-dependent manner. Relative expression levels of IFNβ, Mx1, IFNα (1, 2, 4, 5, 6, 7, 8, 14, 16, and 17) were measured via quantitative-PCR using B2 M as the control. Relative expression of each gene is indicated as strong (+), weak (+/−) or no expression (−).

CTI-AF1 was shown to be a potent neutralizer of endogenously produced IFNβ from primary human cells stimulated with TLR ligands (poly I:C, LPS, R848 or ODN2216). Cells were stimulated with the various TLR ligands in the absence or presence of titrated amounts of CTI-AF1. Expression of Mx1 was measured 24 hours post stimulation, with the exception of PBMCs stimulated with LPS, which was measured at 6 hours. RNA isolation, cDNA synthesis and quantitative PCR were performed as described above (FIG. 9). While the amount of IFNβ induced by any cell type upon TLR stimulation was unknown, a dose-dependent inhibition of Mx1 expression was seen in the presence of CTI-AF1.

Table 17B shows that CTI-AF1 is a potent inhibitor of endogenous IFNβ secreted by primary human cells after poly I:C and LPS stimulation. Cells were stimulated with the indicated TLR ligand and quantitative-PCR was performed to determine the level of Mx1 expression using B2 M as the control. Dose-dependent inhibition of Mx1 gene expression by CTI-AF1 is indicated by "+" while the absence of CTI-AF1 dependent Mx1 expression inhibition is indicated by "−". Conditions where Type I IFN expression was insufficient to drive any meaningful increase in Mx1 expression that could potentially be neutralized by CTI-AF1 is indicated as NA.

TABLE 17A

| Gene transcript | Dermal Fibroblasts | | | | Skeletal Muscle Cells | | | |
| | In vitro stimulation | | | | | | | |
| | PolyI:C | LPS | R848 | ODN2216 | PolyI:C | LPS | R848 | ODN2216 |
|---|---|---|---|---|---|---|---|---|
| IFNβ | + | + | − | − | + | + | − | − |
| Mx1 | + | + | − | − | + | + | − | − |
| IFNα1 | − | − | +/− | +/− | − | +/− | − | − |
| IFNα2 | − | − | − | − | − | − | − | − |
| IFNα4 | − | − | − | − | − | − | − | − |
| IFNα5 | +/− | − | − | − | − | − | − | − |
| IFNα6 | − | − | − | − | − | − | − | − |
| IFNα7 | − | − | − | − | − | − | − | − |
| IFNα8 | − | − | − | − | − | − | − | − |
| IFNα14 | − | − | − | − | − | − | − | − |
| IFNα16 | − | − | − | − | − | − | − | − |
| IFNα17 | − | − | − | − | − | − | − | − |

TABLE 17A-continued

| Gene transcript | Glomerular Mesangial Cells In vitro stimulation | | | | PBMCs | | | |
|---|---|---|---|---|---|---|---|---|
| | PolyI:C | LPS | R848 | ODN2216 | PolyI:C | LPS | R848 | ODN2216 |
| IFNβ | + | + | − | − | + | + | + | + |
| Mx1 | + | + | − | − | + | + | + | + |
| IFNα1 | − | +/− | +/− | − | +/− | +/− | + | + |
| IFNα2 | − | − | − | − | +/− | − | + | + |
| IFNα4 | − | − | − | − | +/− | − | + | + |
| IFNα5 | − | − | − | − | − | − | + | + |
| IFNα6 | − | − | − | − | +/− | − | + | + |
| IFNα7 | − | − | − | − | +/− | − | + | + |
| IFNα8 | − | − | − | − | +/− | +/− | + | + |
| IFNα14 | − | − | − | − | +/− | +/− | + | + |
| IFNα16 | − | − | − | − | +/− | − | + | + |
| IFNα17 | − | − | − | − | − | − | + | + |

+ = strong expression;
+/− = relatively weak expression;
− = not detected

TABLE 17B

| Gene transcript | Dermal Fibroblasts | | | | Skeletal Muscle Cells | | | | Glomerular Mesangial Cells | | | | PBMCs | | | |
|---|---|---|---|---|---|---|---|---|---|---|---|---|---|---|---|---|
| | PolyI:C | LPS | R848 | ODN2216 | PolyI:C | LPS | R848 | ODN2216 | PolyI:C | LPS | R848 | ODN2216 | PolyI:C | LPS | R848 | ODN2216 |
| Mx1 | + | + | NA | NA | + | + | NA | NA | + | + | NA | NA | + | + | − | − |

+ = dose-dependent Inhibition of Mx1 gene expression by CTI-AF1;
− = no dose-dependent Inhibition of Mx1 gene expression;
NA = not applicable, Insufficient type I IFN expression to drive Mx1 expression

TABLE 18

Sequences of interferon β proteins

| SEQ ID | Name | Sequence |
|---|---|---|
| 40 | Human IFNβ precursor | MTNKCLLQIA LLLCFSTTAL SMSYNLLGFL QRSSNFQCQK LLWQLNGRLE YCLKDRMNFD IPEEIKQLQQ FQKEDAALTI YEMLQNIFAI FRQDSSSTGW NETIVENLLA NVYHQINHLK TVLEEKLEKE DFTRGKLMSS LHLKRYYGRI LHYLKAKEYS HCAWTIVRVE ILRNFYFINR LTGYLRN |
| 41 | Mature human IFNβ | MSYNLLGFLQ RSSNFQCQKL LWQLNGRLEY CLKDRMNFDI PEEIKQLQQF QKEDAALTIY EMLQNIFAIF RQDSSSTGWN ETIVENLLAN VYHQINHLKT VLEEKLEKED FTRGKLMSSL HLKRYYGRIL HYLKAKEYSH CAWTIVRVEI LRNFYFINRL TGYLRN |
| 42 | Mature mouse IFNβ | INYKQLQLQE RTNIRKCQEL LEQLNGKINL TYRADFKIPM EMTEKMQKSY TAFAIQEMLQ NVFLVFRNNF SSTGWNETIV VRLLDELHQQ TVFLKTVLEE KQEERLTWEM SSTALHLKSY YWRVQRYLKL MKYNSYAWMV VRAEIFRNFL IIRRLTRNFQ N |
| 43 | Mature rat IFNβ | IDYKQLQFRQ STSIRTCQKL LRQLNGRLNL SYRTDFKIPM EVMHPSQMEK SYTAFAIQVM LQNVFLVFRS NFSSTGWNET IVESLLDELH QQTELLEIIL KEKQEERLTW VTSTTTLGLK SYYWRVQRYL KDKKYNSYAW MVVRAEVFRN FSIILRLNRN FQN |
| 44 | Mature Cynomolgus monkey IFNβ | MSYNLLGFLQ RSSSFQCQKL LWQLNGRLEY CLKDRMNFDI PEEIKQPQQF QKEDAALTIY EMLQNIYAIF RQDLSSTGWN ETIVENLLAN VYHQIDHLKT ILEEKLEKED FTRGKFVSSL HLKRYYGRIL HYLKAKEYSH CAWTIVRVEI LRNFFFINKL TGYLRN |
| 45 | Mature rabbit IFNβ | MSYNSLQIQL WHGSLTCAKL LLQLNGTTED CLNERINFKV PKEIKEPQQL QKEDTTLVIF EMLNNIFDIF RKNFSSTGWN ETLVENLLGE THLQIHHLKS KINKKVTLES IRMNLRLKSY YWRIMDYLET KQYSNCAWKI VQLEIFRNFS FIIMLIDYL |

The various features and embodiments of the present invention, referred to in individual sections above apply, as appropriate, to other sections, mutatis mutandis. Consequently features specified in one section may be combined with features specified in other sections, as appropriate. All references cited herein, including patents, patent applications, papers, text books, and cited sequence Accession numbers, and the references cited therein are hereby incorporated by reference in their entirety. In the event that one or more of the incorporated literature and similar materials differs from or contradicts this application, including but not limited to defined terms, term usage, described techniques, or the like, this application controls.

What is claimed is:

1. An isolated nucleic acid molecule comprising a nucleotide sequence encoding the antibody, or antigen-binding fragment thereof, that specifically binds human IFNβ, wherein the antibody or antigen-binding fragment comprises (a) the CDR-H1, CDR-H2, and CDR-H3 sequences of SEQ ID NO: 28, and (b)
   i) the CDR-L1, CDR-L2, and CDR-L3 sequences of SEQ ID NO: 2;
   ii) the CDR-L1, CDR-L2, and CDR-L3 sequences of SEQ ID NO: 3;
   iii) the CDR-L1, CDR-L2, and CDR-L3 sequences of SEQ ID NO: 4;
   iv) the CDR-L1, CDR-L2, and CDR-L3 sequences of SEQ ID NO: 5;
   v) the CDR-L1, CDR-L2, and CDR-L3 sequences of SEQ ID NO: 6;
   vi) the CDR-L1, CDR-L2, and CDR-L3 sequences of SEQ ID NO: 7;
   vii) the CDR-L1, CDR-L2, and CDR-L3 sequences of SEQ ID NO: 8;
   viii) the CDR-L1, CDR-L2, and CDR-L3 sequences of SEQ ID NO: 9;
   ix) the CDR-L1, CDR-L2, and CDR-L3 sequences of SEQ ID NO: 10;
   x) the CDR-L1, CDR-L2, and CDR-L3 sequences of SEQ ID NO: 11;
   xi) the CDR-L1, CDR-L2, and CDR-L3 sequences of SEQ ID NO: 12;
   xii) the CDR-L1, CDR-L2, and CDR-L3 sequences of SEQ ID NO: 13;
   xiii) the CDR-L1, CDR-L2, and CDR-L3 sequences of SEQ ID NO: 14;
   xiv) the CDR-L1, CDR-L2, and CDR-L3 sequences of SEQ ID NO: 15;
   xv) the CDR-L1, CDR-L2, and CDR-L3 sequences of SEQ ID NO: 16;
   xvi) the CDR-L1, CDR-L2, and CDR-L3 sequences of SEQ ID NO: 17;
   xvii) the CDR-L1, CDR-L2, and CDR-L3 sequences of SEQ ID NO: 18;
   xviii) the CDR-L1, CDR-L2, and CDR-L3 sequences of SEQ ID NO: 19;
   xix) the CDR-L1, CDR-L2, and CDR-L3 sequences of SEQ ID NO: 20;
   xx) the CDR-L1, CDR-L2, and CDR-L3 sequences of SEQ ID NO: 21;
   xxi) the CDR-L1, CDR-L2, and CDR-L3 sequences of SEQ ID NO: 22;
   xxii) the CDR-L1, CDR-L2, and CDR-L3 sequences of SEQ ID NO: 23;
   xxiii) the CDR-L1, CDR-L2, and CDR-L3 sequences of SEQ ID NO: 24;
   xxiv) the CDR-L1, CDR-L2, and CDR-L3 sequences of SEQ ID NO: 25;
   xxv) the CDR-L1, CDR-L2, and CDR-L3 sequences of SEQ ID NO: 26;
   xxvi) the CDR-L1, CDR-L2, and CDR-L3 sequences of SEQ ID NO: 27; or
   xxvii) the CDR-L1, CDR-L2, and CDR-L3 sequences of SEQ ID NO: 1.

2. The isolated nucleic acid molecule of claim 1, wherein the antibody, or antigen-binding fragment thereof, comprises: (i) a VH that comprises:
   (a) a VH CDR-H1 comprising the amino acid sequence of SEQ ID NO: 37,
   (b) a VH CDR-H2 comprising the amino acid sequence of SEQ ID NO: 38; and
   (c) a VH CDR-H3 comprising the amino acid sequence of SEQ ID NO: 39; and
   (ii) a VL that comprises:
   (a) a VL CDR-L1 comprising the amino acid sequence of SEQ ID NO: 34,
   (b) a VL CDR-L2 comprising the amino acid sequence of SEQ ID NO: 35; and
   (c) a VL CDR-L3 comprising the amino acid sequence of SEQ ID NO: 36.

3. An isolated nucleic acid molecule comprising: (i) the nucleotide sequence of SEQ ID NO:166; (ii) the nucleotide sequence of SEQ ID NO:167; (iii) the nucleotide sequence of the insert of the plasmid deposited at the ATCC and having Accession Number PTA-122727; or (iv) the nucleotide sequence of the insert of the plasmid deposited at the ATCC and having Accession Number PTA-122726.

4. A vector comprising the nucleic acid molecule of claim 1.

5. A host cell comprising the nucleic acid molecule of claim 1.

6. The isolated nucleic acid molecule of claim 1, wherein the antibody or antigen-binding fragment comprises one or more of:
   (i) a heavy chain variable region (VH) that comprises the amino acid sequence of SEQ ID NO: 28;
   (ii) a heavy chain constant region (CH) that comprises the amino acid sequence of SEQ ID NO: 29;
   (iii) a light chain variable region (VL) that comprises the amino acid sequence of SEQ ID NO: 1;
   (iv) a light chain constant region (CL) that comprises the amino acid sequence of SEQ ID NO: 30;
   (v) a VH that comprises the amino acid sequence of SEQ ID NO: 28, and a VL that comprises the amino acid sequence of any one of SEQ ID NOs: 2-27;

(vi) a heavy chain that comprises the amino acid sequence of SEQ ID NO: 33; and
(vii) a light chain that comprises the amino acid sequence of SEQ ID NO: 32.

7. The isolated nucleic acid molecule of claim 1, wherein the antibody or antigen-binding fragment comprises a VH that comprises the amino acid sequence of SEQ ID NO: 28 and a VL that comprises the amino acid sequence of SEQ ID NO: 1.

8. The isolated nucleic acid molecule of claim 1, wherein the antibody or antigen-binding fragment comprises a heavy chain that comprises the amino acid sequence of SEQ ID NO: 33 and a light chain that comprises the amino acid sequence of SEQ ID NO: 32.

9. The isolated nucleic acid molecule of claim 1, wherein the nucleotide sequence encoding the VH comprises the nucleic acid sequence of SEQ ID NO:166; and wherein the nucleotide sequence encoding the VL comprises the nucleic acid sequence of SEQ ID NO:167.

10. A method of producing an antibody, or antigen-binding fragment thereof, comprising culturing the host cell of claim 5, under conditions wherein the antibody, or antigen-binding fragment thereof, is produced by the host cell.

11. A first isolated nucleic acid molecule comprising a nucleotide sequence encoding an immunoglobulin heavy chain, or antigen-binding fragment thereof, wherein the heavy chain or antigen-binding fragment comprises the CDR-H1, CDR-H2, and CDR-H3 sequences of SEQ ID NO: 28, and
   a second isolated nucleic acid molecule comprising a nucleotide sequence encoding an immunoglobulin light chain, or antigen-binding fragment thereof, wherein the light chain or antigen-binding fragment comprises:
   i) the CDR-L1, CDR-L2, and CDR-L3 sequences of SEQ ID NO: 2;
   ii) the CDR-L1, CDR-L2, and CDR-L3 sequences of SEQ ID NO: 3;
   iii) the CDR-L1, CDR-L2, and CDR-L3 sequences of SEQ ID NO: 4;
   iv) the CDR-L1, CDR-L2, and CDR-L3 sequences of SEQ ID NO: 5;
   v) the CDR-L1, CDR-L2, and CDR-L3 sequences of SEQ ID NO: 6;
   vi) the CDR-L1, CDR-L2, and CDR-L3 sequences of SEQ ID NO: 7;
   vii) the CDR-L1, CDR-L2, and CDR-L3 sequences of SEQ ID NO: 8;
   viii) the CDR-L1, CDR-L2, and CDR-L3 sequences of SEQ ID NO: 9;
   ix) the CDR-L1, CDR-L2, and CDR-L3 sequences of SEQ ID NO: 10;
   x) the CDR-L1, CDR-L2, and CDR-L3 sequences of SEQ ID NO: 11;
   xi) the CDR-L1, CDR-L2, and CDR-L3 sequences of SEQ ID NO: 12;
   xii) the CDR-L1, CDR-L2, and CDR-L3 sequences of SEQ ID NO: 13;
   xiii) the CDR-L1, CDR-L2, and CDR-L3 sequences of SEQ ID NO: 14;
   xiv) the CDR-L1, CDR-L2, and CDR-L3 sequences of SEQ ID NO: 15;
   xv) the CDR-L1, CDR-L2, and CDR-L3 sequences of SEQ ID NO: 16;
   xvi) the CDR-L1, CDR-L2, and CDR-L3 sequences of SEQ ID NO: 17;
   xvii) the CDR-L1, CDR-L2, and CDR-L3 sequences of SEQ ID NO: 18;
   xviii) the CDR-L1, CDR-L2, and CDR-L3 sequences of SEQ ID NO: 19;
   xix) the CDR-L1, CDR-L2, and CDR-L3 sequences of SEQ ID NO: 20;
   xx) the CDR-L1, CDR-L2, and CDR-L3 sequences of SEQ ID NO: 21;
   xxi) the CDR-L1, CDR-L2, and CDR-L3 sequences of SEQ ID NO: 22;
   xxii) the CDR-L1, CDR-L2, and CDR-L3 sequences of SEQ ID NO: 23;
   xxiii) the CDR-L1, CDR-L2, and CDR-L3 sequences of SEQ ID NO: 24;
   xxiv) the CDR-L1, CDR-L2, and CDR-L3 sequences of SEQ ID NO: 25;
   xxv) the CDR-L1, CDR-L2, and CDR-L3 sequences of SEQ ID NO: 26;
   xxvi) the CDR-L1, CDR-L2, and CDR-L3 sequences of SEQ ID NO: 27; or
   xxvii) the CDR-L1, CDR-L2, and CDR-L3 sequences of SEQ ID NO: 1.

12. The first and second isolated nucleic acid molecules of claim 11, wherein
   (i) the heavy chain comprises a heavy chain variable region (VH) that comprises the amino acid sequence of SEQ ID NO: 28;
   (ii) the heavy chain comprises a heavy chain constant region (CH) that comprises the amino acid sequence of SEQ ID NO: 29;
   (iii) the light chain comprises a light chain variable region (VL) that comprises the amino acid sequence of SEQ ID NO: 1;
   (iv) the light chain comprises a light chain constant region (CL) that comprises the amino acid sequence of SEQ ID NO: 30;
   (v) the heavy chain or antigen-binding fragment comprises a heavy chain variable region (VH) that comprises the amino acid sequence of SEQ ID NO: 28, and wherein the light chain or antigen-binding fragment comprises a light chain variable region (VL) that comprises the amino acid sequence of any one of SEQ ID NOs: 2-27;
   (vi) the heavy chain that comprises the amino acid sequence of SEQ ID NO: 33;
   (vii) the light chain that comprises the amino acid sequence of SEQ ID NO: 32; or
   (viii) a combination of any of (i)-(vii).

13. The first and second isolated nucleic acid molecules of claim 11, wherein the heavy chain or antigen-binding fragment comprises:
   (a) a CDR-H1 comprising the amino acid sequence of SEQ ID NO: 37;
   (b) a CDR-H2 comprising the amino acid sequence of SEQ ID NO: 38;
   (c) a CDR-H3 comprising the amino acid sequence of SEQ ID NO: 39; and
wherein the light chain or antigen-binding fragment comprises:
   (d) a CDR-L1 comprising the amino acid sequence of SEQ ID NO: 34;
   (e) a CDR-L2 comprising the amino acid sequence of SEQ ID NO: 35; and
   (f) a CDR-L3 comprising the amino acid sequence of SEQ ID NO: 36.

14. The first and second isolated nucleic acid molecules of claim 11, wherein the nucleotide sequence encoding the VH comprises the nucleic acid sequence of SEQ ID NO:166; and wherein the nucleotide sequence encoding the VL comprises the nucleic acid sequence of SEQ ID NO:167.

15. The first and second isolated nucleic acid molecules of claim 11, wherein the heavy chain comprises a heavy chain variable region (VH) that comprises the amino acid sequence of SEQ ID NO: 28 and the light chain comprises a light chain variable region (VL) that comprises the amino acid sequence of SEQ ID NO: 1.

16. The first and second isolated nucleic acid molecules of claim 11, wherein the heavy chain comprises the amino acid sequence of SEQ ID NO: 33 and the light chain comprises the amino acid sequence of SEQ ID NO: 32.

17. A first vector and a second vector comprising the first and second nucleic acid molecules, respectively, of claim 11.

18. A host cell comprising the first and second nucleic acid molecules of claim 11.

\* \* \* \* \*

SEQUENCE LISTING

```
<160> NUMBER OF SEQ ID NOS: 167

<210> SEQ ID NO 1
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Tyr
            20                  25                  30

Leu Asn Trp Tyr Gln Gln Lys Pro Gly Lys Ala Phe Lys Leu Leu Ile
        35                  40                  45

Tyr Ser Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ile Ile Leu Pro Ile
                85                  90                  95

Thr Phe Gly Gly Gly Thr Lys Val Glu Ile Lys
            100                 105

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Tyr
            20                  25                  30

Leu Asn Trp Tyr Gln Gln Lys Pro Gly Lys Ala Phe Lys Leu Leu Ile
        35                  40                  45

Tyr Ser Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ile Val Leu Pro Ile
                85                  90                  95

Thr Phe Gly Gly Gly Thr Lys Val Glu Ile Lys
            100                 105

<210> SEQ ID NO 3
<211> LENGTH: 107
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Phe Lys Leu Leu Ile
        35                  40                  45

Phe Ser Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ile Val Leu Pro Ile
                85                  90                  95

Thr Phe Gly Gly Gly Thr Lys Val Glu Ile Lys
            100                 105

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Ser Tyr
            20                  25                  30

Leu Asn Trp Tyr Gln Gln Lys Pro Gly Lys Ala Phe Lys Leu Leu Ile
        35                  40                  45

Tyr Ser Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ile Val Leu Pro Ile
                85                  90                  95

Thr Phe Gly Gly Gly Thr Lys Val Glu Ile Lys
            100                 105

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Phe Lys Leu Leu Ile
        35                  40                  45

```
Tyr Thr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Ile Val Leu Pro Ile
                 85                  90                  95

Thr Phe Gly Gly Gly Thr Lys Val Glu Ile Lys
                100                 105

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Ser Leu Ser Ala Ser Val Gly
 1               5                  10                  15

Asp Arg Val Thr Ile Thr Cys Arg Thr Ser Gln Asp Ile Asp Asn Phe
            20                  25                  30

Leu Gln Trp Tyr Gln Gln Lys Pro Gly Lys Ala Phe Lys Leu Leu Ile
        35                  40                  45

Tyr Ser Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Ile Val Leu Pro Ile
                 85                  90                  95

Thr Phe Gly Gly Gly Thr Lys Val Glu Ile Lys
                100                 105

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Met Thr Gln Ser Pro Ser Ser Leu Ser Ala Ser Val Gly
 1               5                  10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Phe Lys Leu Leu Ile
        35                  40                  45

Tyr Ser Thr Ser Lys Leu His Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Ile Val Leu Pro Ile
                 85                  90                  95

Thr Phe Gly Gly Gly Thr Lys Val Glu Ile Lys
                100                 105

<210> SEQ ID NO 8
```

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Tyr
            20                  25                  30

Leu Asn Trp Tyr Gln Gln Lys Pro Gly Lys Ala Phe Lys Leu Leu Ile
        35                  40                  45

Tyr Ser Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Thr Ile Leu Pro Leu
                85                  90                  95

Thr Phe Gly Gly Gly Thr Lys Val Glu Ile Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Phe Lys Leu Leu Ile
        35                  40                  45

Phe Ser Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Thr Ile Leu Pro Leu
                85                  90                  95

Thr Phe Gly Gly Gly Thr Lys Val Glu Ile Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Ser Tyr
            20                  25                  30
```

```
Leu Asn Trp Tyr Gln Gln Lys Pro Gly Lys Ala Phe Lys Leu Leu Ile
        35                  40                  45

Tyr Ser Thr Ser Arg Leu His Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Thr Ile Leu Pro Leu
                 85                  90                  95

Thr Phe Gly Gly Gly Thr Lys Val Glu Ile Lys
            100                 105
```

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Asp Ile Gln Met Thr Gln Ser Pro Ser Ser Leu Ser Ala Ser Val Gly
 1               5                  10                  15

Asp Arg Val Thr Ile Thr Cys Arg Thr Ser Gln Asp Ile Ser Asn Tyr
             20                  25                  30

Leu Asn Trp Tyr Gln Gln Lys Pro Gly Lys Ala Phe Lys Leu Leu Ile
        35                  40                  45

Tyr Thr Thr Ser Arg Leu Arg Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Thr Ile Leu Pro Leu
                 85                  90                  95

Thr Phe Gly Gly Gly Thr Lys Val Glu Ile Lys
            100                 105
```

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Asp Ile Gln Met Thr Gln Ser Pro Ser Ser Leu Ser Ala Ser Val Gly
 1               5                  10                  15

Asp Arg Val Thr Ile Thr Cys Arg Thr Ser Gln Asp Ile Asp Asn Phe
             20                  25                  30

Leu Gln Trp Tyr Gln Gln Lys Pro Gly Lys Ala Phe Lys Leu Leu Ile
        35                  40                  45

Tyr Ser Thr Ser Arg Leu His Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Thr Ile Leu Pro Leu
                 85                  90                  95

Thr Phe Gly Gly Gly Thr Lys Val Glu Ile Lys
            100                 105
```

```
<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Phe Lys Leu Leu Ile
        35                  40                  45

Tyr Ser Thr Ser Lys Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Thr Ile Leu Pro Leu
                85                  90                  95

Thr Phe Gly Gly Gly Thr Lys Val Glu Ile Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Phe Lys Leu Leu Ile
        35                  40                  45

Phe Ser Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ile Ile Leu Pro Ile
                85                  90                  95

Thr Phe Gly Gly Gly Thr Lys Val Glu Ile Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Ser Tyr
```

```
            20                  25                  30

Leu Asn Trp Tyr Gln Gln Lys Pro Gly Lys Ala Phe Lys Leu Leu Ile
            35                  40                  45

Tyr Ser Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ile Ile Leu Pro Ile
                85                  90                  95

Thr Phe Gly Gly Gly Thr Lys Val Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Phe Lys Leu Leu Ile
            35                  40                  45

Tyr Thr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ile Ile Leu Pro Ile
                85                  90                  95

Thr Phe Gly Gly Gly Thr Lys Val Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Asp Asn Phe
            20                  25                  30

Leu Gln Trp Tyr Gln Gln Lys Pro Gly Lys Ala Phe Lys Leu Leu Ile
            35                  40                  45

Tyr Ser Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ile Ile Leu Pro Ile
                85                  90                  95

Thr Phe Gly Gly Gly Thr Lys Val Glu Ile Lys
```

```
<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Asn Tyr
            20                  25                  30

Leu Asn Trp Tyr Gln Gln Lys Pro Gly Lys Ala Phe Lys Leu Leu Ile
        35                  40                  45

Tyr Ser Thr Ser Lys Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ile Ile Leu Pro Ile
                85                  90                  95

Thr Phe Gly Gly Gly Thr Lys Val Glu Ile Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Tyr
            20                  25                  30

Leu Asn Trp Tyr Gln Gln Lys Pro Gly Lys Ala Phe Lys Leu Leu Ile
        35                  40                  45

Phe Ser Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ile Val Leu Pro Ile
                85                  90                  95

Thr Phe Gly Gly Gly Thr Lys Val Glu Ile Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Ser Leu Ser Ala Ser Val Gly
1               5                   10                  15
```

```
Asp Arg Val Thr Ile Thr Cys Arg Thr Ser Gln Asp Ile Ser Ser Tyr
            20                  25                  30

Leu Asn Trp Tyr Gln Gln Lys Pro Gly Lys Ala Phe Lys Leu Leu Ile
        35                  40                  45

Tyr Thr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
65                   70                  75                  80

Glu Asp Phe Ala Thr Tyr Tyr Cys Gln Gln Gly Ile Val Leu Pro Ile
                 85                  90                  95

Thr Phe Gly Gly Gly Thr Lys Val Glu Ile Lys
            100                 105

<210> SEQ ID NO 21
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Asp Asn Phe
            20                  25                  30

Leu Gln Trp Tyr Gln Gln Lys Pro Gly Lys Ala Phe Lys Leu Leu Ile
        35                  40                  45

Phe Ser Thr Ser Lys Leu His Ser Gly Val Pro Ser Arg Phe Ser Gly
 50                  55                  60

Ser Gly Ser Gly Thr Asp Phe Thr Leu Thr Ile Ser Ser Leu Gln Pro
65                   70                  75                  80

Glu Asp Phe Ala Thr Tyr Tyr Cys Gln Gln Gly Ile Val Leu Pro Ile
                 85                  90                  95

Thr Phe Gly Gly Gly Thr Lys Val Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Tyr
            20                  25                  30

Leu Asn Trp Tyr Gln Gln Lys Pro Gly Lys Ala Phe Lys Leu Leu Ile
        35                  40                  45

Phe Ser Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
65                   70                  75                  80

Glu Asp Phe Ala Thr Tyr Tyr Cys Gln Gln Ser Thr Ile Leu Pro Leu
                 85                  90                  95
```

Thr Phe Gly Gly Gly Thr Lys Val Glu Ile Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Ser Tyr
            20                  25                  30

Leu Asn Trp Tyr Gln Gln Lys Pro Gly Lys Ala Phe Lys Leu Leu Ile
        35                  40                  45

Tyr Thr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Thr Ile Leu Pro Leu
                85                  90                  95

Thr Phe Gly Gly Gly Thr Lys Val Glu Ile Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Asp Asn Phe
            20                  25                  30

Leu Gln Trp Tyr Gln Gln Lys Pro Gly Lys Ala Phe Lys Leu Leu Ile
        35                  40                  45

Phe Ser Thr Ser Lys Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Thr Ile Leu Pro Leu
                85                  90                  95

Thr Phe Gly Gly Gly Thr Lys Val Glu Ile Lys
            100                 105

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Tyr
            20                  25                  30

Leu Asn Trp Tyr Gln Gln Lys Pro Gly Lys Ala Phe Lys Leu Leu Ile
        35                  40                  45

Phe Ser Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ile Ile Leu Pro Ile
                85                  90                  95

Thr Phe Gly Gly Gly Thr Lys Val Glu Ile Lys
            100                 105
```

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Ser Ser Tyr
            20                  25                  30

Leu Asn Trp Tyr Gln Gln Lys Pro Gly Lys Ala Phe Lys Leu Leu Ile
        35                  40                  45

Tyr Thr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ile Ile Leu Pro Ile
                85                  90                  95

Thr Phe Gly Gly Gly Thr Lys Val Glu Ile Lys
            100                 105
```

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Arg Ser Gln Asp Ile Asp Asn Phe
            20                  25                  30

Leu Gln Trp Tyr Gln Gln Lys Pro Gly Lys Ala Phe Lys Leu Leu Ile
        35                  40                  45

Phe Ser Thr Ser Lys Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Gly Ile Ile Leu Pro Ile
                85                  90                  95

Thr Phe Gly Gly Gly Thr Lys Val Glu Ile Lys
            100                 105
```

<210> SEQ ID NO 28
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Arg Tyr
            20                  25                  30

Trp Met His Trp Val Arg Gln Ala Pro Gly Gln Gly Leu Glu Trp Met
        35                  40                  45

Gly His Ile Asp Pro Ser Asp Ser Tyr Thr Tyr Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Tyr Gly Asn Leu Leu Phe Glu Tyr Trp Gly Gln Gly
            100                 105                 110

Thr Leu Val Thr Val Ser Ser
        115
```

<210> SEQ ID NO 29
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (330)..(330)
<223> OTHER INFORMATION: May or may not be present

<400> SEQUENCE: 29

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125
```

```
Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 31

<400> SEQUENCE: 31

000
```

```
<210> SEQ ID NO 32
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Gly Asn Tyr
            20                  25                  30

Leu Asn Trp Tyr Gln Gln Lys Pro Gly Lys Ala Phe Lys Leu Leu Ile
        35                  40                  45

Tyr Ser Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ile Ile Leu Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 33
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (449)..(449)
<223> OTHER INFORMATION: May or may not be present

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Arg Tyr
            20                  25                  30

Trp Met His Trp Val Arg Gln Ala Pro Gly Gln Gly Leu Glu Trp Met
        35                  40                  45

Gly His Ile Asp Pro Ser Asp Ser Tyr Thr Tyr Tyr Asn Gln Lys Phe
50                  55                  60
```

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Tyr Gly Asn Leu Leu Phe Glu Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 34
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 34

Arg Thr Ser Gln Asp Ile Gly Asn Tyr Leu Asn
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Thr Ser Arg Leu His Ser
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gln Gly Ile Ile Leu Pro Ile Thr
1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Tyr Thr Phe Ser Arg Tyr Trp Met His
1               5                   10

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

His Ile Asp Pro Ser Asp Ser Tyr Thr Tyr Tyr Asn Gln Lys Phe Lys
1               5                   10                  15

Gly

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39
```

Trp Asp Tyr Gly Asn Leu Leu Phe Glu Tyr
1               5                   10

<210> SEQ ID NO 40
<211> LENGTH: 187
<212> TYPE: PRT
<213> ORGANISM: Homo sapiens

<400> SEQUENCE: 40

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185

<210> SEQ ID NO 41
<211> LENGTH: 166
<212> TYPE: PRT
<213> ORGANISM: Homo sapiens

<400> SEQUENCE: 41

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 42
<211> LENGTH: 161
<212> TYPE: PRT
<213> ORGANISM: Mus sp.

<400> SEQUENCE: 42

Ile Asn Tyr Lys Gln Leu Gln Leu Gln Glu Arg Thr Asn Ile Arg Lys
1               5                   10                  15

Cys Gln Glu Leu Leu Glu Gln Leu Asn Gly Lys Ile Asn Leu Thr Tyr
                20                  25                  30

Arg Ala Asp Phe Lys Ile Pro Met Glu Met Thr Glu Lys Met Gln Lys
            35                  40                  45

Ser Tyr Thr Ala Phe Ala Ile Gln Glu Met Leu Gln Asn Val Phe Leu
    50                  55                  60

Val Phe Arg Asn Asn Phe Ser Ser Thr Gly Trp Asn Glu Thr Ile Val
65                  70                  75                  80

Val Arg Leu Leu Asp Glu Leu His Gln Gln Thr Val Phe Leu Lys Thr
                85                  90                  95

Val Leu Glu Glu Lys Gln Glu Glu Arg Leu Thr Trp Glu Met Ser Ser
            100                 105                 110

Thr Ala Leu His Leu Lys Ser Tyr Tyr Trp Arg Val Gln Arg Tyr Leu
        115                 120                 125

Lys Leu Met Lys Tyr Asn Ser Tyr Ala Trp Met Val Val Arg Ala Glu
    130                 135                 140

Ile Phe Arg Asn Phe Leu Ile Ile Arg Arg Leu Thr Arg Asn Phe Gln
145                 150                 155                 160

Asn

<210> SEQ ID NO 43
<211> LENGTH: 163
<212> TYPE: PRT
<213> ORGANISM: Rattus sp.

<400> SEQUENCE: 43

Ile Asp Tyr Lys Gln Leu Gln Phe Arg Gln Ser Thr Ser Ile Arg Thr
1               5                   10                  15

Cys Gln Lys Leu Leu Arg Gln Leu Asn Gly Arg Leu Asn Leu Ser Tyr
                20                  25                  30

Arg Thr Asp Phe Lys Ile Pro Met Glu Val Met His Pro Ser Gln Met
            35                  40                  45

Glu Lys Ser Tyr Thr Ala Phe Ala Ile Gln Val Met Leu Gln Asn Val
    50                  55                  60

Phe Leu Val Phe Arg Ser Asn Phe Ser Ser Thr Gly Trp Asn Glu Thr
65                  70                  75                  80

Ile Val Glu Ser Leu Leu Asp Glu Leu His Gln Gln Thr Glu Leu Leu
                85                  90                  95

Glu Ile Ile Leu Lys Glu Lys Gln Glu Glu Arg Leu Thr Trp Val Thr
            100                 105                 110

Ser Thr Thr Thr Leu Gly Leu Lys Ser Tyr Tyr Trp Arg Val Gln Arg

```
            115                 120                 125
Tyr Leu Lys Asp Lys Tyr Asn Ser Tyr Ala Trp Met Val Val Arg
    130                 135                 140

Ala Glu Val Phe Arg Asn Phe Ser Ile Ile Leu Arg Leu Asn Arg Asn
145                 150                 155                 160

Phe Gln Asn

<210> SEQ ID NO 44
<211> LENGTH: 166
<212> TYPE: PRT
<213> ORGANISM: Macaca fascicularis

<400> SEQUENCE: 44

Met Ser Tyr Asn Leu Leu Gly Phe Leu Gln Arg Ser Ser Phe Gln
1               5                   10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Pro Gln
            35                  40                  45

Gln Phe Gln Lys Glu Asp Ala Ala Leu Thr Ile Tyr Glu Met Leu Gln
    50                  55                  60

Asn Ile Tyr Ala Ile Phe Arg Gln Asp Leu Ser Ser Thr Gly Trp Asn
65                  70                  75                  80

Glu Thr Ile Val Glu Asn Leu Leu Ala Asn Val Tyr His Gln Ile Asp
                85                  90                  95

His Leu Lys Thr Ile Leu Glu Glu Lys Leu Glu Lys Glu Asp Phe Thr
            100                 105                 110

Arg Gly Lys Phe Val Ser Ser Leu His Leu Lys Arg Tyr Tyr Gly Arg
    115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Phe Phe Ile Asn Lys Leu
145                 150                 155                 160

Thr Gly Tyr Leu Arg Asn
                165

<210> SEQ ID NO 45
<211> LENGTH: 159
<212> TYPE: PRT
<213> ORGANISM: Oryctolagus cuniculus

<400> SEQUENCE: 45

Met Ser Tyr Asn Ser Leu Gln Ile Gln Leu Trp His Gly Ser Leu Thr
1               5                   10                  15

Cys Ala Lys Leu Leu Gln Leu Asn Gly Thr Thr Glu Asp Cys Leu
                20                  25                  30

Asn Glu Arg Ile Asn Phe Lys Val Pro Lys Glu Ile Lys Glu Pro Gln
            35                  40                  45

Gln Leu Gln Lys Glu Asp Thr Thr Leu Val Ile Phe Glu Met Leu Asn
    50                  55                  60

Asn Ile Phe Asp Ile Phe Arg Lys Asn Phe Ser Ser Thr Gly Trp Asn
65                  70                  75                  80

Glu Thr Leu Val Glu Asn Leu Leu Gly Glu Thr His Leu Gln Ile His
                85                  90                  95

His Leu Lys Ser Lys Ile Asn Lys Lys Val Thr Leu Glu Ser Ile Arg
            100                 105                 110
```

```
Met Asn Leu Arg Leu Lys Ser Tyr Tyr Trp Arg Ile Met Asp Tyr Leu
        115                 120                 125

Glu Thr Lys Gln Tyr Ser Asn Cys Ala Trp Lys Ile Val Gln Leu Glu
    130                 135                 140

Ile Phe Arg Asn Phe Ser Phe Ile Ile Met Leu Ile Asp Tyr Leu
145                 150                 155

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ala Ser Gln Ser Ile Ser Ser Tyr Leu Asn
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Ala Ser Ser Leu Gln Ser
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Gln Ser Tyr Ser Thr Pro
1               5

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Ser Ser Gln Ser Leu Leu His Ser Asp Gly Lys Thr Tyr Leu Tyr
1               5                   10                  15

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Val Ser Asn Arg Phe Ser
1               5
```

```
<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Met Gln Ser Ile Gln Leu Pro
1               5

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ser Ser Gln Ser Leu Val Tyr Ser Asp Gly Asn Thr Tyr Leu Asn
1               5                   10                  15

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Val Ser Asn Arg Asp Ser
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Met Gln Gly Thr His Trp Pro
1               5

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Ser Ser Gln Ser Val Leu Tyr Ser Ser Asn Asn Lys Asn Tyr Leu
1               5                   10                  15

Ala

<210> SEQ ID NO 56
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 56

Trp Ala Ser Thr Arg Glu Ser
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Gln Tyr Tyr Ser Thr Pro
1               5

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ala Ser Gln Ser Ile Ser Ser Trp Leu Ala
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Ala Ser Ser Leu Glu Ser
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Gln Tyr Asn Ser Tyr Ser
1               5

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Ala Ser Gln Asp Ile Ser Asn Tyr Leu Asn
1               5                   10
```

```
<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp Ala Ser Asn Leu Glu Thr
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Gln Tyr Asp Asn Leu Pro
1               5

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ala Ser Gln Gly Ile Ser Ser Tyr Leu Ala
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ala Ser Thr Leu Gln Ser
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Gln Leu Asn Ser Tyr Pro
1               5

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67
```

Arg Ala Ser Gln Ser Val Ser Ser Asn Leu Ala
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Ala Ser Thr Arg Ala Thr
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Gln Tyr Asn Asn Trp Pro
1               5

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Ala Ser Gln Ser Val Ser Ser Tyr Leu Ala
1               5                   10

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Ala Ser Asn Arg Ala Thr
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Gln Arg Ser Asn Trp Pro
1               5

<210> SEQ ID NO 73
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 73

Arg Ala Ser Gln Ser Val Ser Ser Tyr Leu Ala
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Ala Ser Ser Arg Ala Thr
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Gln Tyr Gly Ser Ser Pro
1               5

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Ser Ser Gln Ser Leu Leu His Ser Asn Gly Tyr Asn Tyr Leu Asp
1               5                   10                  15

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Gly Ser Asn Arg Ala Ser
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Met Gln Ala Leu Gln Thr Pro
1               5
```

```
<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Gly Asp Ser Leu Arg Ser Tyr Tyr Ala Ser
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Lys Asn Asn Arg Pro Ser
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asn Ser Arg Asp Ser Ser Gly Asn His
1               5

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Gly Ser Ser Ser Asn Ile Gly Ala Gly Tyr Asp Val His
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Asn Ser Asn Arg Pro Ser
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 84

Gln Ser Tyr Asp Ser Ser Leu Ser Gly
1               5

<210> SEQ ID NO 85
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Arg Ser Ser Gly Ser Ile Ala Ser Asn Tyr Val Gln
1               5                   10

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Glu Asp Asn Gln Arg Pro Ser
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gln Ser Tyr Asp Ser Ser Asn
1               5

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Thr Gly Ser Ser Ser Gly Gly Ser Tyr Tyr Val Ser
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Thr Gly Ser Ser Ser Asp Val Gly Gly Ser Tyr Tyr Val Ser
1               5                   10

<210> SEQ ID NO 90
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 90

Glu Asn Asp Ser Asn Arg Pro Ser
1               5

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser or Asp
<220> FEATURE:
<221> NAME/KEY: MOD_RES
<222> LOCATION: (8)..(8)
<223> OTHER INFORMATION: Gln or Gly

<400> SEQUENCE: 91

Glu Asp Ser Asn Arg Xaa Lys Xaa Gln Lys Pro Ser
1               5                   10

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Asn or Thr

<400> SEQUENCE: 92

Gln Ser Trp Asp Ser Ser Ala Xaa
1               5

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Asn or Thr
<220> FEATURE:
<221> NAME/KEY: MOD_RES
<222> LOCATION: (10)..(10)
<223> OTHER INFORMATION: Phe or Val
<220> FEATURE:
<221> NAME/KEY: MOD_RES
<222> LOCATION: (11)..(11)
<223> OTHER INFORMATION: Gly or Val

<400> SEQUENCE: 93

Gln Ser Trp Asp Ser Ser Ala Xaa Phe Xaa Xaa
1               5                   10

<210> SEQ ID NO 94
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ala or Tyr
<220> FEATURE:
<221> NAME/KEY: MOD_RES
<222> LOCATION: (13)..(13)
<223> OTHER INFORMATION: Asn, His or Ser

<400> SEQUENCE: 94

Ser Gly Ser Ser Ser Asn Ile Gly Asn Asn Xaa Val Xaa
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Ala or Tyr
<220> FEATURE:
<221> NAME/KEY: MOD_RES
<222> LOCATION: (14)..(14)
<223> OTHER INFORMATION: Asn, His or Ser

<400> SEQUENCE: 95

Ser Gly Ser Ser Ser Asn Ile Ile Gly Asn Asn Xaa Val Xaa
1               5                   10

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys, Asn or Gln

<400> SEQUENCE: 96

Gly Asn Asn Xaa Arg Pro Ser
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Asn or Ser

<400> SEQUENCE: 97

Ala Ala Trp Asp Asp Ser Leu Xaa Gly
1               5

<210> SEQ ID NO 98
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala or Val
<220> FEATURE:
<221> NAME/KEY: MOD_RES
<222> LOCATION: (8)..(8)
<223> OTHER INFORMATION: Lys or Ser

<400> SEQUENCE: 98

Cys Ser Gly Asp Xaa Leu Gly Xaa Lys Tyr Ala His
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Lys Asp Ser Glu Arg Pro Ser
1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Asn, Asp, Thr or Ala

<400> SEQUENCE: 100

Gln Ser Trp Asp Ser Ser Gly Xaa
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Asn, Asp, Thr or Ala

<400> SEQUENCE: 101

Gln Ser Trp Asp Ser Ser Gly Xaa His
1               5

<210> SEQ ID NO 102
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 102

Arg Ala Ser Gln Ser Leu Leu His Ser Asp Gly Ile Ser Ser Tyr Leu
1               5                   10                  15
Ala

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Ala Ser Gln Gly Ile Ser Ser Tyr Leu Ala
1               5                   10

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ala Ala Ser Ser Arg Ala Ser
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gln Gln Tyr Asn Ser Tyr Pro
1               5

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Asn or Ser

<400> SEQUENCE: 106

Arg Ala Ser Gln Gly Ile Ser Xaa Tyr Leu Ala
1               5                   10

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Ala Ser Ser Leu Gln Ser
```

```
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gln Gln Tyr Asn Ser Tyr Pro
1               5

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Ser Ser Gln Ser Leu Leu His Ser Asp Gly Asn Thr Tyr Leu Asp
1               5                   10                  15

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Ser Ser Gln Ser Leu Leu His Ser Asp Asp Gly Asn Thr Tyr Leu
1               5                   10                  15
Asp

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Thr
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (6)..(6)
<223> OTHER INFORMATION: Ala or Phe

<400> SEQUENCE: 111

Xaa Xaa Ser Asn Arg Xaa Ser
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 112

Met Gln Ala Thr Gln Phe Pro
1               5

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Ser or Val

<400> SEQUENCE: 113

Arg Ala Ser Gln Ser Xaa Xaa Ser Ser Tyr Leu Ala
1               5                   10

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Ala Ser Thr Arg Ala Thr
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser, Asn, Gly or His

<400> SEQUENCE: 115

Gln Gln Tyr Xaa Asn Trp Pro
1               5

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Phe Thr Phe Ser Ser Tyr Trp Met Ser
1               5                   10

<210> SEQ ID NO 117
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 117

Ala Asn Ile Lys Gln Asp Gly Ser Glu Lys Tyr Tyr Val Asp Ser Val
1               5                   10                  15

Lys Gly

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Phe Thr Phe Ser Ser Tyr Ala Met Ser
1               5                   10

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Ile Ser Gly Ser Gly Gly Ser Thr Tyr Tyr Ala Asp Ser Val Lys
1               5                   10                  15

Gly

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Gly Ser Ile Ser Ser Tyr Tyr Trp Ser
1               5                   10

<210> SEQ ID NO 121
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Tyr Ile Tyr Tyr Ser Gly Ser Thr Asn Tyr Asn Pro Ser Leu Lys
1               5                   10                  15

Ser

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122
```

```
Gly Tyr Thr Phe Thr Gly Tyr Tyr Met His
1               5                   10
```

<210> SEQ ID NO 123
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

```
Gly Trp Ile Asn Pro Asn Ser Gly Gly Thr Asn Tyr Ala Gln Lys Phe
1               5                   10                  15

Gln Gly
```

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

```
Gly Gly Thr Phe Ser Ser Tyr Ala Ile Ser
1               5                   10
```

<210> SEQ ID NO 125
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

```
Gly Gly Ile Ile Pro Ile Phe Gly Thr Ala Asn Tyr Ala Gln Lys Phe
1               5                   10                  15

Gln Gly
```

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

```
Gly Tyr Thr Gly Thr Ser Tyr Tyr Met His
1               5                   10
```

<210> SEQ ID NO 127
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

```
Gly Ile Ile Asn Pro Ser Gly Gly Ser Thr Ser Tyr Ala Gln Lys Phe
1               5                   10                  15

Gln Gly
```

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Phe Thr Phe Ser Ser Tyr Gly Met His
1               5                   10

<210> SEQ ID NO 129
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Val Ile Ser Tyr Asp Gly Ser Asn Lys Tyr Tyr Ala Asp Ser Val
1               5                   10                  15

Lys Gly

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Phe Thr Phe Ser Ser Tyr Ser Met Asn
1               5                   10

<210> SEQ ID NO 131
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Tyr Ile Ser Ser Ser Ser Ser Thr Ile Tyr Tyr Ala Asp Ser Val
1               5                   10                  15

Lys Gly

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Phe Thr Phe Ser Asn Ala Trp Met Ser
1               5                   10

<210> SEQ ID NO 133
<211> LENGTH: 20
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 133

Gly Arg Ile Lys Ser Lys Thr Asp Gly Gly Thr Thr Asp Tyr Ala Ala
1               5                   10                  15

Pro Val Lys Gly
            20

<210> SEQ ID NO 134
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Gly Ser Ile Ser Ser Ser Ser Tyr Tyr Trp Gly
1               5                   10

<210> SEQ ID NO 135
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Ser Ile Tyr Tyr Ser Gly Ser Thr Tyr Tyr Asn Pro Ser Leu Lys
1               5                   10                  15

Ser

<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Gly Ser Ile Ser Ser Gly Asp Tyr Tyr Trp Ser
1               5                   10

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Tyr Ile Tyr Tyr Ser Gly Ser Thr Tyr Tyr Asn Pro Ser Leu Lys
1               5                   10                  15

Ser

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 138

Gly Tyr Ser Phe Thr Ser Tyr Trp Ile Gly
1               5                   10

<210> SEQ ID NO 139
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Ile Ile Tyr Pro Gly Asp Ser Asp Thr Arg Tyr Ser Pro Ser Phe
1               5                   10                  15

Gln Gly

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: His or Ser

<400> SEQUENCE: 140

Gly Phe Thr Phe Ser Ser Tyr Ala Met Xaa
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: His or Ser

<400> SEQUENCE: 141

Gly Phe Thr Phe Ser Ser Tyr Ala Met Xaa Trp Ser
1               5                   10

<210> SEQ ID NO 142
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Trp Ile Ser Pro Asn Gly Gly Ser Thr Tyr Tyr Ala Asp Ser Val
1               5                   10                  15

Lys Gly

<210> SEQ ID NO 143
<211> LENGTH: 20
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 143

Gly Trp Ile Ser Pro Lys Ala Asn Gly Gly Ser Thr Tyr Tyr Ala Asp
1               5                   10                  15

Ser Val Lys Gly
            20

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Phe Thr Phe Ser Ser Tyr Ala Met Ser
1               5                   10

<210> SEQ ID NO 145
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Gly or Ser

<400> SEQUENCE: 145

Ser Val Ile Ser Ser Asp Gly Xaa Ser Thr Tyr Tyr Ala Asp Ser Val
1               5                   10                  15

Lys Gly

<210> SEQ ID NO 146
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Gly or Ser

<400> SEQUENCE: 146

Ser Val Ile Ser Ser Lys Ala Asp Gly Xaa Ser Thr Tyr Tyr Ala Asp
1               5                   10                  15

Ser Val Lys Gly
            20

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
```

```
<223> OTHER INFORMATION: Ser, Gly or His

<400> SEQUENCE: 147

Gly Tyr Ser Phe Thr Ser Tyr Trp Ile Xaa
1               5                   10

<210> SEQ ID NO 148
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Arg, Ile or Ser

<400> SEQUENCE: 148

Gly Xaa Ile Tyr Pro Gly Asp Ser Asp Thr Arg Tyr Ser Pro Ser Phe
1               5                   10                  15

Gln Gly

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ala or Tyr
<220> FEATURE:
<221> NAME/KEY: MOD_RES
<222> LOCATION: (9)..(9)
<223> OTHER INFORMATION: Ile or Met

<400> SEQUENCE: 149

Gly Tyr Thr Phe Thr Ser Tyr Xaa Xaa His
1               5                   10

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Gly or Tyr

<400> SEQUENCE: 150

Gly Trp Ile Asn Pro Xaa Asn Gly Asn Thr Asn Tyr Ala Gln Lys Phe
1               5                   10                  15

Gln

<210> SEQ ID NO 151
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (8)..(8)
<223> OTHER INFORMATION: Asn or Tyr

<400> SEQUENCE: 151

Gly Gly Ser Ile Ser Ser Gly Xaa Tyr Tyr Trp Ser
1               5                   10

<210> SEQ ID NO 152
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Tyr Ile Tyr Tyr Ser Gly Ser Thr Tyr Tyr Asn Pro Ser Leu Lys
1               5                   10                  15

Ser

<210> SEQ ID NO 153
<211> LENGTH: 19
<212> TYPE: PRT
<213> ORGANISM: Homo sapiens

<400> SEQUENCE: 153

Tyr Asn Leu Leu Gly Phe Leu Gln Arg Ser Ser Asn Phe Gln Cys Gln
1               5                   10                  15

Lys Leu Leu

<210> SEQ ID NO 154
<211> LENGTH: 19
<212> TYPE: PRT
<213> ORGANISM: Homo sapiens

<400> SEQUENCE: 154

Lys Glu Asp Ala Ala Leu Thr Ile Tyr Glu Met Leu Gln Asn Ile Phe
1               5                   10                  15

Ala Ile Phe

<210> SEQ ID NO 155
<211> LENGTH: 26
<212> TYPE: PRT
<213> ORGANISM: Homo sapiens

<400> SEQUENCE: 155

Glu Thr Ile Val Glu Asn Leu Leu Ala Asn Val Tyr His Gln Ile Asn
1               5                   10                  15

His Leu Lys Thr Val Leu Glu Glu Lys Leu
            20                  25

<210> SEQ ID NO 156
<211> LENGTH: 17
<212> TYPE: PRT
<213> ORGANISM: Homo sapiens

<400> SEQUENCE: 156

Ser Leu His Leu Lys Arg Tyr Tyr Gly Arg Ile Leu His Tyr Leu Lys
1               5                   10                  15

Ala

<210> SEQ ID NO 157
```

<211> LENGTH: 22
<212> TYPE: PRT
<213> ORGANISM: Homo sapiens

<400> SEQUENCE: 157

His Cys Ala Trp Thr Ile Val Arg Val Glu Ile Leu Arg Asn Phe Tyr
1               5                   10                  15

Phe Ile Asn Arg Leu Thr
            20

<210> SEQ ID NO 158
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Met Ser Tyr Asn Leu Leu Gly Phe Leu Gln Arg Ser Ser Asn Arg Arg
1               5                   10                  15

Cys Leu Met Leu Leu Ala Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 159
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg His Asp Phe Gly Ile Pro Gln Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 160
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Met Ser Tyr Asn Leu Leu Gly Phe Leu Gln Arg Ser Asn Phe Gln
1               5                   10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Ile Phe Arg Gln Asp Ser Ser Ser Thr Gly Trp Asn
65                  70                  75                  80

Glu Thr Ile Val Asp Lys Leu Leu Thr Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 161
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Met Ser Tyr Asn Leu Leu Gly Phe Leu Gln Arg Ser Asn Phe Gln
1               5                   10                  15

```
Cys Gln Lys Leu Leu Trp Gln Leu Asn Gly Arg Leu Glu Tyr Cys Leu
             20                  25                  30

Lys Asp Arg Met Asn Phe Asp Ile Pro Glu Glu Ile Lys Gln Leu Gln
         35                  40                  45

Gln Phe Gln Lys Glu Asp Ala Ala Leu Thr Ile Tyr Glu Met Leu Gln
     50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Glu Val Tyr Gln Gln Ile Asn
                 85                  90                  95

Asp Leu Glu Ala Val Leu Glu Glu Lys Leu Glu Lys Glu Asp Phe Thr
             100                 105                 110

Arg Gly Lys Leu Met Ser Ser Leu His Leu Lys Arg Tyr Tyr Gly Arg
         115                 120                 125

Ile Leu His Tyr Leu Lys Ala Lys Glu Tyr Ser His Cys Ala Trp Thr
     130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 162
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
             20                  25                  30

Lys Asp Arg Met Asn Phe Asp Ile Pro Glu Glu Ile Lys Gln Leu Gln
         35                  40                  45

Gln Phe Gln Lys Glu Asp Ala Ala Leu Thr Ile Tyr Glu Met Leu Gln
     50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
             100                 105                 110

Arg Gly Lys Leu Met Ser Ile Leu His Leu Arg Lys Tyr Tyr Gly Arg
         115                 120                 125

Ile Leu His Tyr Leu Lys Ala Lys Glu Tyr Ser His Cys Ala Trp Thr
     130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 163
<211> LENGTH: 166
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 163

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Glu Lys Lys Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 164
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser Pro Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
            165

<210> SEQ ID NO 165
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Ala Glu Ile Leu Arg Asn Phe Ser Leu Ile Thr Arg Leu
145                 150                 155                 160

Thr Gly Tyr Leu Arg Asn
            165

<210> SEQ ID NO 166
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166
caggtgcagc tggtgcagag cggcgccgag gtgaagaagc ccggcagcag cgtgaaggtg      60
agctgcaagg ccagcggcta caccttcagc cggtactgga tgcactgggt gcggcaggcc     120
cccggccagg gcctggagtg gatgggccac atcgacccca gcgacagcta cacctactac     180
aaccagaagt tcaagggccg ggtgaccatc accgccacg agagcaccag caccgcctac     240
atggagctga gcagcctgcg gagcgaggac accgccgtgt actactgcgc ccggtgggac     300
tacggcaacc tgctgttcga gtactggggc cagggcaccc tggtgaccgt ctcgagc        357

<210> SEQ ID NO 167
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167

```
gacatccaga tgacccagag ccccagcagc ctgagcgcca gcgtgggcga ccgggtgacc      60
atcacctgcc ggaccagcca ggacatcggc aactacctga actggtacca gcagaagccc     120
ggcaaggcct tcaagctgct gatctacagc accagcggc tgcacagcgg cgtgcccagc      180
cggttcagcg gcagcggcag cggcaccgac ttcaccctga ccatcagcag cctgcagccc     240
gaggacttcg ccacctacta ctgccagcag gggattattt tgcccattac cttcggcggc     300
ggcaccaagg tggagatcaa g                                               321
```